(12) United States Patent
Baldwin et al.

(10) Patent No.: US 6,790,965 B1
(45) Date of Patent: Sep. 14, 2004

(54) COMBINATORIAL DIHYDROBENZOPYRAN LIBRARY

(75) Inventors: John J. Baldwin, Gwynedd Valley, PA (US); John C. Reader, Princeton, NJ (US); Lawrence W. Dillard, Hopewell, NJ (US); Ge Li, Plainsboro, NJ (US); Wenguang Zeng, Lawrenceville, NJ (US)

(73) Assignee: Pharmacopeia Drug Discovery, Inc., Cranbury, NJ (US)

( * ) Notice: Subject to any disclaimer, the term of this patent is extended or adjusted under 35 U.S.C. 154(b) by 0 days.

(21) Appl. No.: 09/391,783

(22) Filed: Sep. 8, 1999

Related U.S. Application Data

(60) Division of application No. 09/295,125, filed on Apr. 20, 1999, now abandoned, which is a division of application No. 08/733,803, filed on Oct. 18, 1996, now Pat. No. 6,017,768, which is a continuation-in-part of application No. 08/552,698, filed on Nov. 3, 1995, now Pat. No. 5,821,130, which is a continuation-in-part of application No. 08/436,120, filed on May 8, 1995, now abandoned, which is a continuation-in-part of application No. 08/239,302, filed on May 6, 1994, now abandoned.

(51) Int. Cl.[7] .................... C07D 327/04; C07D 305/14; A01N 43/26; G01N 33/543; C07C 233/00
(52) U.S. Cl. .................. 549/32; 436/531; 436/530; 436/529; 436/528; 436/527; 436/526; 436/525; 436/524; 436/518; 564/184; 564/186; 564/183; 514/456; 514/440; 549/265; 549/40; 549/404; 549/408
(58) Field of Search .................. 436/531, 530, 436/529, 528, 527, 526, 525, 524, 518, 7.1; 564/184, 186, 183; 514/456, 440; 549/32, 265, 40, 404, 408

(56) References Cited

U.S. PATENT DOCUMENTS

| 4,499,299 A | | 2/1985 | Bernstein et al. ........... 562/434 |
| 4,665,203 A | * | 5/1987 | Miyano et al. ............. 549/402 |
| 5,268,386 A | * | 12/1993 | Harada et al. .............. 514/456 |
| 6,017,768 A | * | 1/2000 | Baldwin et al. |

FOREIGN PATENT DOCUMENTS

| EP | 0415566 A1 | * | 3/1991 |
| WO | WO 87/00840 | | 2/1987 |
| WO | WO 91/11749 A1 | * | 8/1991 |
| WO | WO 94/08051 | | 4/1994 |
| WO | WO 95/30642 | | 11/1995 |

OTHER PUBLICATIONS

Mukai et al. Kinetic studies of antioxidant activity of new tocopherol model compounds in solution. Bull. Chem. Soc. Jpn., vol. 60, Jun. 1987, pp. 2163–2167.*

Gan et al. Insect antijuvenile hormone analogs. II. Synthesis of terpenoxychromene derivatives. Huaxue Xuebao, vol. 39 (7–8–9), 1981, pp. 777–792, Abstract only.*

Jennings, J. Chem. Soc. Perkin Trans. p. 1733–1738, 1984.*

Barany and Albericio, J. Amer. Chem. Soc., 107, 4936–4942, 1985.

Carey et al., Adv. Org. Chem., 2nd ed., Part B., p. 101, 1977.

Takematsu et al., Chem. Abstr. 236509b, vol. 107, p. 769, 1991.

Brown et al., J. Med. Chem., vol. 32, No. 4, pp 807–826, Apr. 1989.

Cohen et al., "3,4–Dihydro–2H–1–benzopyran–2–carboxylic Acids and Related Compounds as Leukotriene Antagonists", Journal of Medicinal Chemistry, 1989, vol. 32, No. 8, pp. 1842–1860.

Harada et al., "Preparation of spirobenzopyran compounds useful in inhibiting biosynthesis and accelerating the excretion of uric acid", Chem. Abstracts, vol. 115, No. 7, Aug. 19, 1991, p. 774 Col. 2.

Jennings, Richard C. and Ottridge, Anthony P., "The Synthesis of the Epoxide and some other possible Metabolites of Precocene I," J. Chem. Soc. Perkin Trans. I., 8:1733–38 (1984).

* cited by examiner

*Primary Examiner*—Maurie Garcia Baker
(74) *Attorney, Agent, or Firm*—Heslin Rothenberg Farley & Mesiti P.C.

(57) ABSTRACT

Combinatorial libraries are disclosed which are represented by Formula I:

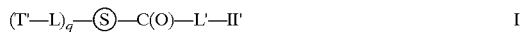

wherein:

Ⓢ is a solid support; T—L— is an identifier residue; and —L'—II' is a ligand/linker residue. These libraries contain dihydrobenzopyrans of the formula:

II

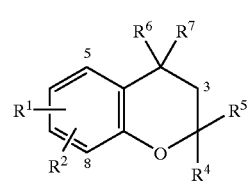

which interact (i.e., as agonists or antagonists) with α adrenergic receptors, dopamine receptors, δ-opiate receptors, and K⁺ channels and are inhibitors of carbonic anhydrase isozymes. They are useful in the treatment of ocular diseases such as glaucoma.

5 Claims, No Drawings

COMBINATORIAL DIHYDROBENZOPYRAN LIBRARY

CROSS REFERENCE TO RELATED APPLICATIONS

This application is a divisional of U.S. patent application, Ser. No. 09/295,125, filed Apr. 20, 1999 now abandoned, which itself is a divisional of U.S. patent application, Ser. No. 08/733,803, filed Oct. 18, 1996 now U.S. Pat. No. 6,017,768, which is itself a continuation in part of U.S. patent application, Ser. No. 08/552,698, filed Nov. 3, 1995, now U.S. Pat. No. 5,821,130, which was itself a continuation in part of U.S. patent application, Ser. No. 08/436,120, filed May 9, 1995, now abandoned, which was itself a continuation in part of U.S. patent application, Ser. No. 08/239,302, filed May 6, 1994, now abandoned.

BACKGROUND OF THE INVENTION

There is interest in methods for the synthesis of large numbers of diverse compounds which can be screened for various possible physiological or other activities. Techniques have been developed in which one adds individual units sequentially as part of the chemical synthesis to produce all or a substantial number of the possible compounds which can result from all the different choices possible at each sequential stage of the synthesis. For these techniques to be successful, it is necessary for the compounds to he amenable to methods by which one can is determine the structure of the compounds so made. Brenner and Lerner (*PNAS USA* 81: 5381–83 (1992)) and WO 93/20242, for example, describe a synthesis wherein oligonucleotides are produced in parallel with and are chemically linked as genetic tags to oligopeptides as the compounds of interest. WO 93/06121 teaches methods for particle-based synthesis of random oligomers wherein identification tags on the particles are used to facilitate identification of the oligomer sequence synthesized. A detachable tagging system is described in Ohlmeyer et al., *Proc. Natl. Acad. Sci. USA*, 12, 10922–0926, December, 1993.

SUMMARY OF THE INVENTION

The present invention relates to combinatorial chemical libraries of compounds encoded with tags and to the use of these libraries in assays to discover biologically active compounds. The present invention also relates to libraries containing dihydrobenzopyrans and using these libraries to identify biologically active members by screening for inhibition of carbonic anhydrase isozymes. The present invention also relates to members of the library which interact (i.e., as agonists or antagonists) with α adrenergic receptors, dopamine receptors, θ-opiate receptors, and K+ channels. In particular, the present invention also relates to members of the library which are inhibitors of carbonic anhydrase. The invention also relates to methods for their preparation, intermediates, and to methods and pharmaceutical formulations for using these dihydrobenzopyrans in the treatment of mammals, especially humans.

Because of their activity as inhibitors of carbonic anhydrase isozymes, compounds of the present invention are useful in the treatment of such diseases as glaucoma.

DETAILED DESCRIPTION OF THE INVENTION

The combinatorial libraries of the present invention are represented by Formula I:

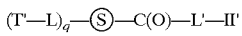

wherein:

Ⓢ is a solid support;

T'—L— is an identifier residue;

—L'—II' is a compound/linker residue; and q is 3–30.

Preferred compounds of Formula I are those wherein:

T'—L— is of the Formula:

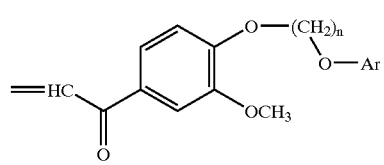

wherein n=3–12 when Ar is pentachlorophenyl and
n=3–6 when Ar is 2,4,6-trichlorophenyl;

q is 4–12;

and —L'— is

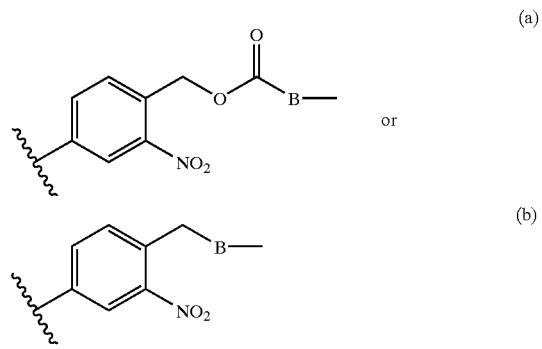

wherein the left-hand bond as shown is the point of attachment to the solid support and the right hand bond is the point of attachment to the compound, and B is O or $N(CH_2)_{1-6}R^{17}$, with the proviso that in (b) when B is $N(CH_2)_{1-6}R^{17}$, the compound is attached to B through a carbonyl group.

Other preferred compounds of Formula I are those of Formulae Ia, Ib, or Ic wherein —C(O)—L'—II' is:

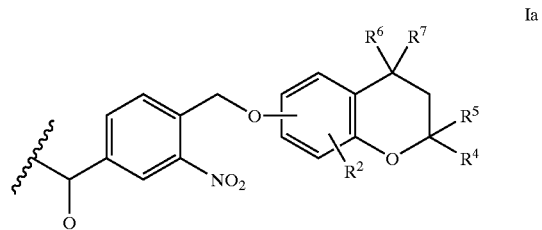

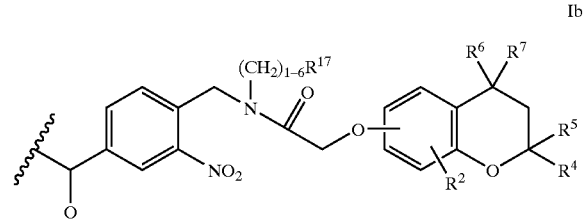

-continued

Ic $R^{17}$ is H; alkyl; alkyl substituted by 1–3 alkoxy, S-loweralkyl, sulfamoyl, halo, alkylsulphonamido, or arylsulphonamido; alkenyl; alkynyl; aryl; substituted aryl; heteroaryl; substituted heteroaryl; heterocycloalkyl; substituted heterocycloalkyl; diphenylmethyl; —$CH_2NR^{15}C(O)R^{16}$; —$C(O)NR^{16}R^{16}$; —$CH_2OC(O)R^{16}$; or —$CH_2SC(O)R^{16}$.

Depending on the choice of L' (see Table 1), the ligands of Formula II may be detached by photolytic, oxidative, or other cleavage techniques. For example, when —L'— is (b) and B is O (or $N(CH_2)_{1-6}R^{17}$), photolytic detachment may be represented by:

$$I \xrightarrow{hv} (T'—L)_q—(S)—C(O)—L''+ II'OH \quad (B=O) \text{ or}$$
$$—II'NH(CH_2)_{1-6}R^{17} \quad (B=NH(CH_2)_{1-6}R^{17})$$

wherein L" is the residue from L' and II'OH (or II'NH-$(CH_2)_{1-6}R^{17}$) is II.

Therefore, compounds of the present invention are also represented by Formula II

II wherein:

$R^1$ is OH, $O(CH_2)_{1-2}OH$, $OCH_2CO_2H$, $CO_2H$, $OCH_2C(O)NHCHR^{18}(CH_2)_{0-5}R^{17}$ or $OCH_2$-4-Phe-$C(O)NHCHR^{19}(CH_2)_{0-5}R^{17}$ $R^2$ is H or lower alkyl;

$R^3$ is H, alkyl, aryl, or arylalkyl;

$R^4$ and $R^5$ are each independently H, lower alkyl, or substituted lower alkyl where the substituents are 1–3 alkoxy, aryl, substituted aryl, carboalkoxy, carboxamido, diloweralkylamido or

—$(CH_2)_{1-4}$—N⟨ ⟩N—$R^8$;

or $R^4$ and $R^5$ taken together are —$(CH_2)_n$—, —$(CH_2)_2$—O—$(CH_2)_2$—, —$CH_2$—O—$(CH_2)_3$—, —$(CH_2)_2$—$NR^5$—$(CH_2)_2$—, —$CH_2NR^8$—$(CH_2)_m$—, —$(CH_2)_2CH(NHR^9)(CH_2)_2$—, —$(CH_2)_2$—$S(O)_{0-2}$—$(CH_2)_2$—, or —$CH_2CH(N$-loweralkyl$)(CH_2)_2CHCH_2$— one of $R^6$ and $R^7$ is H and the other is H, OH, or $N(CH_2)_{1-6}R^{14}R^{15}$; or $R^6$ and $R^7$ taken together are $R^8$ is H, $COOR^9$, $CONHR^{10}$, $CSNHR^{11}$, $COR^{12}$, $SO_3R^{13}$, lower alkyl, aryllower alkyl, heteroaryl, or heteroaryl lower alkyl, wherein aryl is optionally substituted with 1–3 substituents selected from lower alkyl, lower alkoxy, halo, CN, $NH_2$, COOH, $CONH_2$, carboalkoxy, and mono- or di-lower alkylamino and wherein heteroaryl is a mono- or bicyclic heteroaromatic ring system of 5 to 10 members including 1 to 3 heteroatoms selected from O, N, and S and 0–3 substituents selected from halo, amino, cyano, lower alkyl, carboalkoxy, $CONH_2$, and S-lower alkyl;

$R^9$ is lower alkyl, aryl, aryl lower alkyl, heteroaryl, aryl substituted by 1–3 substituents selected from alkyl, alkenyl, alkoxy, methylene dioxy, and halo, or a 5 to 6-memered heterocyclic ring wherein the hetero atom is O or N, wherein heteroaryl is a heteroaromatic ring of 5 to 6 members including 1 to 2 heteroatoms selected for O, N, and S and 0–2 substituents selected from lower alkyl, dialkylamino, lower alkoxy, and halo;

$R^{10}$ and $R^{11}$ are each independently lower alkyl, aryl, aryl lower alkyl, or aryl substituted by 1–3 subscizuents selected from lower alkyl, halo, alkoxy, and haloalkyl;

$R^{12}$ is lower alkyl, aryl, heterorayl, aryl lower alkyl heteroaryl lower alkyl, a 5- or 6-membered hererocyclic ring containing 1–2 heteroatoms selected from O, S, and N, a 5- or 6-membered heterocyclic ring containing 1–2 heteroatoms selected from O, S, and N lower alkyl, or aryl substituted with 1–3 substituents selected from lower alkyl, alkoxy, halo, sulfamoyl, lower alkyl sulfamoyl, cyano, and phenyl;

$R^{13}$ is lower alkyl, aryl, or aryl substituted with 1–3 substituents selected from lower alkyl, alkoxy, halo, CN, and haloalkyl;

$R^{14}$ is H; alkyl; alkyl substituted by 1–3 alkoxy, S-loweralkyl, sulfamoyl, halo, alkylsulphonamido, or arylsulphonamido; alkenyl; alkynyl; aryl; substituted aryl; heteroaryl; substituted heteroaryl; heterocycloalkyl; —$CH_2NR^{16}C(O)R^{16}$; —$C(O)NR^{16}R^{16}$; —$CH_2OC(O)R^{16}$; or —$CH_2SC(O)R^{16}$;

$R^{15}$ is H, alkyl, —$C(O)X$, —$C(S)X$, or —$C(NCN)NR^3R^3$;

$R^{16}$ is lower alkyl, substituted lower alkyl, aryl, or substituted aryl;

$R^{17}$ is H; alkyl; alkyl substituted by 1–3 alkoxy, 2-loweralkyl sulfamoyl, halo, alkylsulphonamido, or arylsulphonamido; alkenyl; alkynyl; aryl; substituted aryl; heteroaryl; substituted heteroaryl; heterocycloalkyl; diphenylmethyl; —$CH_2NR^{16}C(O)R^{16}$; —$C(O)NR^{16}R^{16}$; —$CH_2OC(O)R^{16}$; or —$CH_2SC(O)R^{16}$; or substituted heterocycloalkyl;

X is alkyl, aryl, arylalkyl, O-loweralkyl, or $NR^3R^3$

Z is —$(CH_2)_{1-6}$—, optionally substituted with 1–3 lower alkyl; $CHR^2$; Phe-$CH_2$—, where Phe is optionally mono-substituted with halogen, lower alkyl, or alkoxy; or heteroarylene-$(CH_2)$—;

m is 2 or 3;

n is 4–9;

or a pharmaceutically acceptable salt thereof.

Preferred compounds of Formula II are those wherein $R^{12}$ is sulfamoylphenyl, most preferably p-sulfamoylphenyl.

A preferred embodiment of the invention is a compound of Formula II wherein:

$R^1$ is $OCH_2C(O)NHCHR^{18}(CH_2)_{0-5}R^{17}$ or $OCH_2$-4-Phe-$C(O)NHCHR^{18}(CH_2)_{0-5}R^{17}$ $R^2$ is H or lower alkyl;

$R^4$ and $R^5$ are each lower alkyl or

—$(CH_2)_{1-4}$—N⟨piperazine⟩N—$R^8$;

or $R^4$ and $R^5$ taken together are —$(CH_2)_5$—, —$(CH_2)$—O—$(CH_2)_2$, —$(CH_2)_2$—$NR^8$—$(CH_2)_2$—, —$(CH_2)_2$—$CH(NHR^8)(CH_2)_2$—, —$(CH_2)_2$—S—$(CH_2)_2$—, or —$CH_2CH(NCH_3)(CH_2)_2CHCH_2$—;

$R^6/R^7$ are H/OH, =O, or —$S(CH_2)_2S$—;

$R^8$ is H, $COOR^9$, $CONHR^{10}$, $CSNHR^{11}$, $COR^{12}$, $SO_2R^{13}$, lower alkyl, aryl lower alkyl, heteroaryl wherein the ring members include 1 to 3 N atoms and the substituents are halo or amino, heteroaryl lower alkyl wherein heteroaryl is 6-membered and the heteroatoms are N, or aryl lower alkyl substituted with 1 substituent selected from lower alkyl, alkoxy, and halo;

$R^9$ is lower alkyl, aryl lower alkyl, aryl, tetrahydrofuranyl, tetrahydropyranyl, or aryl substituted by 1 to 2 substituents selected from lower alkyl, alkenyl, alkoxy, methylene dioxy, and halo;

$R^{10}$ and $R^{11}$ are each independently aryl, aryl lower alkyl, or aryl substituted by 1 substituent selected from lower alkyl, halo, alkoxy, trifluoromethyl, and pentafluoroethyl;

$R^{12}$ is lower alkyl, aryl, aryl lower alkyl, heteroaryl lower alkyl wherein the heteroatoms are N, a 5- or 6-membered heterocyclic ring containing 1–2 heteroatoms selected from S and N lower alkyl, or aryl substituted with 1 substituent selected from lower alkyl, alkoxy, halo, sulfamoyl, cyano, or phenyl;

$R^{13}$ is lower alkyl, aryl, or aryl substituted with 1 substituent selected from lower alkyl, alkoxy, and halo;

or pharmaceutically acceptable salt thereof.

Most preferred compounds of the invention are represented by the formula:

IIa

[chroman structure with $R^1$, $R^2$, $R^4$, $R^5$, $R^6$, $R^7$]

wherein:

$R^1$ is 6- or 7-OH;

$R^2$ is H or lower alkyl;

$R^4$ and $R^5$ is each methyl; or $R^4$ and $R^5$ taken together are —$(CH_2)_5$—, —$(CH_2)_2$—O—$(CH_2)_2$—, —$(CH_2)_2$ $NR^6$—$(CH_2)_2$—, —$CH_2$—$NR^6$—$(CH_2)_3$—, —$CH_2$—$NR^8$—$(CH_2)_2$—, or —$(CH_2)_2$—$CH(NHR^8)(CH_2)_2$—;

one of $R^6$ and $R^7$ is H and the other is OH or $R^6$ and $R^7$ taken together are =O or —$S(CH_2)_2S$—;

$R^8$ is H, $COOR^9$, $CONHR^{10}$, $CSNHR^{11}$, $COR^{12}$, $SO_2R^{13}$, benzyl, —$CH_2$-Ph-4-F, —$CH_2$-pH-4-$OCH_3$, —$CH_2$-4-Py, n-butyl, —$CH_2$-c-propyl,

[pyrimidine structures and quinoxaline structure]

$R^9$ is i-propyl, phenyl, phenethyl, t-butyl,

[styryl, benzodioxole, tetrahydrofuran structures]

$R^{10}$ is phenyl, p-chlorophenyl, or p-trifluoromethylphenyl;

$R^{11}$ is phenyl, benzyl, or 1-naphthyl;

$R^{12}$ is

[various substituent structures: cyanophenyl, hydantoin, dihydropyrimidinone, indolylmethyl, thiazolidinone, imidazolylmethyl, benzyl, biphenylmethyl, pyridyl, or sulfamoylphenyl]; and $R^{13}$ is 1- or 2-naphthyl, phenyl, 4-chlorophenyl, 4-methylphenyl, 4-t-butylphenyl, n-butyl, or i-propyl;

or a pharmaceutically acceptable salt thereof.

Most preferred compounds of the invention are also represented by the formula:

IIa wherein:
R¹ is 6- or 7-OH when R² is H;
R¹ is 7-OH when R² is CH₃;
R⁴ and R⁵ is each methyl; or R⁴ and R⁵ taken together are
—(CH₂)₅—, —(CH₂)₂—O—(CH₂)₂—, —(CH₂)₂—
NR⁸—(CH₂)₂—, —CH₂—NR⁸—(CH₂)₃—, —CH₂—
NR⁸—(CH₂)₂—, or —(CH₂)₂—CH(NHR⁸)(CH₂)₂—;
one of R⁶ and R⁷ is H and the other is OH or R⁶ and R⁷
taken together are =O or —S(CH₂)₂S—; and -continued

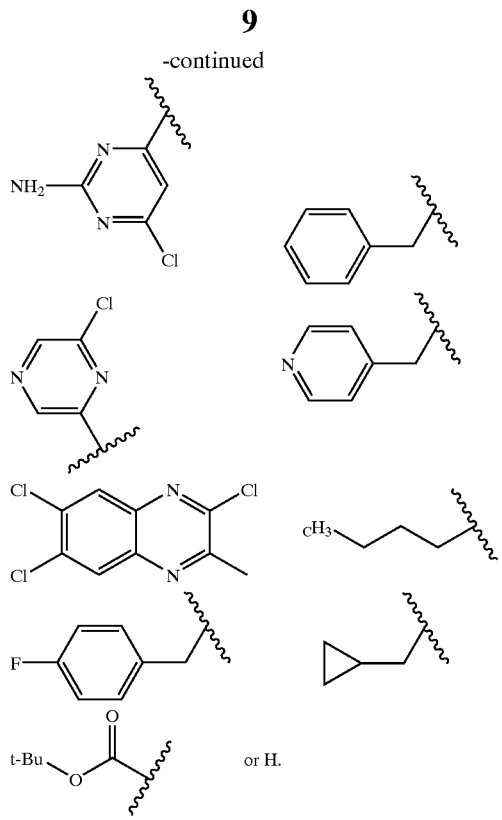

or H.

Most preferred compounds of the invention are represented by the formula:

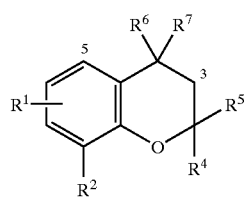
IIa wherein:

$R^1$ is 6- or 7-OCH$_2$C(O)NH(CH$_2$)$_{1-5}$R$^{17}$, or 6- or 7-OCH$_2$-4-Phe-C(O)NH(CH$_2$)$_{1-6}$R$^{17}$ when $R^2$ is H;

$R^1$ is 7-OCH$_2$C(O)NH(CH$_2$)$_{1-6}$R$^{17}$, or 7-OCH$_2$-4-Phe-C(O)NH(CH$_2$)$_{1-6}$R$^{17}$ when $R^2$ is CH$_3$;

$R^4$ and $R^5$ is each methyl; or $R^4$ and $R^5$ taken together are —(CH$_2$)$_5$—, —(CH$_2$)$_2$—O—(CH$_2$)$_2$—, —(CH$_2$)$_2$NR$^8$—(CH$_2$)$_2$—, —(CH$_2$)$_2$—CH(NHR$^8$)(CH$_2$)$_2$—, —(CH$_2$)$_2$—S—(CH$_2$)$_2$—, or —CH$_2$CH(NCH$_3$)(CH$_2$)$_2$CHCH$_2$—;

or $R^4$ is methyl and $R^5$ is CH$_2$OCH$_3$ or —(CH$_2$)$_3$N(Et)$_2$;

one of $R^6$ and $R^7$ is H and the other is OH; or $R^6$ and $R^7$ taken together are =O or —S(CH$_2$)$_2$S—; or one of $R^6$ and $R^7$ is H and the other is NAB, where A is methyl, 2-methoxyethyl, 2-phenylethyl, 4-methoxybenzyl, 2-tetrahydro-furanylmethyl, 2(3,4-dimethoxyphenyl)ethyl, or 2,2-diphenylethyl and B is H, 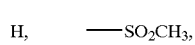 —SO$_2$CH$_3$, 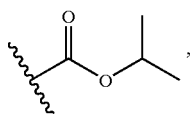

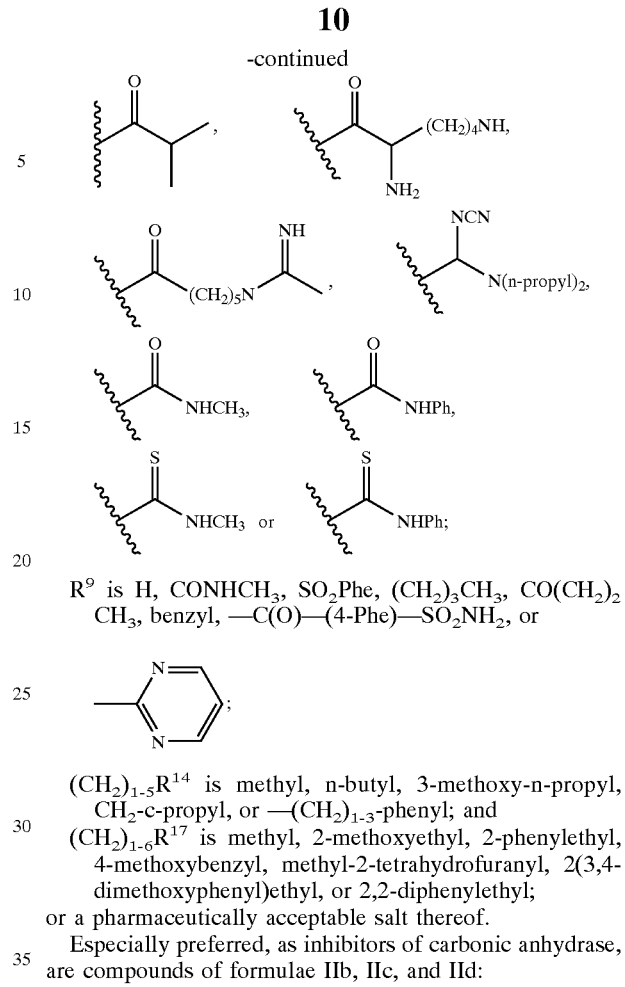

$R^9$ is H, CONHCH$_3$, SO$_2$Phe, (CH$_2$)$_3$CH$_3$, CO(CH$_2$)$_2$CH$_3$, benzyl, —C(O)—(4-Phe)—SO$_2$NH$_2$, or

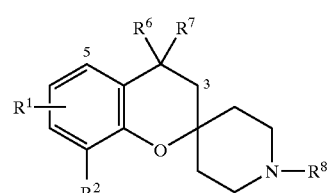

(CH$_2$)$_{1-5}$R$^{14}$ is methyl, n-butyl, 3-methoxy-n-propyl, CH$_2$-c-propyl, or —(CH$_2$)$_{1-3}$-phenyl; and (CH$_2$)$_{1-6}$R$^{17}$ is methyl, 2-methoxyethyl, 2-phenylethyl, 4-methoxybenzyl, methyl-2-tetrahydrofuranyl, 2(3,4-dimethoxyphenyl)ethyl, or 2,2-diphenylethyl;

or a pharmaceutically acceptable salt thereof.

Especially preferred, as inhibitors of carbonic anhydrase, are compounds of formulae IIb, IIc, and IId:

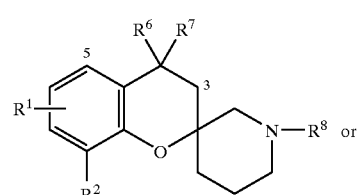
IIb

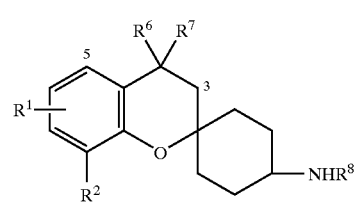
IIc

IId wherein:

$R^1$ is 6- or 7-OH, 6- or 7-OCH$_2$C(O)NH(CH$_2$)$_{1-6}$R$^{17}$, or 6- or 7-OCH$_2$-4-Phe-C(O)NH(CH$_2$)$_{1-6}$R$^{17}$;

$R^2$ is H or CH$_3$;

$R^8$ is —CO-Phe-p-SO$_2$NH$_2$; and $R^6$ and $R^7$ together are =O or —SCH$_2$CH$_2$S—.

Most preferred of these are the following compounds:
|  | Formula IIb | Formula IIc |  | Formula IId |  |
|---|---|---|---|---|---|
| $R^1$ | 7-OH | 6-OH | 6-OH | 6-OH | 7-OH |
| $R^2$ | H | H | H | H | $CH_3$ |
| $R^6/R^7$ | —O— | —$SCH_2CH_2S$— | —O— | —$SCH_2CH_2S$— | —$SCH_2CH_2S$— |
$R^{14}$ and $R^{17}$ may each be any pharmacologically relevant organic radical, such as those derived by removal of $H_2NCH_2$— from the following compounds:
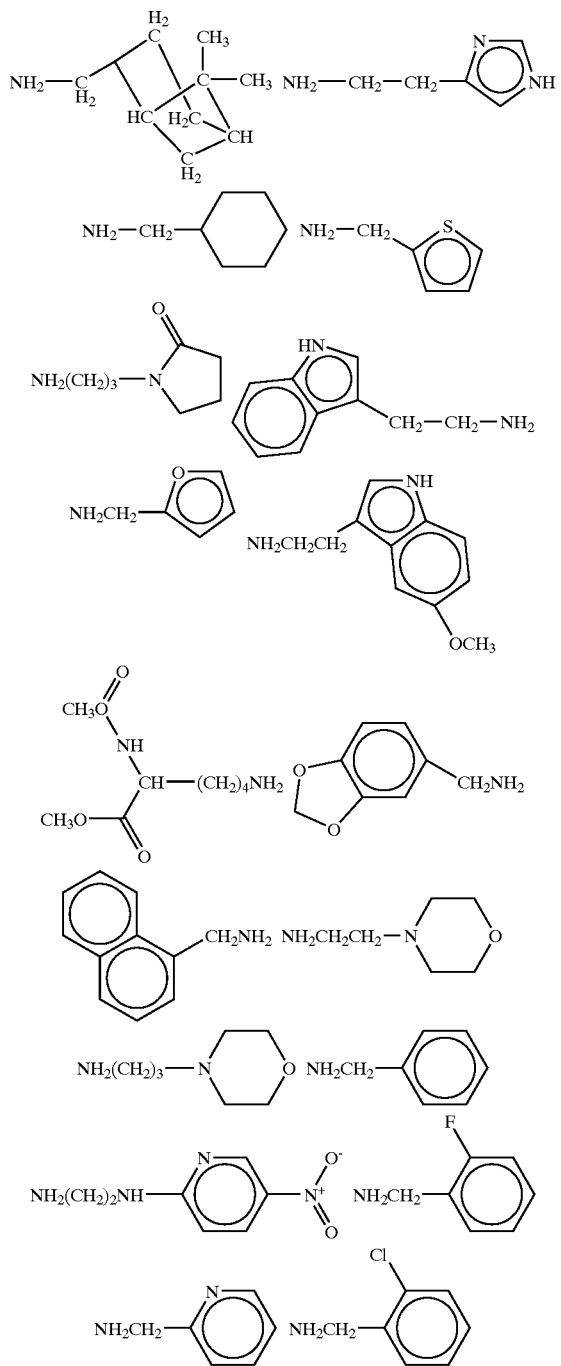
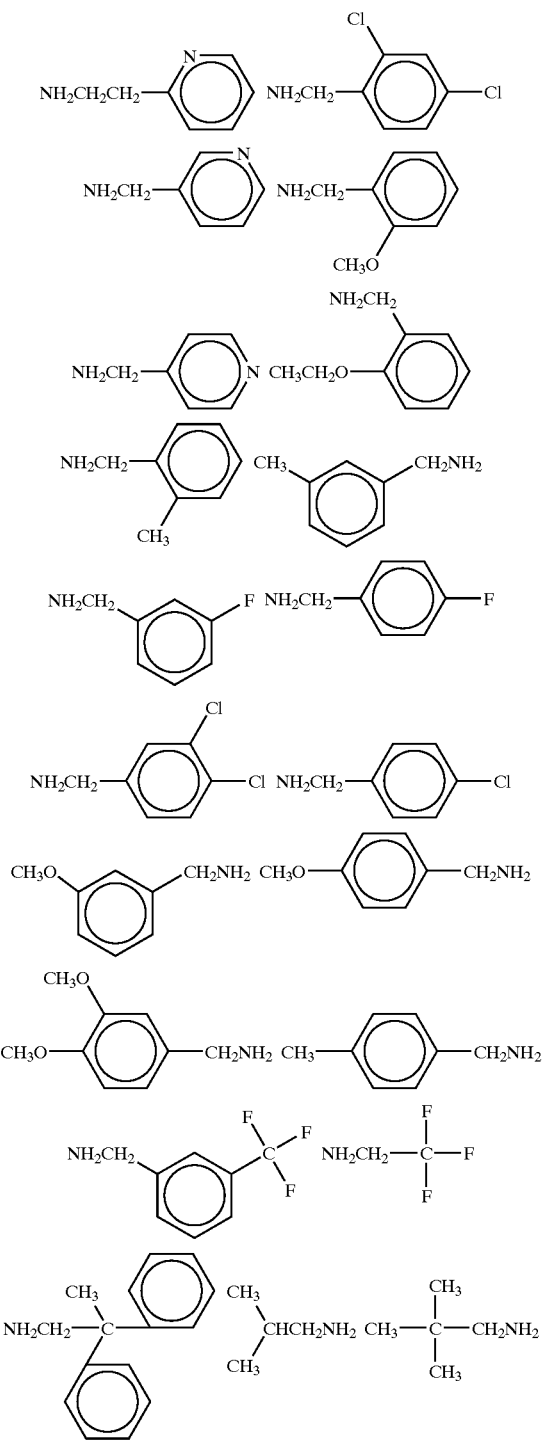

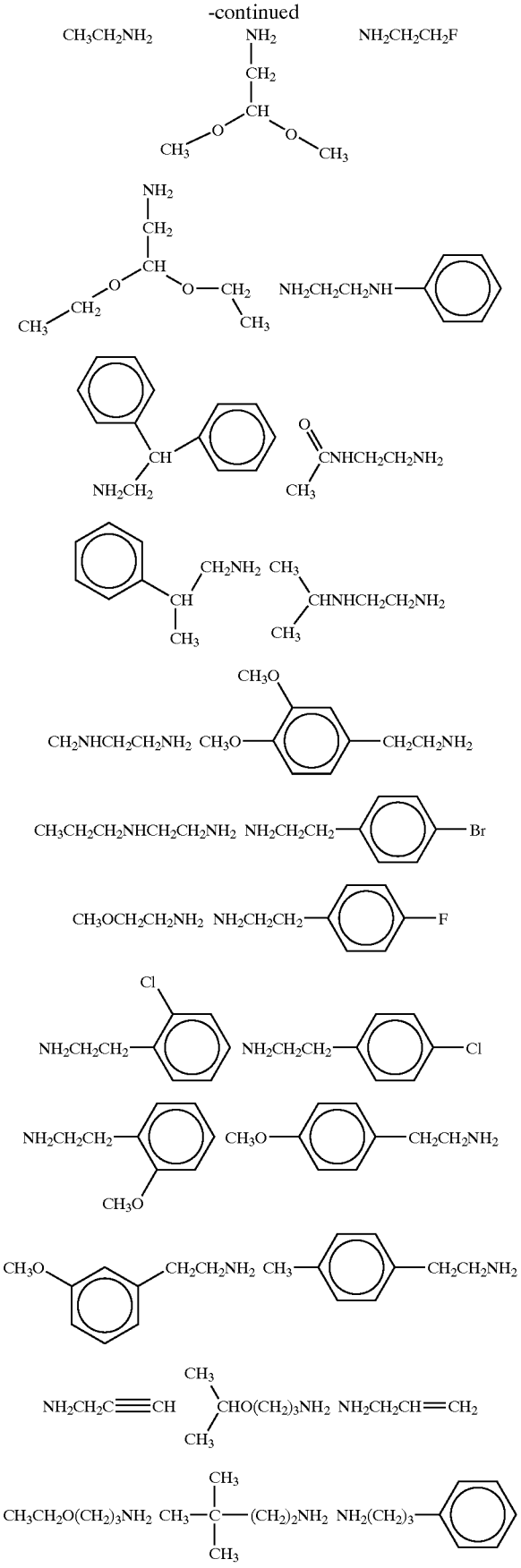
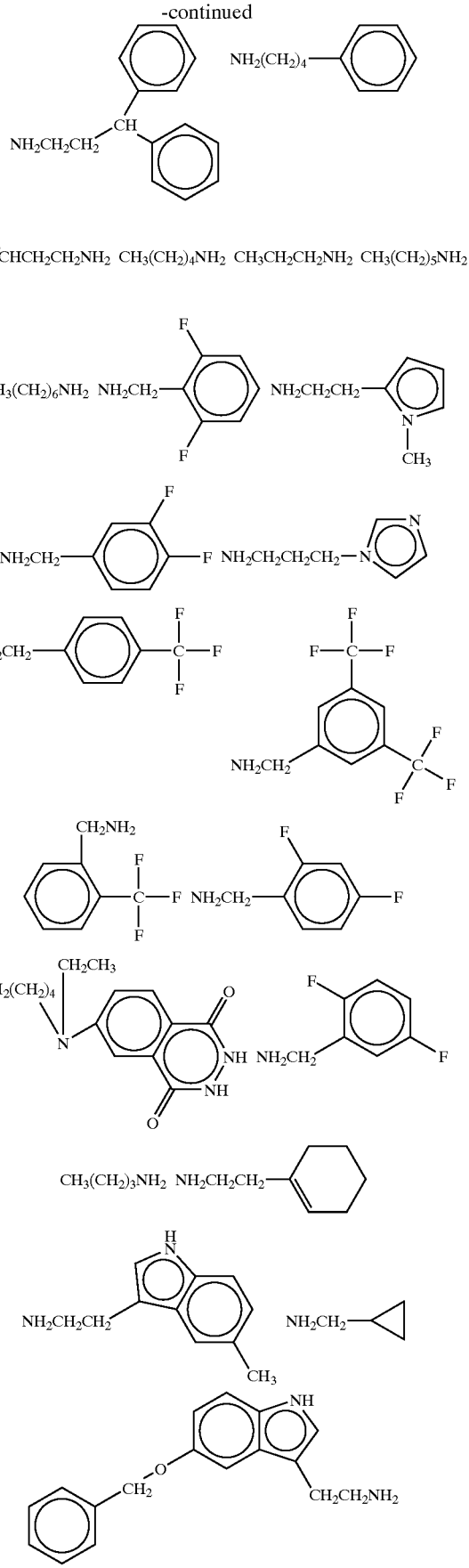

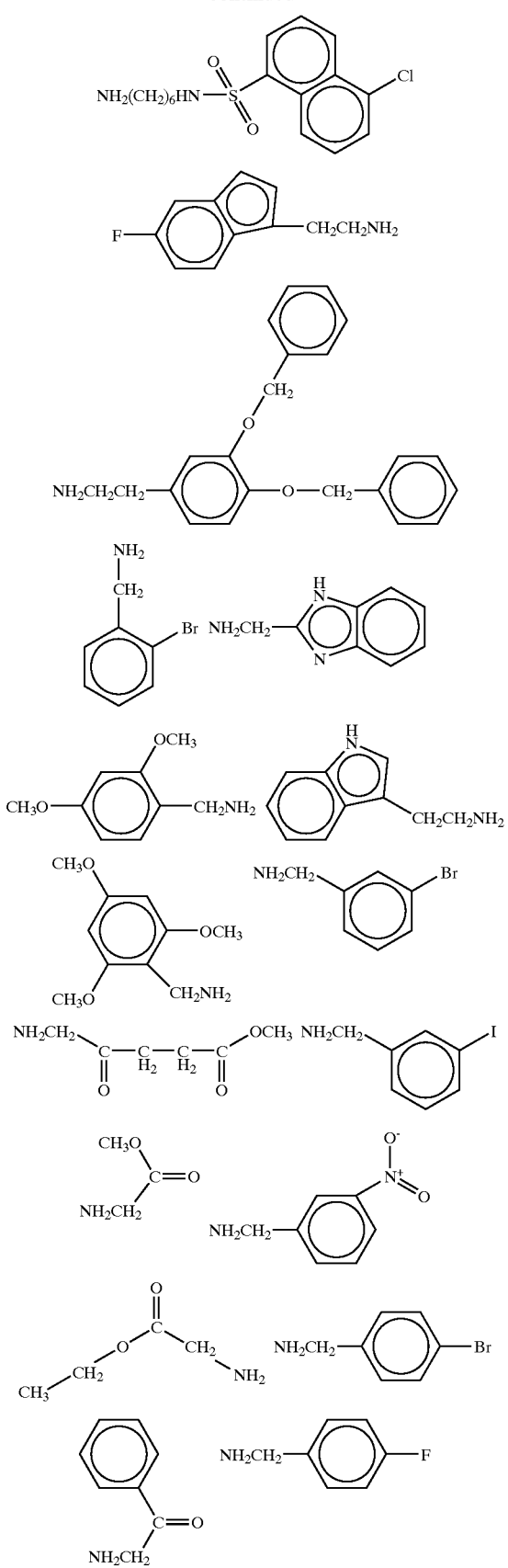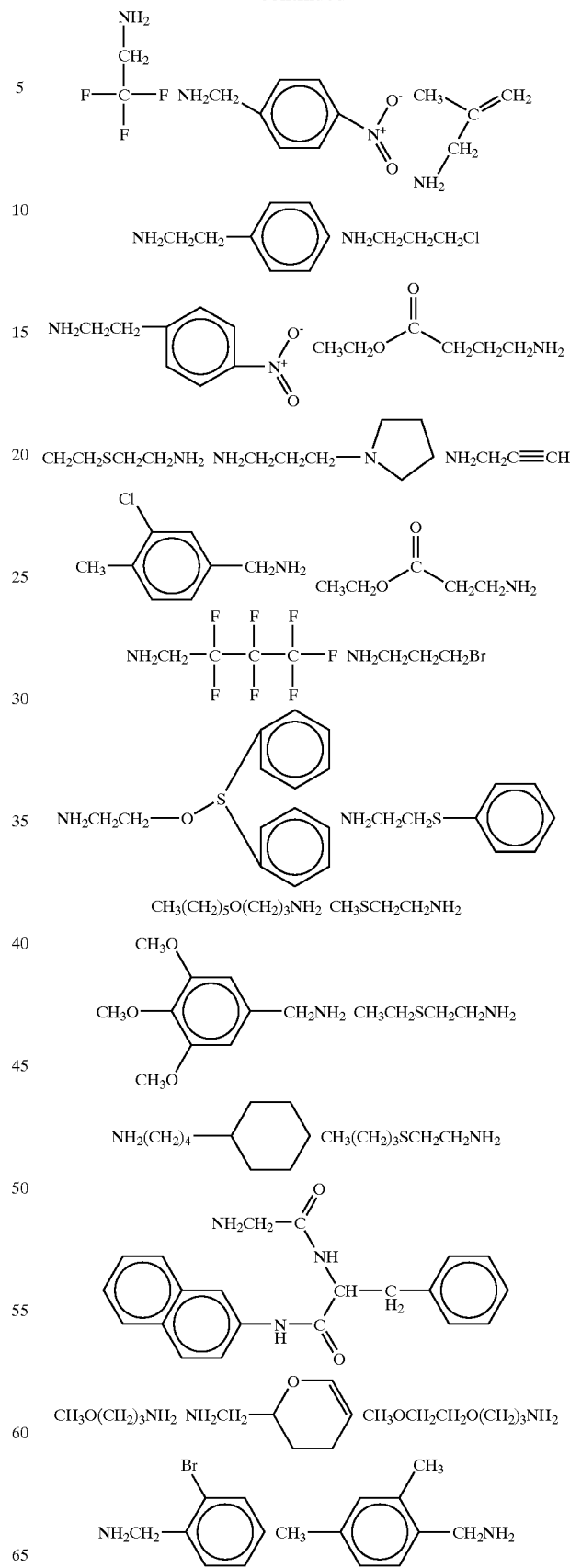

-continued
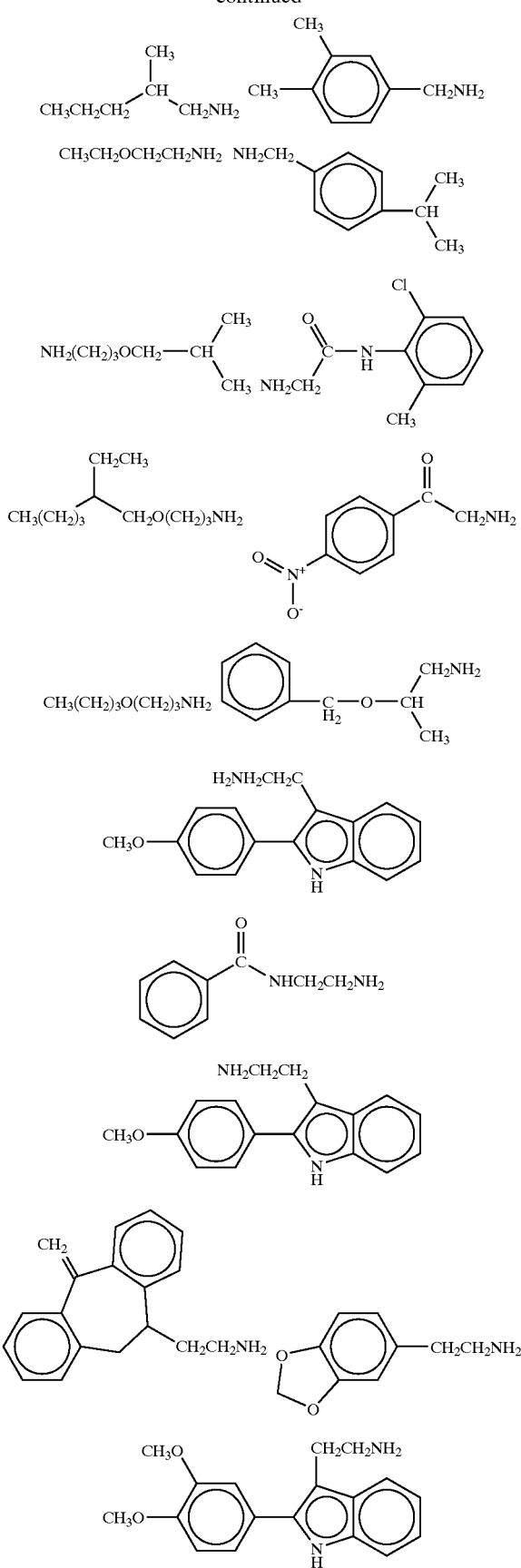
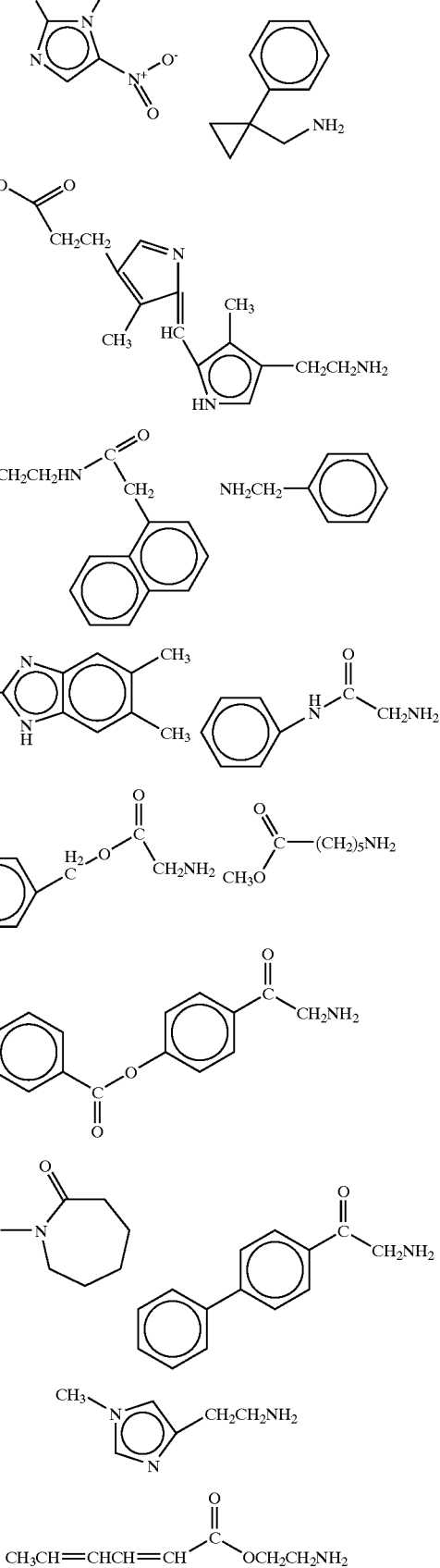

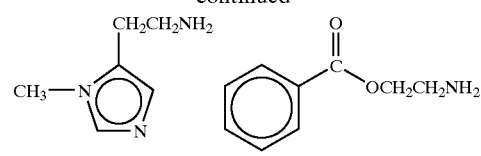
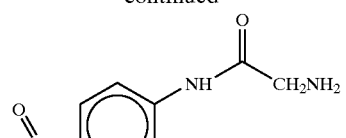
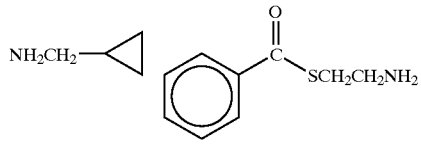
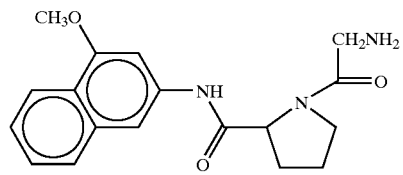
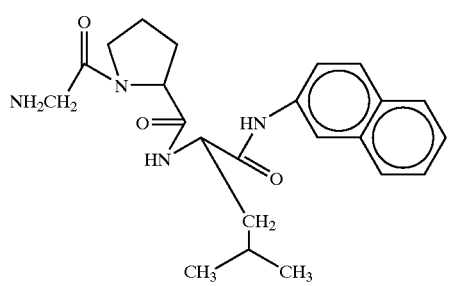
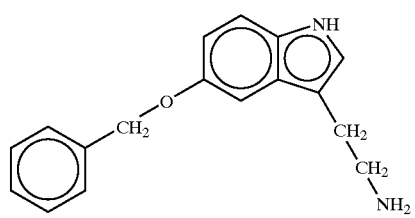
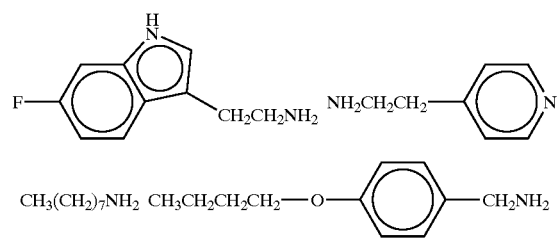
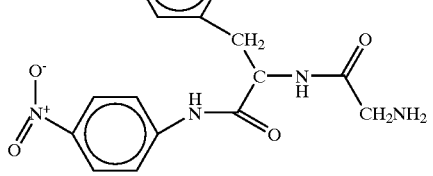
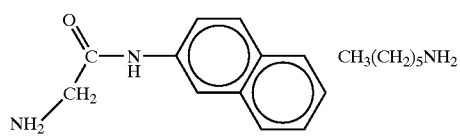
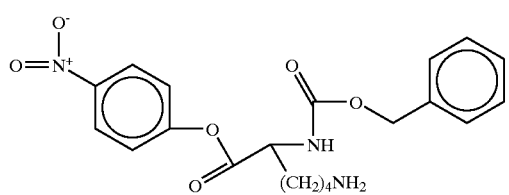
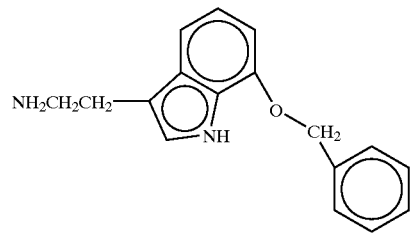
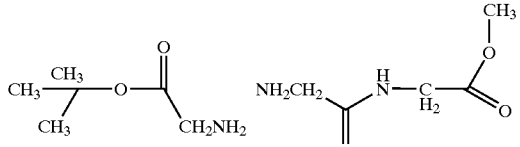
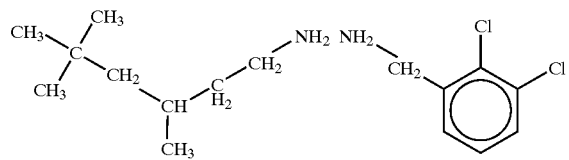
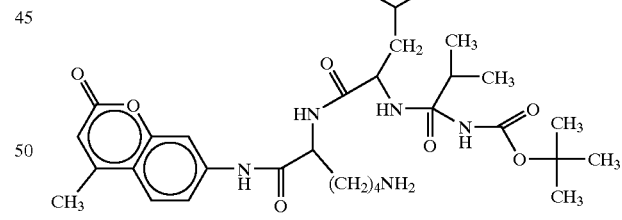
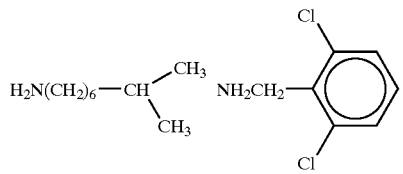
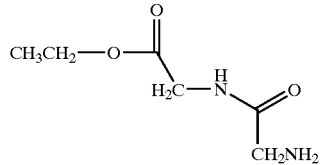
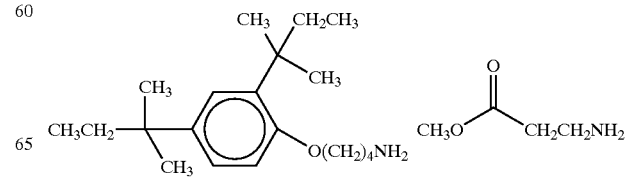

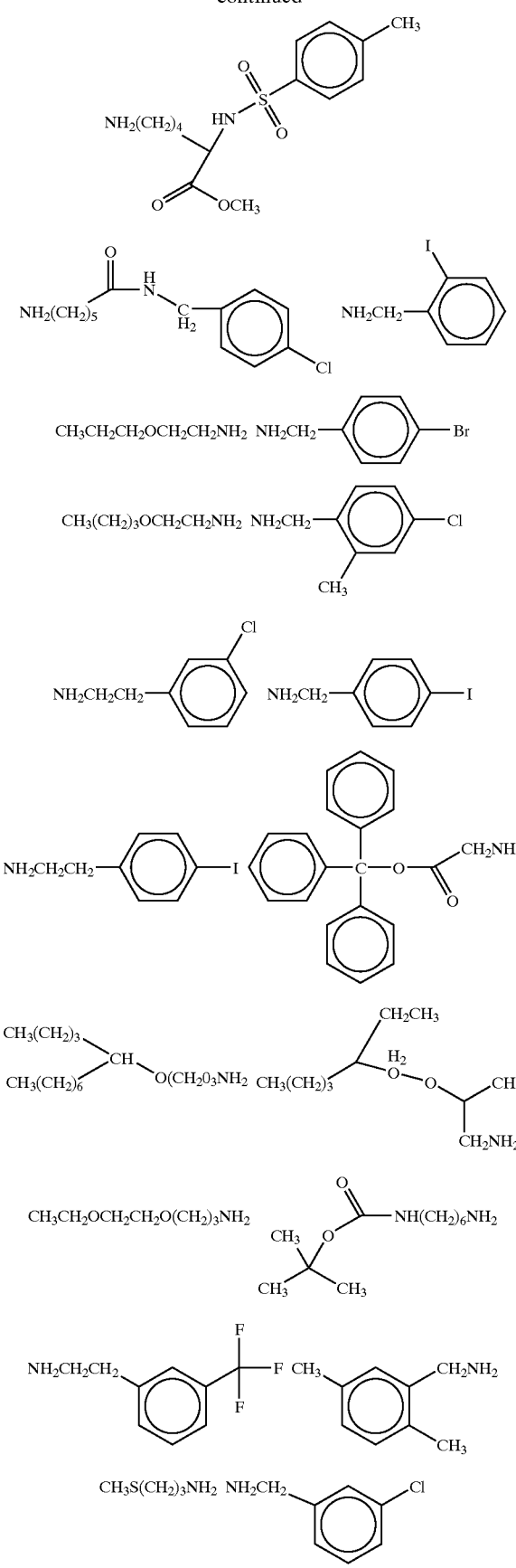
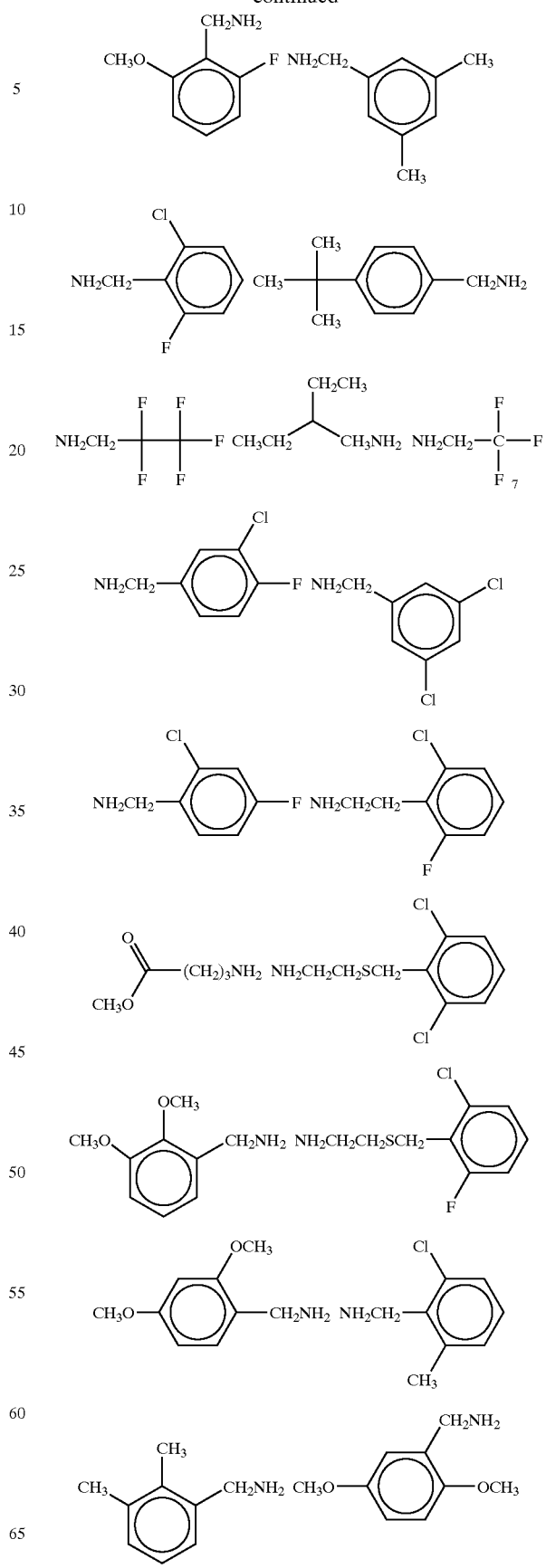

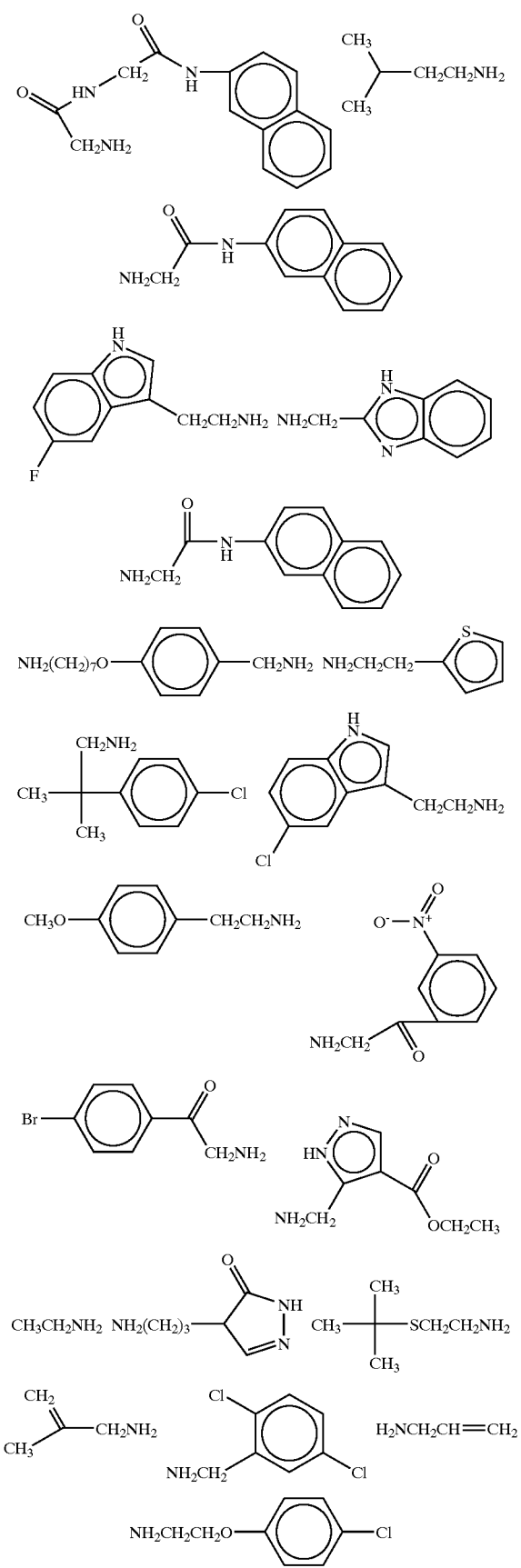
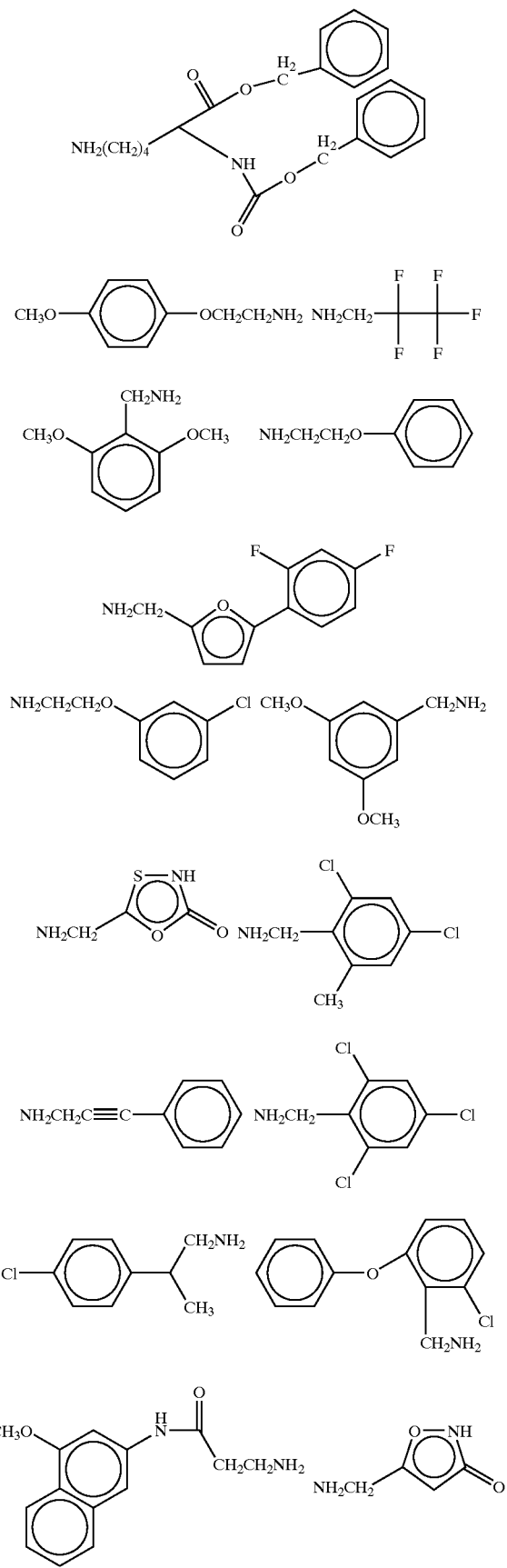

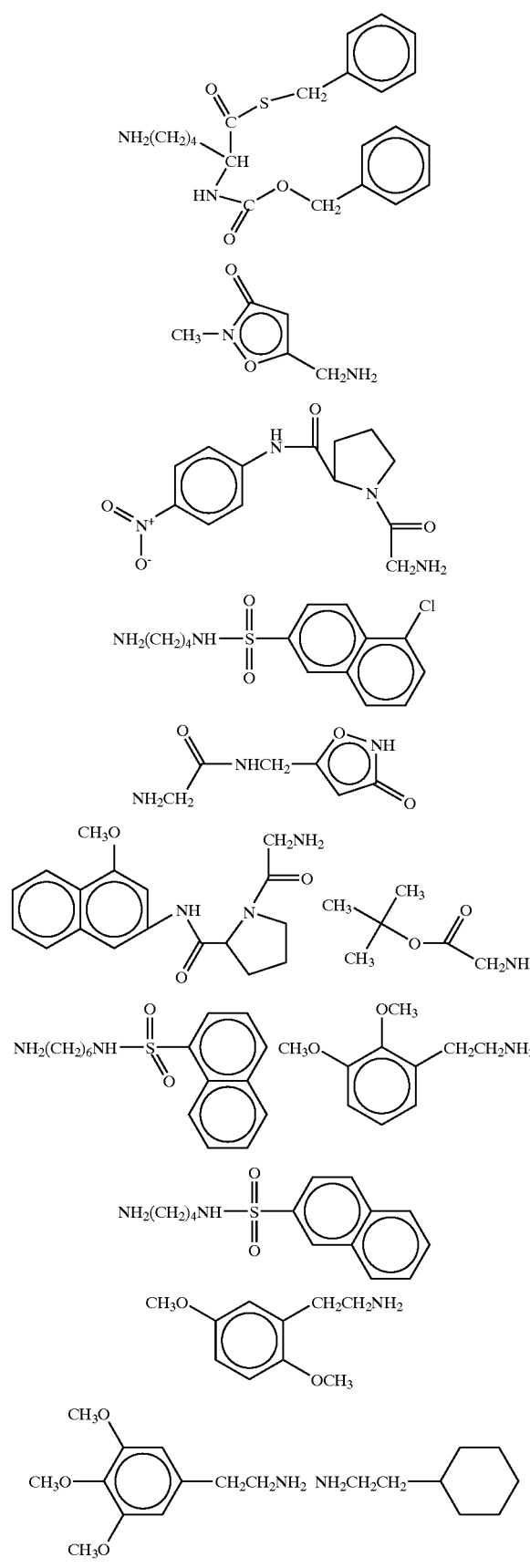
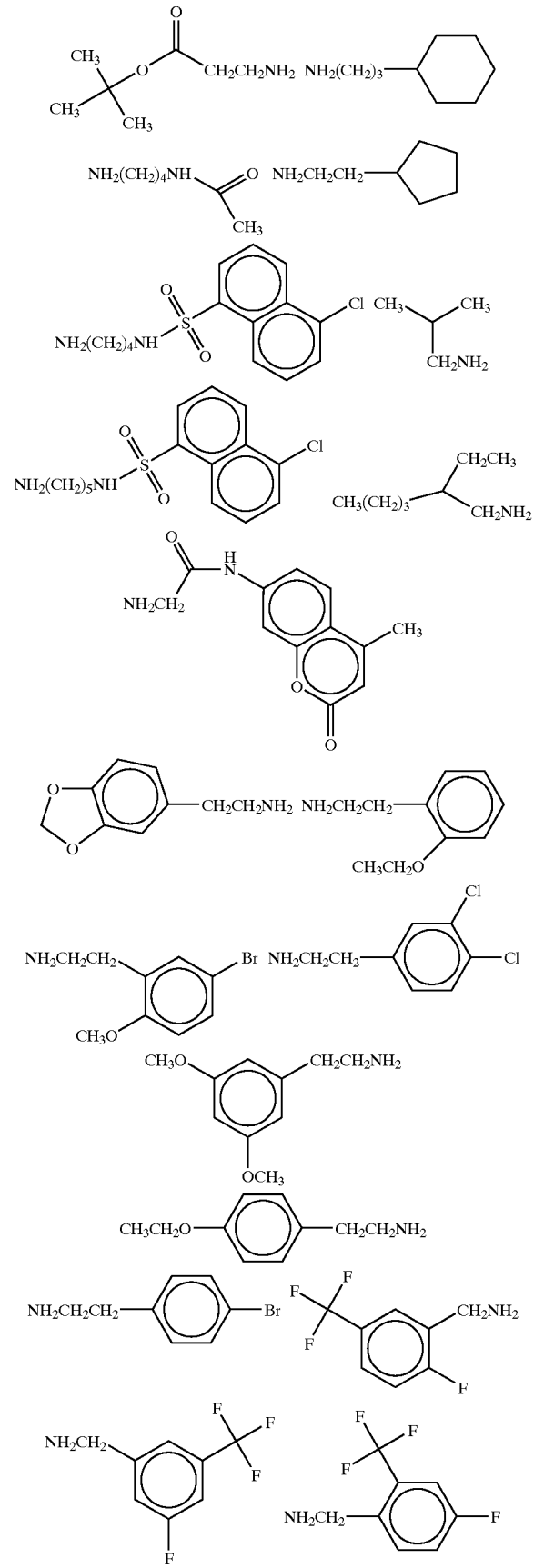

-continued

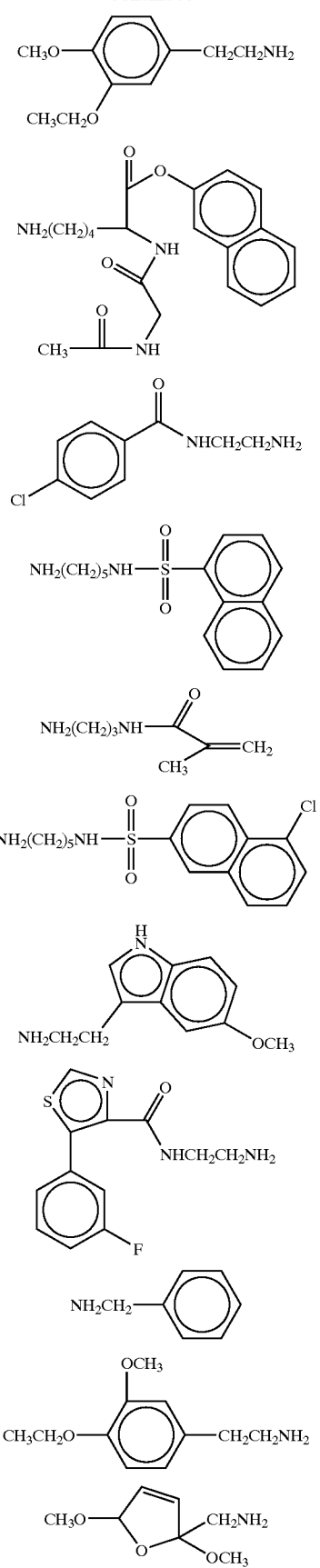
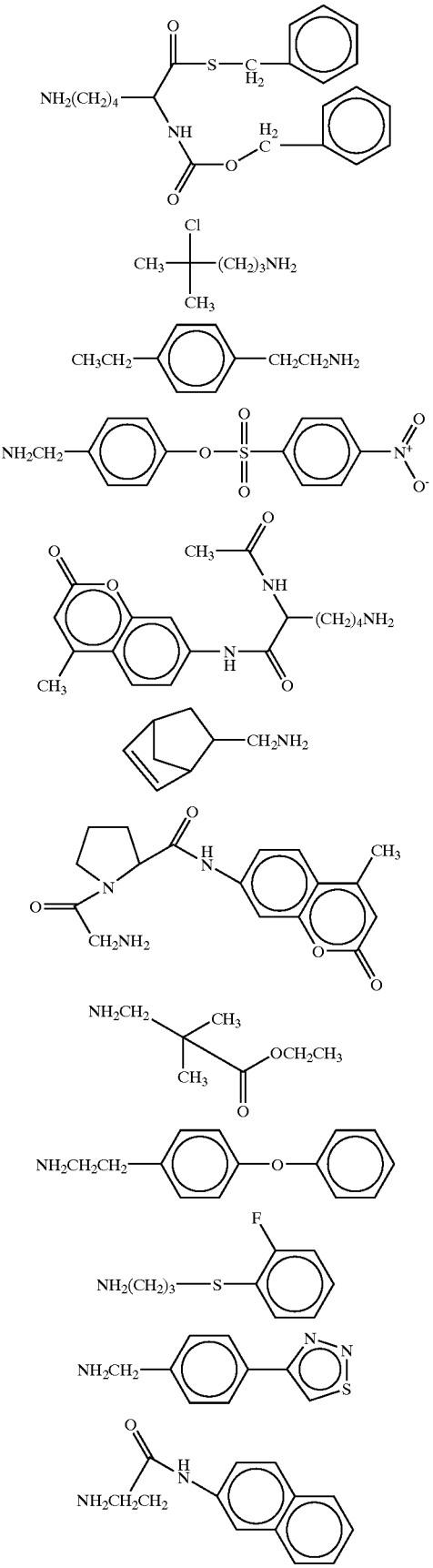

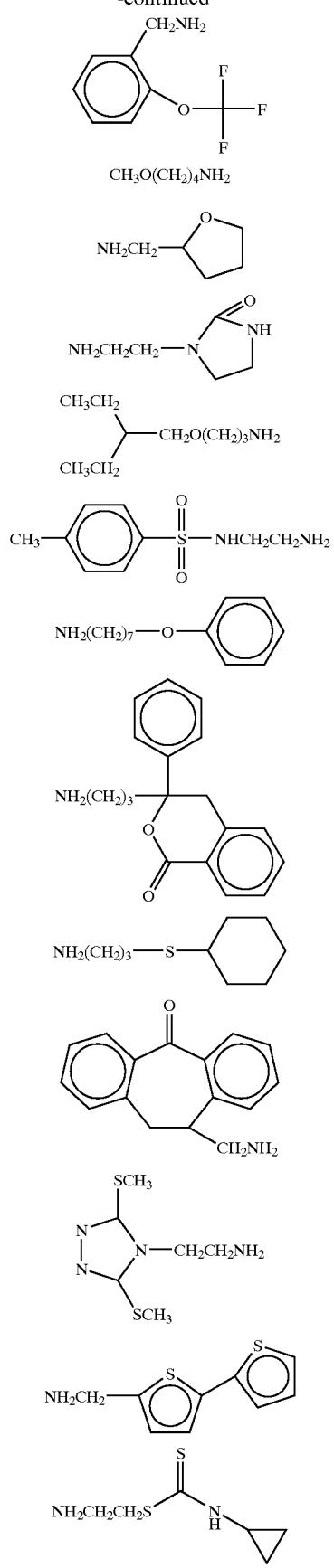
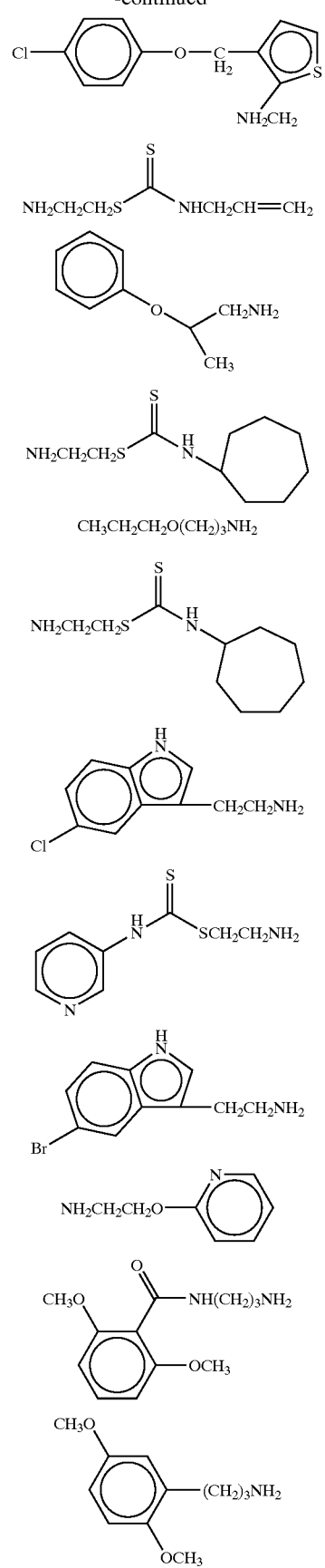

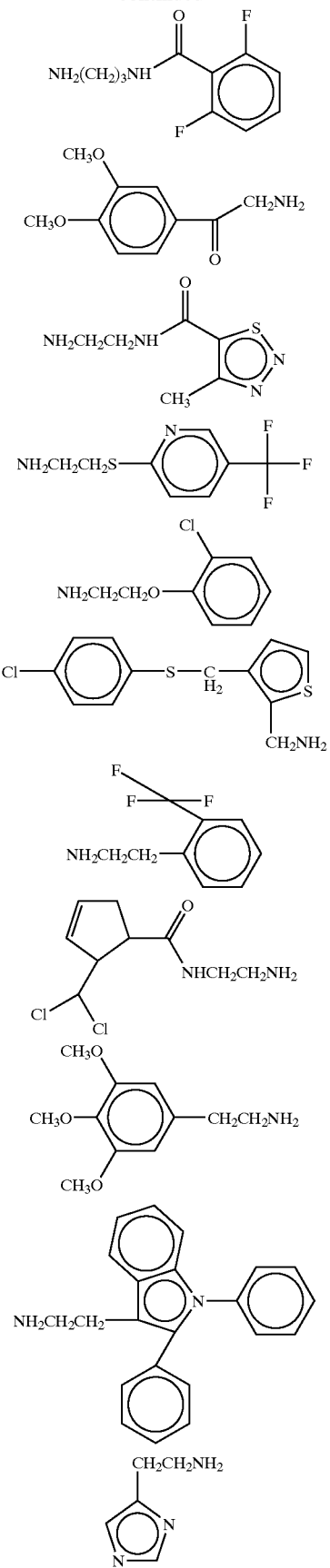
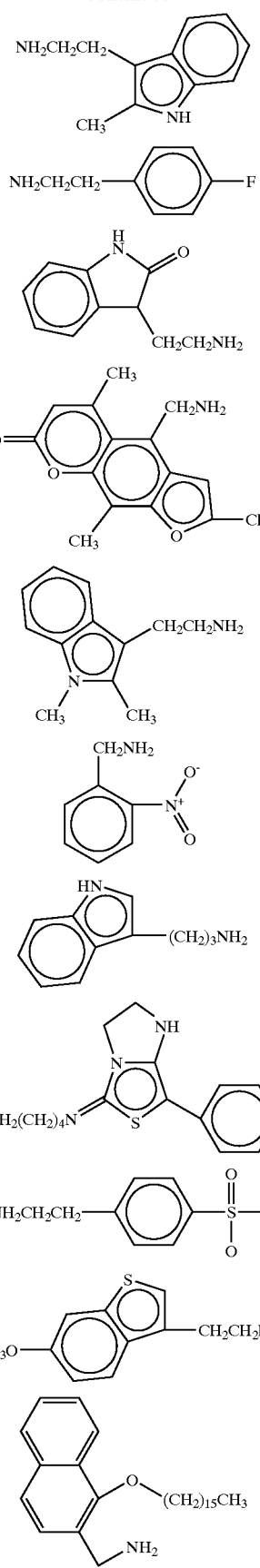

-continued
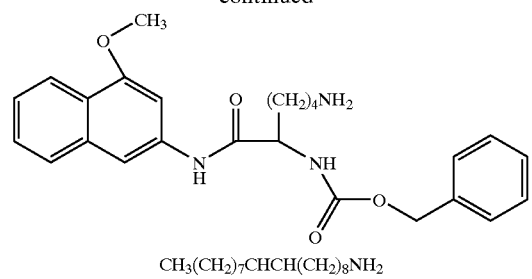
CH₃(CH₂)₇CHCH(CH₂)₈NH₂
CH₃(CH₂)₉NH₂
CH₃(CH₂)₁₂NH₂
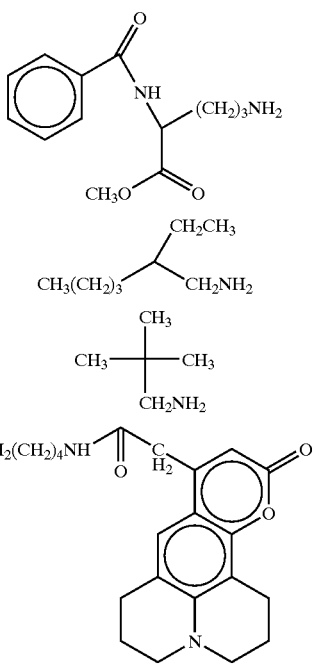
CH₃(CH₂)₁₅NH₂
CH₃(CH₂)₁₇NH₂
-continued
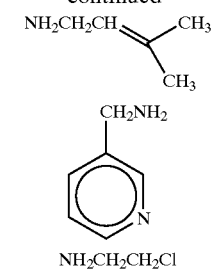
NH₂CH₂CH₂Cl
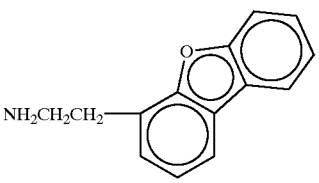
CH₃(CH₂)₃CHCH₂NH₂ (with CH₂CH₃ branch)
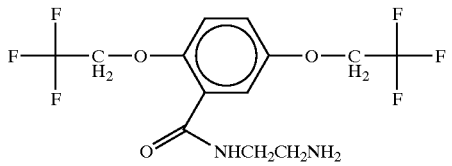
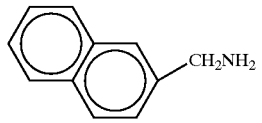
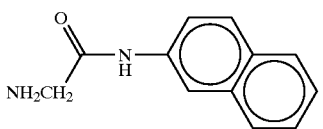
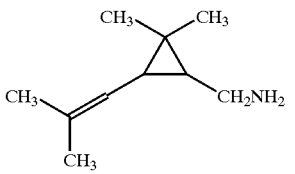

-continued
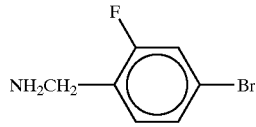
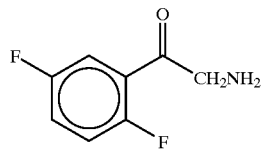
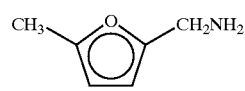
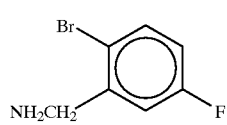
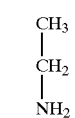
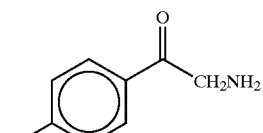
CH₃(CH₂)₃NH₂
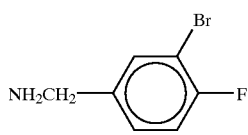
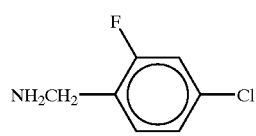
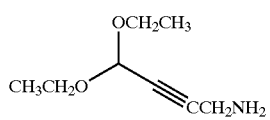
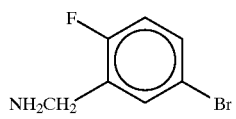
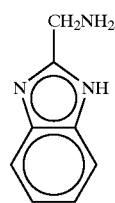
-continued
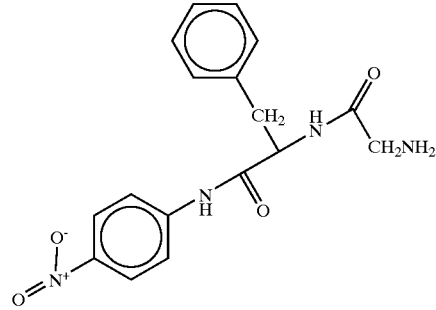
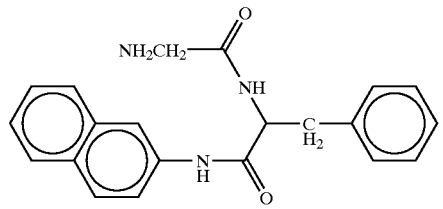
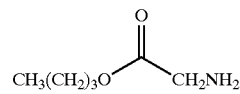
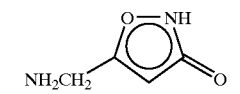
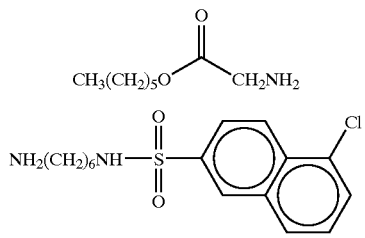
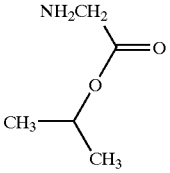
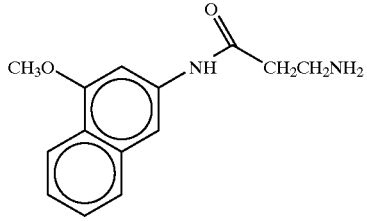
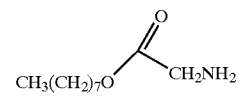
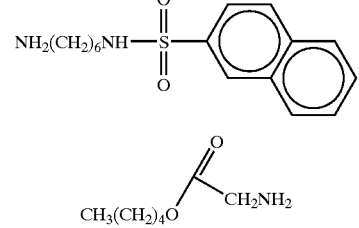

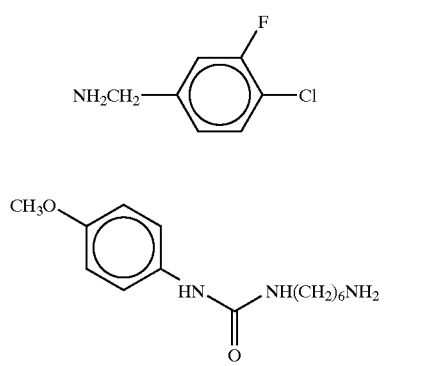
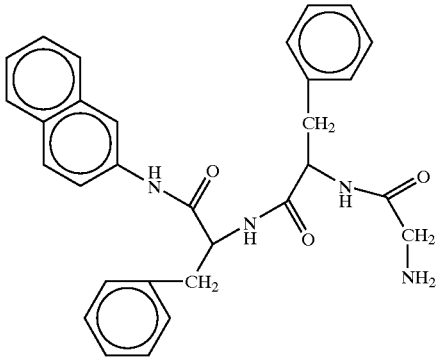
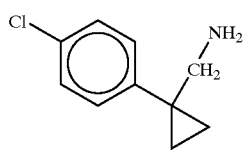
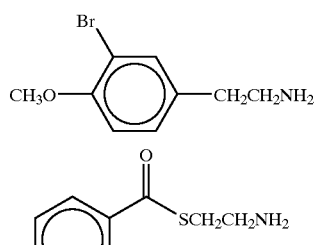
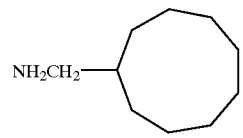
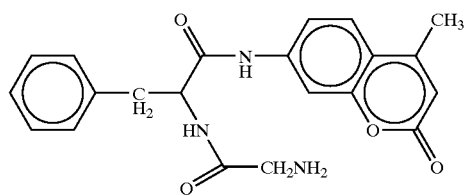
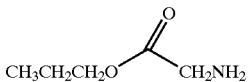
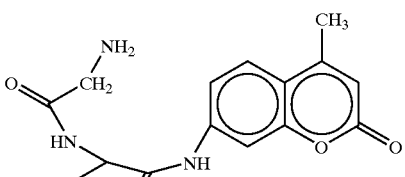
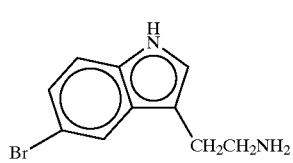

-continued

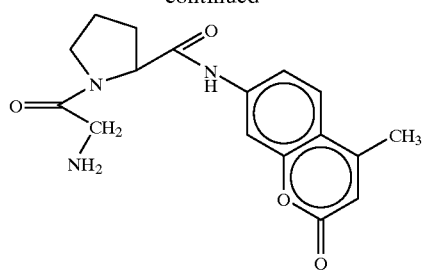
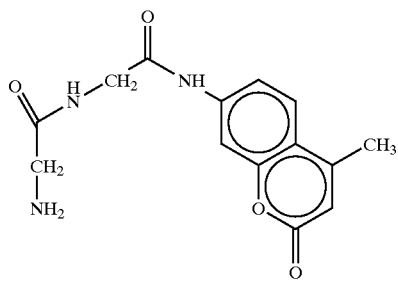
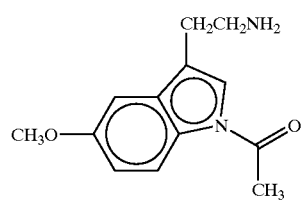
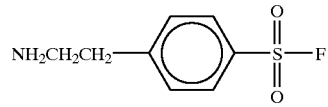
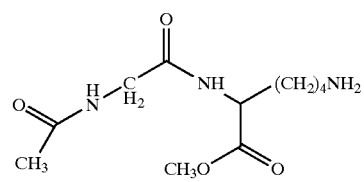
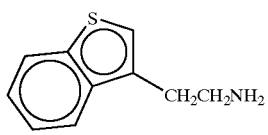
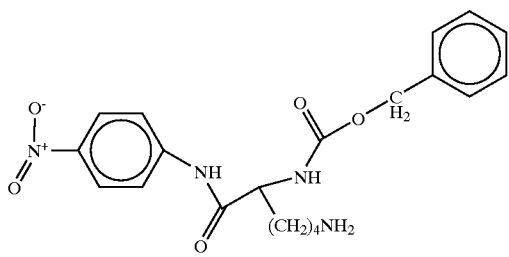

-continued

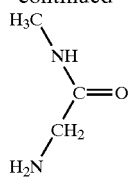
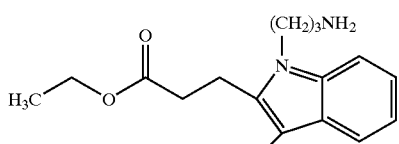
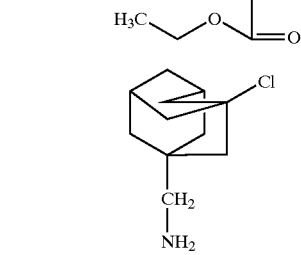
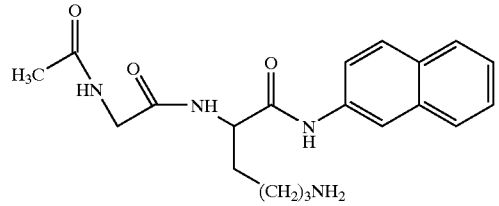
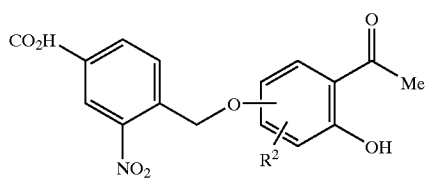

One embodiment of the invention is the use of the combinatorial library of Formula I in assays to discover biologically active compounds (ligands) of Formula II. Thus, an aspect of the invention is a method of identifying a compound having a desired characteristic which comprises synthesizing a combinatorial library of Formula I and testing the compounds of Formula I and the ligands of Formula II, either attached to the solid support or detached therefrom, in an assay which identifies compounds having the desired characteristic. A further embodiment of the invention is determining the structure of any compound so identified.

Another embodiment of the invention is a process for preparing a compound of the formula:

3

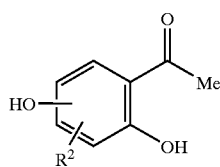

where $R^2$ is H or lower alkyl, which comprises a) reacting allyl or methyl 4-(hydroxymethyl)-3-nitrobenzoate with a compound of the formula:

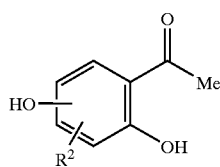

in the presence of triphenylphosphine, toluene, and DEAD and stirring the mixture at room temperature to produce

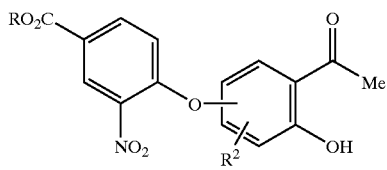

where R is allyl or methyl, and b) when R is allyl reacting said compound with methylene chloride, tetrakistriphenylphosphine palladium(0), and pyrrolidine and stirring the mixture at 0° C., or when R is methyl reacting said compound with dilute NaOH and THF and stirring the mixture at 0° C.

For this reaction, R=allyl is preferable to the t-butyl or methyl esters since the milder conditions would not induce aldol type condensation of the acetophenone portion of the molecule.

Another embodiment of the invention is a method for identifying compounds that are inhibitors of carbonic anhydrase which comprises preparing a mixture of 20–300 pmol test compound and aqueous solutions (total volume; 25–100, preferably about 50, $\mu$L) of 0.03–0.12, preferably about 0.06, $\mu$M carbonic anhydrase and 0.04–0.16, preferably about 0.08, $\mu$M dansylamide, exposing said mixture to U.V. (preferably 274 nm) light, and determining the amount of emitted U.V. (preferably 454 nm, light.

Another embodiment of the invention is a method for identifying compounds that are enzyme inhibitors which is a lawn assay which comprises contacting a colloidal matrix containing enzyme, which matrix has embedded therein a mono-layer of solid supports with attached ligands, with a layer of fluorogenic substrate-containing material, eluting said ligands by exposure to U.V. light, and detecting zones of inhibition in the colloidal matrix produced thereby. A preferred such lawn assay comprises contacting an agarose matrix containing bovine carbonic anhydrase with a fluorescein diacetate-containing layer of agarose.

Another embodiment of the invention is a compound of the formula:

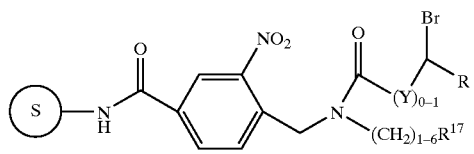

wherein:

Ⓢ is a solid support;

R is H or alkyl;

$R^{16}$ is lower alkyl, substituted lower alkyl, aryl, or substituted aryl;

$R^{17}$ is H; alkyl substituted by 1–3 alkoxy, S-loweralkyl, sulfamoyl, halo, alkylsulphonamido, or arylsulphonamido; alkenyl; alkynyl; aryl; substituted aryl; heteroaryl; substituted heteroaryl; heterocycloalkyl; —$CH_2NR^{16}C(O)R^{16}$; —$C(O)NR^{16}R^{16}$; —$CH_2OC(O)R^{16}$; OR—$CH_2SC(O)R^{16}$; and Y is aryl or heteroaryl.

Compounds of formula 14 are useful as intermediates in the construction of combinatorial libraries and are especially useful in automated or batch mode syntheses thereof.

Definitions

The following abbreviations have the indicated meaning:

| | |
|---|---|
| Boc = | t-butyloxycarbonyl |
| c- = | cyclo |
| DEAD = | diethylazodicarboxylate |
| DBU = | 1,8-diazabicyclo[5,4,0]undec-7-ene |
| DCM = | dichloromethane = methylene chloride |
| DIC = | diisopropylcarbodiimide |
| DMAP = | 4-N,N-dimethylaminopyridine |
| DMF = | N,N-dimethylformamide |
| DMSO = | dimethyl sulfoxide |
| DVB = | 1,4-divinylbenzene |
| EDT = | 1,2-ethanedithiol |
| equiv. = | equivalent |
| Et = | ethyl |
| FACS = | fluorescence activated cell sorting |
| Fmoc = | 9-fluorenylmethoxycarbonyl |
| GC = | gas chromatography |
| HOBt = | N-hydroxybenzotriazole |
| hr = | hour, hours |
| im = | imidazole |
| in = | indole |
| m- = | meta |
| Me = | methyl |
| Mtr = | 4-methoxy-2,3,6-trimethylbenzenesulfonyl |
| n- = | normal |
| Naph = | naphthyl |
| p- = | para |
| PEG = | polyethylene glycol |
| Ph = | phenyl |
| Phe = | phenylene |
| Pmc = | 2,2,5,7,8-pentamethylchroman-6-sulfamoyl |
| Py = | pyridyl |
| r.t. = | room temperature |
| sat'd = | saturated |
| s- = | secondary |
| t- = | tertiary |
| t-Boc = | t-butyloxycarbonyl |
| TFA = | trifluoroacetic acid |
| THF = | tetrahydrofuran |

"Alkyl" is intended to include linear, branched, or cyclic structures and combinations thereof of from 1 to 20 carbon atoms. "Lower alkyl" includes alkyl groups of from 1 to 8 carbon atoms. Examples of lower alkyl groups include methyl, ethyl, propyl, isopropyl, butyl, s- and t-butyl, pentyl, hexyl, octyl, c-propyl, c-butyl and the like. "Lower cycloalkyl" includes cycloalkyl groups of from 3 to 8 carbon atoms. Examples of lower cycloalkyl groups include c-propyl, c-butyl, c-pentyl, 2-methylcyclopropyl, cyclopropylmethyl, and the like.

"Alkenyl" is $C_2$–$C_6$ alkenyl of a linear, branched, or cyclic ($C_5$–$C_6$) configuration and combinations thereof. Examples of alkenyl groups include allyl, isopropenyl, pentenyl, hexenyl, c-hexenyl, 1-propenyl, 2-butenyl, 2-methyl-2-butenyl, and the like.

"Alkynyl" is $C_2$–$C_6$ alkynyl of a linear, branched, or cyclic ($C_5$–$C_6$) configuration and combinations thereof. Examples of alkynyl groups include ethynyl, propargyl, 3-methyl-1-pentynyl, 2-heptynyl, isopropynyl, pentynyl, hexynyl, c-hexynyl, 1-propynyl, 2-butynyl, 2-methyl-2-butynyl, and the like.

"Alkoxy" mens alkoxy groups of from 1 to 6 carbon atoms of a straight, branched, or cyclic configuration. Examples of alkoxy groups include methoxy, ethoxy, propoxy, isopropoxy, cyclopropyloxy, cyclohexyloxy, and the like.

"Substituted loweralkyl" means lower alkyl substituted with 1–3 alkoxy, carboalkoxy, carboxamido, di-loweralkylamino, aryl, substituted aryl, heteroaryl.

"Aryl" means phenyl or naphthyl.

"Substituted aryl" means aryl substituted with 1–3 halo, loweralkyl alkoxy, aryl, S-loweralkyl, alkylsulphonamido, arylsulphonamido, or sulfamoyl. "Heteroaryl" means a 5 or 6 membered aromatic ring containing 1–3 hetero atoms selected from C, N, and S.

"Substituted heteroaryl" means heteroaryl substituted with 1–3 halo, loweralkyl, alkoxy, aryl, S-loweralkyl, alkylsulphonamido, arylsulphonamido, or sulfamoyl.

"Heterocycloalkyl" means lower cycloalkyl containing 1–3 hetero atoms selected from O, N, and S.

Halogen includes F, Cl, Br, and I.

L and L' are depicted in Table 1, which also shows cleavage reagents. In designing a synthetic scheme, L and L' are chosen such that they are orthogonally reactive; i.e., they must allow for removal of either T or II( where T=T'—OH) without removal of the other since simultaneous cleavage of both T and II from the solid support is disadvantageous. In the structures as shown, the left-hand bond is the point of attachment to the solid support and the right-hand bond is the point of attachment to either T or II.

TABLE 1

LINKER GROUPS

| LINKER GROUP | CLEAVAGE REAGENT |
|---|---|
| 1. (nitro-benzyl with NO$_2$, —CH$_2$B—) or (nitro-benzyl with NO$_2$, —CH$_2$O—C(O)—B—) | hv |
| 2. (O$_2$N-aryl-CH$_2$O—) | hv |
| 3. (aryl with OR, —O—) | Ce(NH$_4$)$_2$(NO$_3$)$_6$ |
| 4. (RO-aryl-O—) | Ce(NH$_4$)$_2$(NO$_3$)$_6$ |
| 5. —CH=CH(CH$_2$)$_2$— | O$_3$, OsO$_4$/IO$_4^-$ or KMnO$_4$ |
| 6. —CH=CHCH$_2$— | O$_3$, OsO$_4$/IO$_4^-$ or KMnO$_4$ |
| 7. —CH$_2$CH=CH— | O$_3$, OsO$_4$/IO$_4^-$ or KMnO$_4$ |
| 8. (furan derivative) | 1) O$_2$ORBr$_2$, MeOH 2) H$_3$O$^+$ |
| 9. —CH=CHCH$_2$O— | (Ph$_3$P)$_3$RhCl(H) |

TABLE 1-continued

LINKER GROUPS

| LINKER GROUP | CLEAVAGE REAGENT |
|---|---|
| 10. (Br-aryl-O—) | Li, Mg or BuLi |
| 11. —S—CH$_2$—O— | Hg$^{+2}$ |
| 12. (X-CH-CH$_2$-O—) | Zn or Mg |
| 13. (OH-CH-CH$_2$-O—) | Oxidation, e.g., Pb(OAc)$_4$ or H$_5$IO$_6$ |

R = H or lower alkyl
X = electron withdrawing group such as Br, Cl and I.

The tags of this invention, T, are chemical entities which possess several properties: they must be detachable from the solid supports, preferably by photolysis or oxidation; they must be individually differentiable, and preferably separable; they must be stable under the synthetic conditions; they must be capable of being detected at very low concentrations, e.g., $10^{-18}$ to $10^{-9}$ mole; they should be identifiable with readily-available equipment which does not require sophisticated technical capabilities to operate; and they should be relatively economical. The tags may be structurally related or unrelated, e.g., a homologous series, repetitive functional groups, related members of the Periodic Chart, different isotopes, combinations thereof, and the like. At the end of the combinatorial synthesis, to each solid support, there will usually be attached at least 0.01 femtomol, usually 0.001–50 pmol, of each tag. The tags may be aliphatic, alicyclic, aromatic, heterocyclic, or combinations thereof. Distinguishing features may be the number of repetitive units, such as methylene groups in an alkyl moiety; alkyleneoxy groups in a polyalkyleneoxy moiety; halo groups in a polyhalo compound; α- and/or β-substituted ethylene groups where the substituents may be alkyl groups, oxy, carboxy, amino, halo, or the like; isotopes; etc.

The materials upon which the combinatorial syntheses of the invention are performed are referred to as solid supports, beads, and resins. These terms are intended to include:

a) beads, pellets, disks, fibers, gels, or particles such as cellulose beads, controlled pore-class beads, silica gels, polystyrene beads optionally cross-linked with divinylbenzene and optionally grafted with polyethylene glycol and optionally functionalized with amino, hydroxy, carboxy, or halo groups, grafted co-poly beads, polyacrylamide beads, latex beads, dimethylacrylamide beads optionally cross-linked with N,N'-bis-acryloyl ethylene diamine, glass particles coated with hydrophobic polymer, etc., i.e., material having a rigid or semi-rigid surface; and b) soluble supports such as low molecular weight non-cross-linked polystyrene.

It is intended that the definitions of any substituent or symbol (e.g., $R^3$) in a particular molecule be independent of its definitions elsewhere in the molecule. Thus, $NR^3R^3$ represents NH$_2$, NHCH$_3$, N(CH$_3$)$_2$, etc.

Optical Isomers-Diastereomers-Geometric Isomers-Tautomers

Some of the compounds described herein contain one or more asymmetric centers and may thus give rise to enantiomers, diastereomers, and other stereoisomeric forms which may be defined in terms of absolute stereochemistry as (R) or (S). The present invention is meant to comprehend all such possible diastereomers as well as their racemic and optically pure forms and mixtures thereof. Optically active (R) and (S) forms may be prepared using chiral synthons or chiral reagents, or resolved using conventional techniques. When the compounds described herein contain olefinic double bonds or other centers of geometric asymmetry, and unless specified otherwise, it is intended to include both E and Z geometric isomers. Likewise, all tautomeric forms are intended to be included.

Salts

The pharmaceutical compositions of the present invention comprise a compound of Formula II as an active ingredient or a pharmaceutically acceptable salt thereof, and may also contain a pharmaceutically acceptable carrier and, optionally, other therapeutic ingredients. The term "pharmaceutically acceptable salts" refers to salts prepared from pharmaceutically acceptable non-toxic acids or bases including organic and inorganic acids or bases.

When a compound of the present invention is acidic, salts may be prepared from pharmaceutically acceptable non-toxic bases. Salts derived from all stable forms of inorganic bases include aluminum, ammonium, calcium, copper, iron, lithium, magnesium, manganese, potassium, sodium, zinc, etc.

Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion-exchange resins such as arginine, betaine, caffeine, choline, N,N'-dibenzyl-ethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucosamine, morpholine, piperazine, piperidine, polyamine resins, procaine, purine, theobromine, triethylamine, trimethylamine, tripropylamine, etc.

When a compound of the present invention is basic, salts may be prepared from pharmaceutically acceptable non-toxic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, mandelic, methanesulfonic, mucic, nitric, pamoic, pantothenic, phosphoric, succinic, sulfuric, tartaric, p-toluenesulfonic, etc. Particularly preferred are citric, hydrobromic, maleic, phosphoric, sulfuric, and tartaric acids.

In the discussion of methods of treatment herein, reference to the compounds of Formula II is meant to also include the pharmaceutically acceptable salts thereof.

Utilities

The ability of the compounds of Formula II to interact with a adrenergic receptors indicates that the compounds are useful to treat, prevent, or ameliorate hypertension and benign prostate hypertrophy in mammals, especially in humans.

The ability of the compounds of Formula II to interact with dopamine receptors indicates that the compounds are useful to treat, prevent, or ameliorate Alzheimer's disease and depression in humans.

The ability of the compounds of Formula II to interact with θ-opiate receptors indicates that the compounds are useful to treat, prevent, or ameliorate schizophrenia in mammals, especially humans.

The ability of the compounds of Formula II to interact with $K^+$ channels indicates that the compounds are useful to treat, prevent, or ameliorate hypertension, asthma, and pulmonary insufficiency in mammals, especially humans.

The ability of certain compounds of Formula II to inhibit carbonic anhydrase isozymes makes them useful for preventing or reversing the symptoms induced by these enzymes in a mammal. This enzyme inhibition indicates that the compounds are useful to treat, prevent, or ameliorate ocular diseases, particularly glaucoma in mammals, especially in humans.

Dose Ranges

The magnitude of the prophylactic or therapeutic dose of the compounds of Formula II will vary with the nature and severity of the condition to be treated and with the particular compound of Formula II and its route of administration. In general, the daily dose range for anti-enzymic use lies in the range of 20 to 0.001 mg/kg body weight of a mammal, preferably 10 to 0.01 mg/kg, and most preferably 1.0 to 0.1 mg/kg, in single or divided doses. In some cases, it may be necessary to use doses outside these ranges.

When a composition for intravenous administration is employed, a suitable daily dosage range is from about 10 to 0.0005 mg (preferably 5 to 0.01 mg) compound of Formula II per kg body weight.

When a composition for oral administration is employed, a suitable daily dosage range is from about 20 to 0.001 mg (preferably 10 to 0.01 mg) compound of Formula II per kg body weight.

When a composition for ophthalmic administration is employed, a suitable daily dosage range is from about 10–0.01% (preferably 5.0–0.5 compound of Formula II, typically prepared as a 2.0–0.1% by weight solution or suspension of a compound of Formula II in an acceptable ophthalmic formulation.

The compounds of Formula II may also be used in combination with other pharmaceutically active ingredients. For example, a typical ocular formulation may comprise the compound alone or in combination with a β-adrenergic blocking agent such as timolol maleate or a parasympathomimetic agent such as pilocarpine. When used in combination, the two active ingredients are present in approximately equal parts.

Pharmaceutical Compositions

Any suitable route of administration may be employed for providing a mammal, especially a human, with an effective dosage of a compound of Formula II. For example, oral, rectal, topical, parenteral, ocular, pulmonary, nasal, etc. routes may be employed. Dosage forms include tablets, troches, dispersions, suspensions, solutions, capsules, creams, ointments, aerosols, and the like.

The pharmaceutical compositions of the present invention comprise a compound of Formula II, or a pharmaceutically acceptable salt thereof, as an active ingredient, and may also contain a pharmaceutically acceptable carrier and, optionally, other therapeutically active ingredients.

The compositions include compositions suitable for oral, rectal, topical (including transdermal devices, aerosols, creams, ointments, lotions, and dusting powders), parenteral (including subcutaneous, intramuscular, and intravenous), ocular (ophthalmic), pulmonary (nasal or buccal inhalation), or nasal administration; although the most suitable route in any given case will depend largely on the nature and severity of the condition being treated and on the nature of the active ingredient. They may be conveniently presented in unit dosage form and prepared by any of the methods well known in the art of pharmacy.

A compound of Formula II may be combined as the active ingredient in intimate admixture with a pharmaceutical carrier according to conventional pharmaceutical compounding techniques. The carrier may take a wide variety of forms depending on the nature of the preparation desired for administration, i.e., oral, parenteral, etc. In preparing oral dosage forms, any of the usual pharmaceutical media may be used, such as water, glycols, oils, alcohols, flavoring agents, preservatives, coloring agents, and the like in the case of oral liquid preparations (e.g., suspensions, elixirs, and solutions); or carriers such as starches, sugars, microcrystalline cellulose, diluents, granulating agents, lubricants, binders, disintegrating agents, etc. in the case of oral solid preparations such as powders, capsules, and tablets. Solid oral preparations are preferred over liquid oral preparations. Because of their ease of administration, tablets and capsules are the preferred oral dosage unit form. If desired, capsules may be coated by standard aqueous or non-aqueous techniques.

In addition to the dosage forms described above, the compounds of Formula II may be administered by controlled release means and devices such as those described in U.S. Pat. Nos. 3,536,809; 3,598,123; 3,630,200; 3,845,770; 3,916,899; and 4,008,719, which are incorporated herein by reference.

Pharmaceutical compositions of the present invention suitable for oral administration may be prepared as discrete units such as capsules, cachets, or tablets each containing a predetermined amount of the active ingredient in powder or granular form or as a solution or suspension in an aqueous or nonaqueous liquid or in an oil-in-water or water-in-oil emulsion. Such compositions may be prepared by any of the methods known in the art of pharmacy. In general, the compositions are prepared by uniformly and intimately admixing the active ingredient with liquid carriers, finely divided solid carriers, or both and then, if necessary, shaping the product into the desired form. For example, a tablet may be prepared by compression or molding, optionally with one or more accessory ingredients. Compressed tablets may be prepared by compressing in a suitable machine the active ingredient in a free-flowing form such as powder or granule optionally mixed with a binder, lubricant, inert diluent, or surface active or dispersing agent. Molded tablets may be made by molding in a suitable machine, a mixture of the powdered compound moistened with an inert liquid diluent. Ophthalmic inserts are made from compression molded films which are prepared on a Carver Press by subjecting the powdered mixture of active ingredient and HPC to a compression force of 12,000 lb. (gauge) at 149° C. for 1–4 min. The film is cooled under pressure by having cold water circulate in the platen. The inserts are then individually cut from the film with a rod-shaped punch. Each insert is placed in a vial, which is then placed in humidity cabinet (88% relative humidity at 30° C.) for 2–4 days. After removal from the cabinet, the vials are capped and then autoclaved at 121° C. for 0.5 hr.

The following are representative pharmaceutical dosage forms of the compounds of Formula II:

| I.M. Injectable Suspension | mg/mL |
|---|---|
| Compound of Formula II | 10 |
| Methylcellulose | 5 |
| Tween 80 | 0.5 |
| Benzyl alcohol | 9 |
| Benzalkonium chloride | 1 |
| Water for injection to a total volume of 1 mL | |

| Tablet | mg/tablet |
|---|---|
| Compound of Formula II | 25 |
| Microcrystalline cellulose | 415 |
| Povidone | 14 |
| Pregelatinized starch | 43.5 |
| Magnesium stearate | 2.5 |
| | 500 |

| Capsule | mg/capsule |
|---|---|
| Compound of Formula II | 25 |
| Lactose powder | 573.5 |
| Magnesium stearate | 1.5 |
| | 600 |

| Aerosol | Per canister |
|---|---|
| Compound of Formula II | 24 mg |
| Lecithin, NF liquid concentrate | 1.2 mg |
| Trichlorofluoromethane, NF | 4.025 gm |
| Dichlorodifluoromethane, NF | 12.15 gm |

| Ophthalmic Solution | mg/mL |
|---|---|
| Compound of Formula II | 1 |
| Monobasic sodium phosphate $2H_2O$ | 9.38 |
| Dibasic sodium phosphate $12H_2O$ | 28.48 |
| Benzalkonium chloride | 1 |
| Water for injection to a total volume of 1 mL | |

| Ophthalmic Suspension | mg/g |
|---|---|
| Compound of Formula II | 1 |
| Petrolatum liquid to a total weight of 1 g | |

| Ophthalmic Insert | mg/insert |
|---|---|
| Compound of Formula II | 1 |
| Hydroxypropylcellulose | 12 |

These compounds of Formulae I and II may also be used as libraries for discovering a new lead structures by evaluation across an array of biological assays, including the discovery of selective inhibition patterns across isozymes. These libraries are thus tools for drug discovery; i e., as a means to discover novel lead compounds by screening the libraries against a variety of biological targets and to develop structure-activity relationships in large families of related compounds. The libraries may be tested with the ligands attached to the solid supports as depicted in Formula I or the individual compounds II may be detached prior to evaluation. With the compounds of Formula I, screening assays such as FACS sorting, bead lawn assays, and cell lawn assays may be used. When a compound is detached prior to evaluation, its relationship to its solid support is maintained, for example, by location within the grid of a standard 96-well plate or by location of activity on a lawn of cells. The solid support associated with bioactivity or the solid support related to the detached ligand may then be decoded to reveal the structural or synthetic history of the active compound (Ohlmeyer et al., *Proc. Natl. Acad. Sci. USA*, 90, 10922–10926, December, 1993).

Assays for Determining Biological Activity

The compounds of the present invention may be tested by assays well known in the art for interaction with a adrenergic receptors, interaction with dopamine receptors, interaction with θ-opiate receptors, interaction with $K^+$ channels, and carbonic anhydrase inhibition. For example, representative references teaching carbonic anhydrase inhibition assays are:

Carbonic Anhydrase Inhibition—Maren and Couto, "The Nature of Anion Inhibition of Human Red Cell Carbonic Anhydrases", *Archive. of Biochem. and Biophy.*, 19, No.2, September, 501–510 (1979).

Carbonic Anhydrase Inhibition—Ponticello et al., "Thienothiopyran-2-sulfonamides: A Novel Class of Water-Soluble Carbonic Anhydrase Inhibitors", *J. Med. Chem.*, 30, 591–597 (1987).

Carbonic Anhydrase Inhibition—It has now been found that the use of very low initial concentrations (0.04–1.6, preferably about 0.6, μM) of dansylamide and (0.03–1.2, preferably about 0.3, μM) of carbonic anhydrase to assay test compounds for carbonic anhydrase inhibition not only allows the use of very small total volumes (approx. 25–100, preferably about, 50 μL) per assay but also allows one to distinguish high-affinity from low-affinity compounds without either re-elution or re-synthesis of the test compound. By increasing the concentration of dansylamide from ~0.1 μM to ~200 μM directly in the assay sample, relatively weak inhibitors can be distinguished from relatively strong inhibitors on the same aliquot of test compound. The small total volume advantageously permits high throughput assaying of small quantities of test compounds, for example, in 96-well plates, and the reduced concentration of dansylamide advantageously permits the detection of test compounds that have a wide range ($\leq 500$ nM) of characteristic dissociation constants. The following materials are used:

| | |
|---|---|
| 100. | mM sodium phosphate buffer, pH 7.4 |
| 0.6 | μM dansylamide (Sigma D-3882) |
| 0.3 | μM bovine carbonic anhydrase inhibitor (Sigma C-3934) |

Reactions are carried out in 50 μL total volume in 96-well plates, preferably, Dynatech MicroFluor plates, white with 'U' bottom, containing the test compounds. The assay mix is prepared immediately before use, and 50 μL of the assay solution is pipetted into each well of plates in which the test compounds are previously dried. The plates are spun briefly in a tabletop centrifuge before reading fluorescence. Fluorescence is read in a Perkin-Elmer LS 50B spectrofluorimeter fitted with a Well Plate Reader Accessory using an excitation wavelength of 274 nm (2.5 nm slit) and an emission wavelength of 454 nm (20 nm slit), with a 390 nm cutoff filter in place. Fluorescence measurements are averaged over 1 sec for each well. To identify wells in which inhibitors are present, first a plate with no exogenous inhibitors is read, which typically gives a fluorescence reading of 2.6–3.1 (typical standard deviation ±0.06) for a given assay solution. In plates containing inhibitor candidates, active inhibitors cause a decrease in the fluorescence signal of greater than 5 times the standard deviation.

To distinguish high-affinity from low affinity candidates, 5 μL of a 2 μM stock of dansylamide in DMSO is added to the above test solution, and the assay repeated as above. Typical readings are 7.5 to 8.5±0.4 (standard deviation) among previously identified inhibitors. High-affinity compounds lower the signal by greater than 3 standard deviations). Thus, the increased concentration of dansylamide is sufficient to displace relatively weak inhibitors (e.g., chlorothiazide, $K_i$~75 NM) without displacing relatively strong inhibitors (e.g., acetazolamide, $k_i$~7.5 nM).

Bead Lawn Assay (General Method). An enzyme of interest is incorporated into a gellable gum such as silica gel, agar, agarose, pectin, polyacrylamide, gelatin, starch, and gellan gum, preferably a low melting-temperature agarose gel (0.5–2.0%, wt./vol.), which is layered on top of a lawn, no greater than one bead in thickness, of solid supports with attached ligands. The detection of an active combinatorial library member is accomplished by photoeluting the ligands from the beads in situ by exposure to U.V. light. To minimize premature photoelution, the beads are preferably protected from ambient light sources prior to U.V. exposure. The beads are evaluated by placing a second layer, preferably low-melt agarose gel, containing a substrate on too of the one containing the enzyme and the photoreleased library members, and allowing enzymic conversion of substrate into product by diffusion of the substrate into the enzyme-containing gel. The substrate is preferably one that produces a photometric change upon conversion into product; e.g., the generation of a colored product, a fluorescent product, or a chemiluminescent reaction (where one of the products is a photon). The second layer may comprise a gellable gum such as silica gel, agar, agarose, pectin, polyacrylamide, gelatin, starch, and gelan gum, or a solid material such as a matrix containing an array of fluorogenic-pellets. Inhibition of the enzyme by a library member results in a difference in appearance in the vicinity of the attached bead and allows for selection of the bead and the identifiers which encode for the inhibitor. This technique may be used with a variety of enzymes, for example:

| | |
|---|---|
| Acid Phosphatase | Furin |
| Activated Protein C | γ-Glutamyltranspeptidase |
| Alkaline Phosphatase | Granzymes A & B |
| Aminopeptidases B & M | HIV Protease |
| Amyloid A4-Generating Enzyme | IL-1B Convertase |
| Angiotensinase | Kallikrein |
| Aryl Sulfatase | Lysozyme |
| β-Galactosidase | Mast Cell Protease |
| β-Glucosidase | Peroxidase |
| β-Glucuronidase | Plasmin |
| Calpains I & II | Prohormone Convertase |
| Cathepsins B, C, D, & G | rANP Precursor Processing Enzyme |
| Cholinesterase | Renin |
| Chymotrypsin | Spleen Fibrinolytic Proteinase |
| Collagenase | Staphylocoagulase |
| Dipeptidyl Peptidases I–IV | Thrombin |
| Elastase | Tissue Plasminogen Activator |
| Endothelin Converting Enzyme | Trypsin |
| Factor Xa | Tryptase |
| Factor XIa | Urokinase |
| Factor XIIa Df-Protease | |

A bead lawn assay for testing carbonic anhydrase inhibition preferably comprises agarose for both layers, bovine carbonic anhydrase, and fluorescein diacetate.

Bead Lawn Assay (Carbonic Anhydrase). Beads to be tested are arrayed in a minimal amount of methanol in a 60 mm polystyrene tissue culture dish and then all the methanol allowed to evaporate. A 2.5% (wt./vol.) mixture of agarose (SeaPlaque, FMC BioProducts, Rockland, Me.) in 20 mM sodium phosphate buffer (pH 7.4) is heated on a hot plate until the agarose dissolves and then is equilibrated to 37° C. in a water bath. A separate stock of the same buffer is also equilibrated to 37° C. The enzyme layer is prepared as follows: 100 μL of a bovine carbonic anhydrase stock (0.5 mg/mL or 53 μM based on absorbance at 280 nm, Sigma #C-3934) is added to 2.15 mL of buffer, and 1.25 mL agarose solution is added to the mixture. The agarose/enzyme solution is poured onto the dish containing the beads and the agarose is allowed to solidify at r.t. for 3–5 men. To identify zones of inhibitions, the compounds, which are optionally photoeluted by exposure to 4.7–6 mW/Cm²365 nm UV light for 5 sec. to 1 hr., are overlayed with fluorescein diacetate (FLDA, Molecular Probes, Eugene, Oreg.), which is pre-oared as follows: to 2.25 mL phosphate buffer is added 10 μL FLDA stock (10 mM in DMF at −20° C.) and 1.25 mL agarose (final FLDA concentrations: 30 μM). The solution is mixed thoroughly then poured over the enzyme layer in the dish. Zones of inhibition appear after 1–2 min. and intensify over 30–45 min. They are dark against a yellow-green background when illuminated by short-wave UV light ($\lambda{-}_{max}$=254 nm).

Bead Lawn Assay (Inositol Monophosphatase). The assay is similar to that for carbonic anhydrase, with the following substitutions: The buffer used is 20 mM Tris, 1 mM EGTA, pH 7.8. The enzyme layer contains 1 mg/mL recombinant human inositol monophosphatase (purified from $E.\ coli$) and 10 mM $MgCl_2$. Three alternative substrates are used: methylumbelliferyl phosphate (Sigma, M-8883), a fluorogenic substrate, detected using filters around $\lambda_{max}$=388 nm and $\lambda_{max}$=420 nm; or CSPD or CDP-Star (chemiluminescent substrates for alkaline phosphatase, Tropix, Bedford Mass.), detected directly without requiring filters. The preferred substrate is CSPD.

Methods of Synthesis

The compounds of the present invention can be prepared according to the following methods. At each step in the synthesis each solid support upon which a compound is being synthesized is uniquely tagged to define the Particular chemical event(s) occurring during that step. The tagging is accomplished using identifiers such as those of Formula IV, which record the sequential events to which the support is exposed during the synthesis, thus providing a reaction history for the compound produced on each support. The identifiers are used in combination with one another to form a binary or higher order encoding scheme permitting a relatively small number of identifiers to encode a relatively large number of reaction products. For example, when used in a binary code, N identifiers can encode up to $2^N$ different compounds and/or conditions. By associating each variable or combination of variables at each step of the synthesis with a combination of identifiers which uniquely define the chosen variables such as reactant, reagent, reaction conditions, or combinations of these, one can use the identifiers to define the reaction history of each solid support.

In carrying out the syntheses, one beings with at least $10^3$, desirably at least $10^4$, and generally not exceeding $10^{15}$ solid supports. Depending on the pre-determined number of $R^1/R^2$ choices for the first step, one divides the supports accordingly into as many containers. The appropriate reagents and reaction conditions are applied to each container and the combination of identifiers which encode for each $R^1/R^2$ choice is added and attached. Depending on the chemistries involved, the tagging may be done prior to, concomitantly with, or after the reactions which comprise each choice. As a control, sample supports may be picked at any stage and a portion of their tags detached and decoded to verify that the correct tags are bound to the sample supports. As needed, one may wash the beads free of any excess reagents or by-products before proceeding. At the end of each step, the supports are usually combined, mixed, and again divided, this time into as many containers as pre determined for the number of choices for the second step in the synthesis. This procedure of dividing, reacting, tagging, and remixing is repeated until the combinatorial synthesis is completed.

Scheme 1

Functionalized supports such as amino-functionalized or hydroxy-terminating PEG grafted polystyrene beads are divided into a pre-determined number of reaction vessels and are reacted with a cleavable linker/ligand element 3, which has been pre-formed, to generate 4. Unique tagging of the supports in each reaction vessel is achieved with combinations of identifiers encoded in a binary scheme, e.g., as depicted in Table 1-1 for three choices of $R^1$ and $R^2$. The identifiers are attached by adding a solution of the identifiers (in a 1.5% wt./wt. identifier:solid support ratio) to a batch of supports suspended in $CH_2Cl_2$ and shaking the mixture for 30 min. A dilute solution of rhodium trifluoroacetate dimer is added and the mixture is immediately shaken 4 hr and washed in $CH_2Cl_2$. The procedure is repeated and the mixture shaken for 14 hr and then washed in DMF/DCM.

Scheme 2

The compounds 4 are pooled, mixed, and divided into a pre-determined number of reaction vessels, each of which is treated with one reagent corresponding to ligand element $=CR^4R^5$, in the presence of pyrrolidine to produce 5a, 5b, and 5c. Unique tagging of the supports in each reaction vessel is achieved with combinations of additional identifiers encoded in a binary scheme, e.g., as depicted in Table 1-2 for seven choices of $R^4R^5$.

Scheme 3

The compounds 5c, where $R^4/R^5/X$ represents the residue of piperidine, pyrrolidine, or aminocyclohexane, are pooled, mixed, and then divided into a pre-determined number of reaction vessels. The supports in each reaction vessel are uniquely tagged with combinations of additional identifiers encoded in a binary scheme, e.g., as depicted in Table 1-3 for 30 choices of $R^8$ and in Table 1-5 for six choices of $R^{14}$ and four choices of heteroaryl groups. After removal of any N-protecting Boc group in $R^4R^5$, each reaction vessel is treated with one reagent corresponding to ligand element $R^8$ in the presence of solvents such as $CH_2Cl_2$, DMF, or EtOH and, when required, bases such as triethylamine or 2,6-lutidine to produce 6 having an $R^8$ substituent at C-2 and a ketone at C-4, i.e., when $R^6R^7$ together are 0. In scheme 3, $R^{14}$ is benzyl, $-CH_2-Ph-4-F$, $CH_2-Ph-4-OCH_3$, $-CH_2-4-Py$, n-pentyl, or $-CH_2$-c-propyl; and heteroaryl is

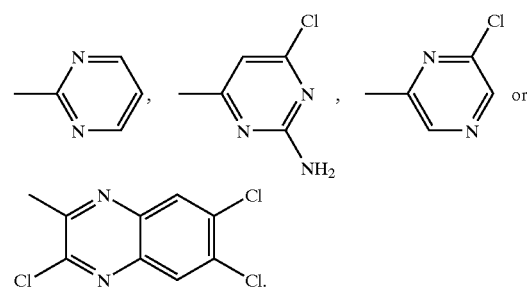

Scheme 4

A portion of the compounds 5a, 5b, 5c, and 6 may be pooled, mixed, and then divided into a pre-determined number of reaction vessels where they may be uniquely tagged with combinations of additional identifiers encoded in a binary scheme, e.g., as in Table 1-4 for three choices of $R^6/R^7$. Each vessel is treated with sodium borohydride to yield 7 as an alcohol an C-4 or is treated with 1,2- dithioethane and a Lewis acid such as $BF_3.Et_2O$ to yield 8 as a dithiolane at C-4, or is treated with an appropriate non-beta branched primary amine in the presence of $NaCNBH_3$ in MeOH, optionally with acetic acid, to yield secondary amine 9, or is left untreated.

Compounds 5a, 5b, 5c, 6, 7, 8, and 9 are then exposed to UV light (~360 nm) in polar solvents such as DMSO, $H_2O$, or a lower alkanol such as MeOH to cleave the compounds of Formula II from the support/linker complex.

Scheme 5

TentaGel resin may be modified with bis-Boc Lysine to increase the available reaction sites for ligand attachment Bis-Boc-lysine in DMF, HOBt, and DIC are shaken at r.t. and then dry TentaGel resin is added. The mixture is shaken at r.t. for 17 hr and is then washed alternately with methanol and DCM and then with THF and dried under vacuum. To deprotect the resin, DCM is added, followed by a 30% TFA solution in DCM (100 mL). The vessel is shaker at room temperature for 15 min. before adding neat TFA. The vessel is shaken at room temperature for 2.5 hr at which time the resin is washed with DCM, then treated with a solution of 10% triethylamine in DCM, then washed with DCM and DMF.

For purposes of simplicity, the schemes do not show the use of this bis modification.

Scheme 6

Functionalized supports such as amino-functionalized or hydroxy-terminating PEG grafted polystyrene beads are divided into a pre-determined number of reaction vessels and are reacted with a cleavable linker/ligand element 10, which has been pre-formed, to generate 11. Unique tagging of the supports in each reaction vessel is achieved with combinations of identifiers encoded in a binary scheme, e.g., as depicted in Table 2-1 for seven choices of $—(CH_2)_{1-6}R^{17}$. The identifiers are attached by adding a solution of the identifiers (in a 7% wt./wt. identifier:solid support ratio) to each batch of supports suspended in EtOAc and shaking the mixture for 1 hr. A dilute solution of rhodium trifluoroacetate dimer in DCM is added and the mixture is shaken 15 hr and washed with DCM (4×) and EtOAc (2×). The procedure is repeated for each identifier.

To deprotect the encoded resin, it is suspended in DCM and then agitated with a TFA solution in DCM. The resin is then washed with DCM followed by treatment with triethylamine in DCM and then washed with DCM.

Scheme 7

The compounds 12 are pooled, mixed, and divided into a pre-determined number of reaction vessels, each of which is treated with one acetophenone reagent corresponding to ligand element $R^2$, in the presence of DIC, HOBt, and DMF to produce 4'. Unique tagging of the supports in each reaction vessel is achieved with combinations of additional identifiers encoded in a binary scheme analogous to that in Table 2-1.

Scheme 8

The compounds 4' are mixed, pooled, and divided into a predetermined number of reaction vessels, each of which is treated with and aldehyde or ketone element corresponding to $R^4/R^5$ in the presence of pyrrolidine in methanol at 75° C. to produce the compounds 5a', 5b', and 5c'. Unique tagging of the supports in each reaction vessel is achieved with combinations of additional identifiers encoded in a binary scheme analogous to that in Table 2-1.

Scheme 9

The compounds a, where $R^4/R^5/X$ represents the residue of t-Boc protected piperidine, t-Boc protected aminocyclohexane, or other amine functionalized molecules are mixed, pooled, and divided into a predetermined number of reaction vessels. The supports in each reaction vessel are uniquely tagged with combinations of additional identifiers encoded in a binary scheme analogous to that in Table 2-1. After removal of any N-protecting group in $R^4/R^5$, each vessel is treated with one reagent such as a chloroformate, isocyanate, thioisocyanate, carboxylic acid, alkyl or aryl sulfonyl halide, aldehyde, or a haloheteroaromatic compound corresponding to ligand element $R^8$ in the presence of solvents such as $CH_2Cl_2$, DMF, EtOH, or methanol. When required, bases such as triethylamine, DBU, or 2,6-lutidine and/or other reagents or combinations of reagents such as DIC, $NaCNBH_3$, HOBt, and acetic acid are added to produce 6', having an $R^8$ substituent at C-2 and a ketone at C-4, i.e. when $R^6R^7$ together are O.

Scheme 10

A portion of compounds 5a', 5b', 5c', and 6' may be pooled, mixed, and then divided into a pre-determined number of reaction vessels where they may be uniquely tagged with combinations of additional identifiers encoded in a binary scheme analogous to that in Table 2-1. Each vessel is treated with 1) sodium borohydride in methanol to yield 7' as an alcohol at C-4; 2) 1,2-dithioethane and a Lewis acid such as boron trifluoride etherate to yield 8' as the dithiolane at C-4; 3) an unhindered primary amine along with $NaCNBH_3$ in acetic acid/methanol solvent at ca. 75° C. to yield 9' as an amine at C-4; or 4' is left untreated.

Scheme 11

The compounds 9 or 9' are divided into a predetermined number of reaction vessels. Each vessel is treated with one reagent such as a chloroformate, isocyanate, thioisocyanate, carboxylic acid, alkyl or aryl sulfonyl halide, aldehyde, or a haloheteroaromatic compound corresponding to ligand element $R^{15}$ in the presence of solvents such as $CH_2Cl_2$, DMF, EtOH, or methanol. When required, bases such as triethylamine, DBU, or 2,6-lutidine and/or other reagents or combinations of reagents such as DIC, $NaCNBH_3$, HOBt, and acetic acid are added to produce the corresponding compound 13 or 13'.

Scheme 12

Functionalized supports such as amino-functionalized or hydroxy-terminating PEG grafted polystyrene beads are placed into a reaction vessel and are reacted with a cleavable linker/ligand element 10, which has been pre-formed, to generate 11'. To deprotect the resin, it is suspended in DCM and then agitated with TFA solution in DCM. The resin is then washed with DCM followed by treatment with triethylamine in DCM and then washed with DCM to yield 12'.

In an appropriately sized synthesis vessel is placed HOBt (3 equiv.) and the carboxylic acid Q (X=OH)(3 equiv.) in a solvent such as DMF. DIC (3 equiv.) is added and the vessel agitated for 15 min. before adding the amino resin 12' (1 equiv. of amino sites). The resin is agitated for 5 hrs., then washed with alternating DCM and MeOH (5× each) and then with THF (2×) to yield 14.

In an appropriately sized synthesis vessel is placed the amino resin 12'(1 equiv. of amino sites). A solvent such as DCM is added, followed by an organic base such as triethylamine, pyridine, Hunig's base (di-isopropylethylamine), or 2,6-lutidine (10 equiv.). The resin is agitated for 15 min. before adding the acid halide Q (X=Cl, Br) (5 equiv.) as a dilute solution in a solvent such as DCM. The resin is agitated for 4 hrs. and then washed with DCM and MeOH (5× each) to yield 14.

SCHEME 1
LINKER/1st LIGAND ELEMENT
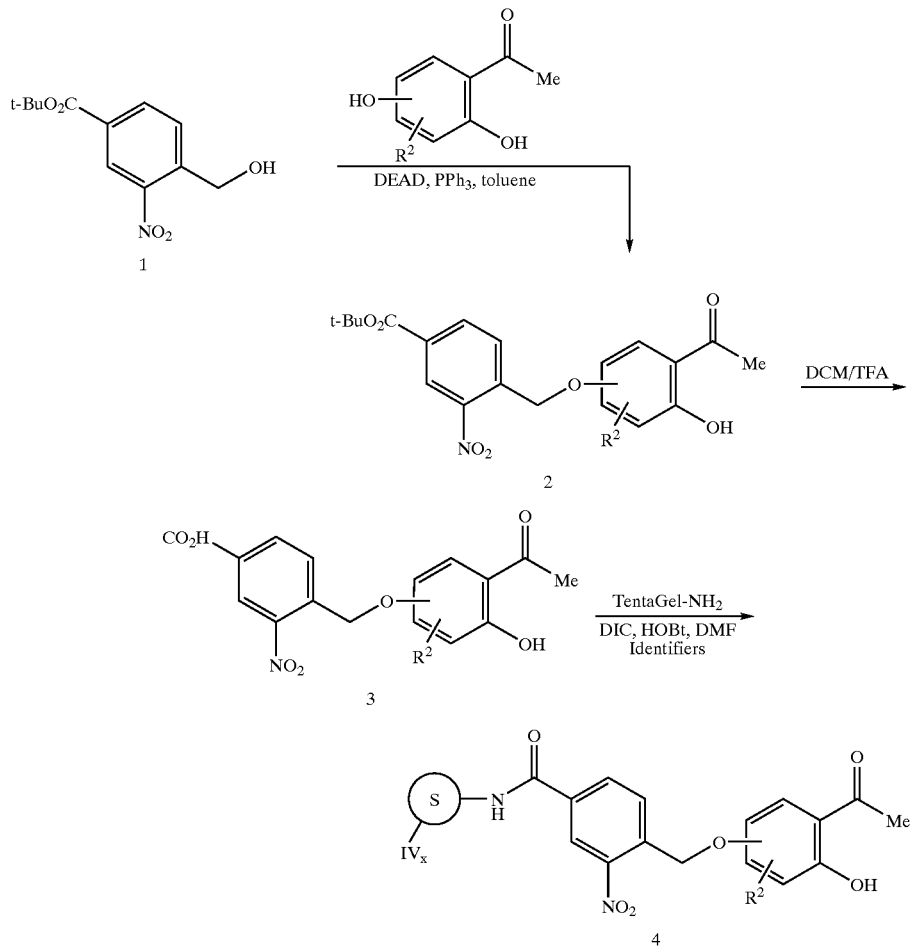
x is 1–30, depending on the binary code for the selected solid support
SCHEME 2
ADDITION OF $R^4/R^5$
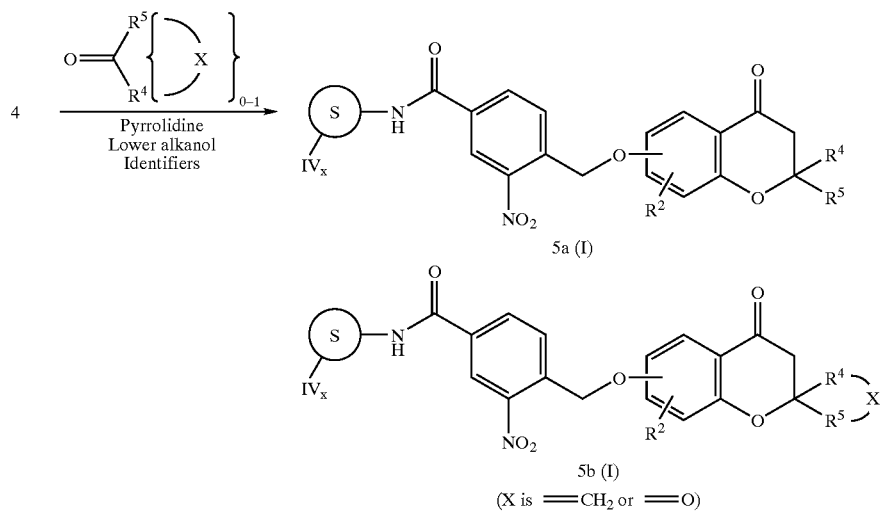
(X is $=CH_2$ or $=O$)

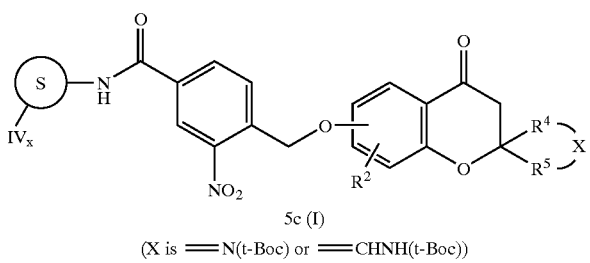
5c (I)
(X is =N(t-Boc) or =CHNH(t-Boc))
SCHEME 3
ADDITION OF $R^8$
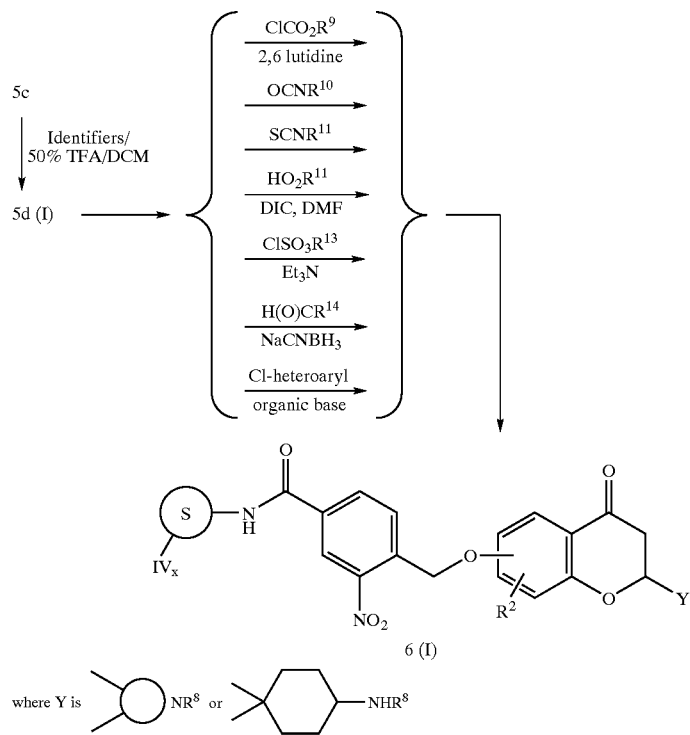
6 (I)
where Y is ⟨⟩—$NR^8$ or ⟨⟩—$NHR^8$
SCHEME 4
ADDITION OF $R^6/R^7$
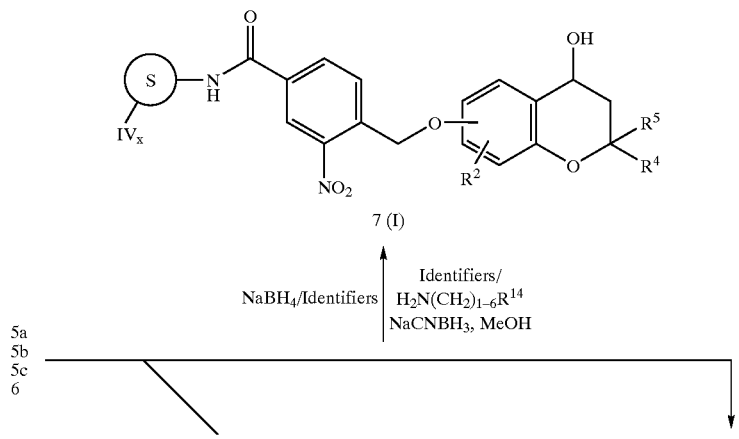

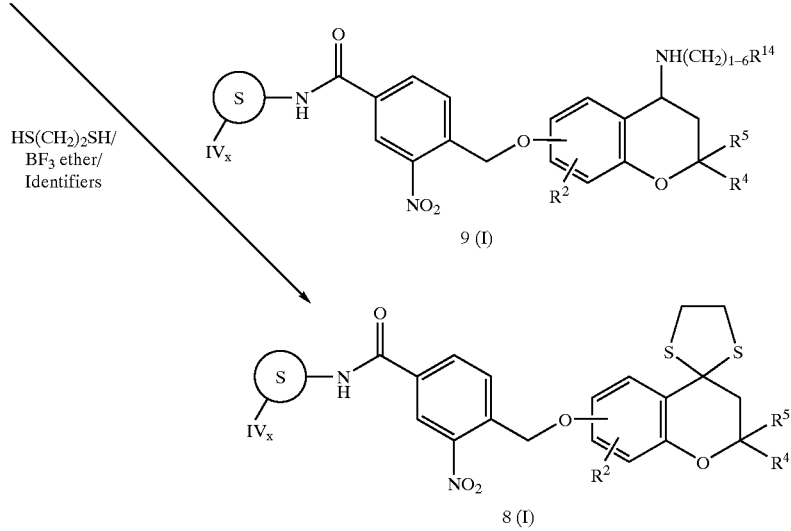
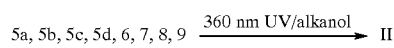
SCHEME 5
BIS-LINKER ATTACHMENT
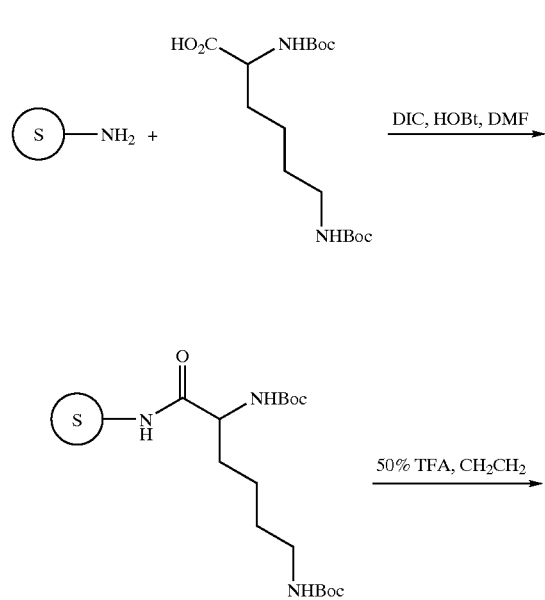
SCHEME 6
CLEAVABLE LINKER/1st LIGAND ELEMENT
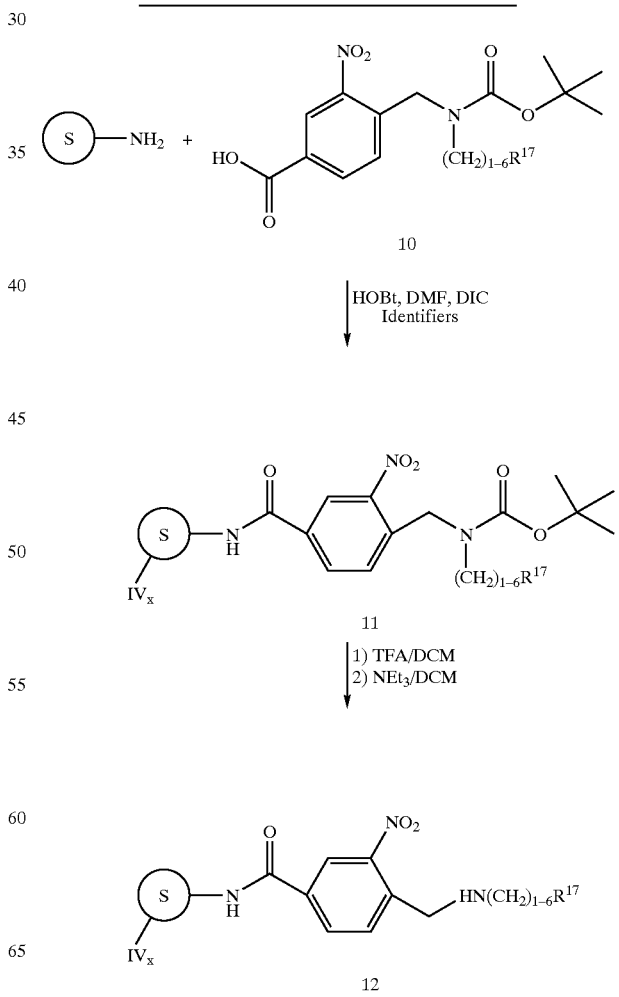

SCHEME 7
ATTACHMENT OF HYDROXYACETOPHENONES
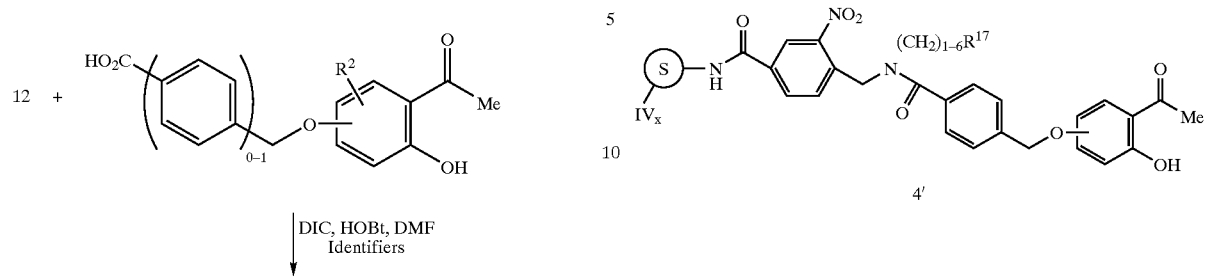
SCHEME 8
ADDITION OF R⁴/R⁵
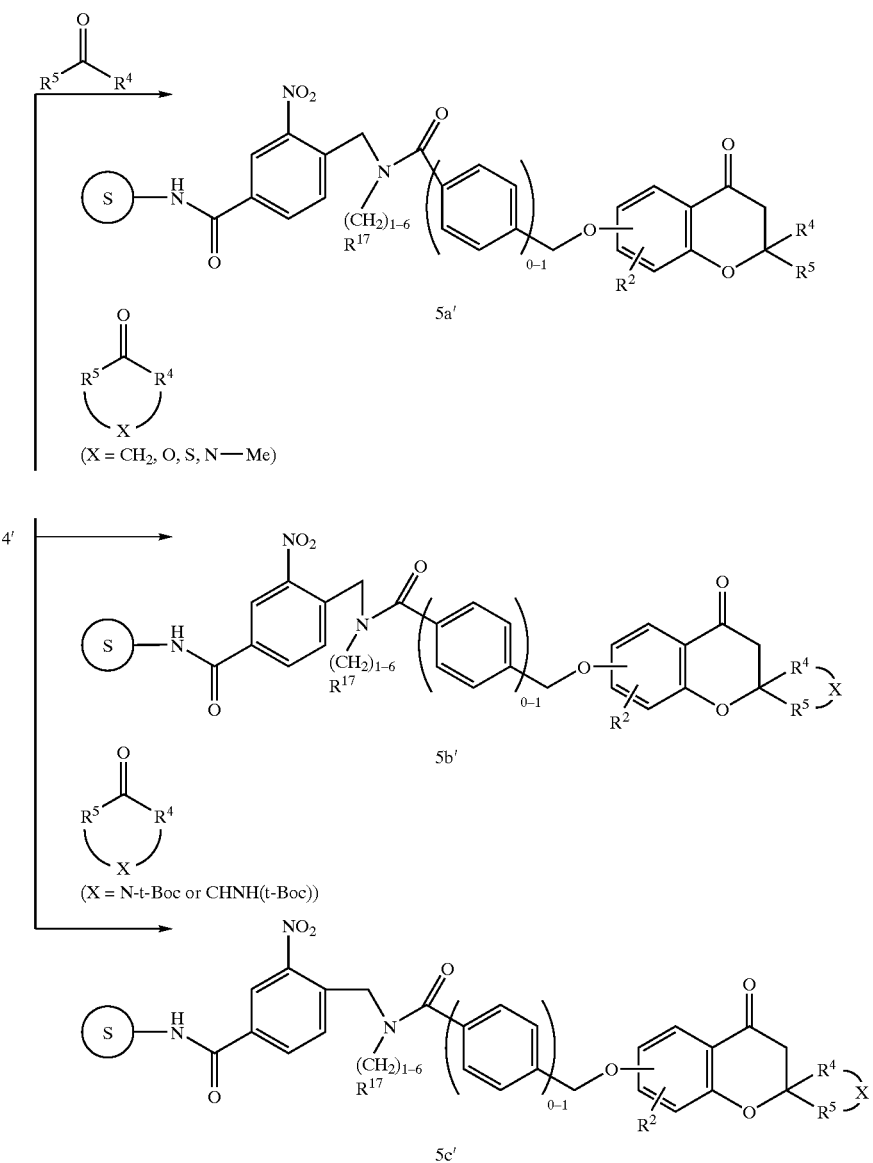

SCHEME 9
ADDITION OF R⁸
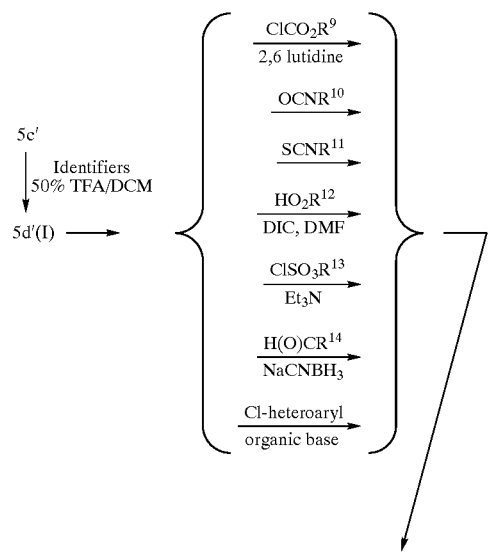
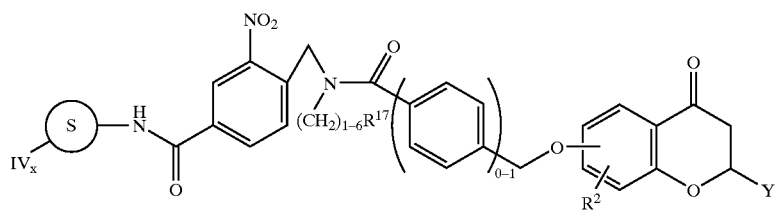
SCHEME 10
ADDITION OF R⁶/R⁷
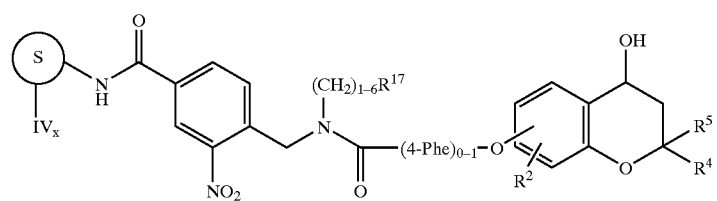

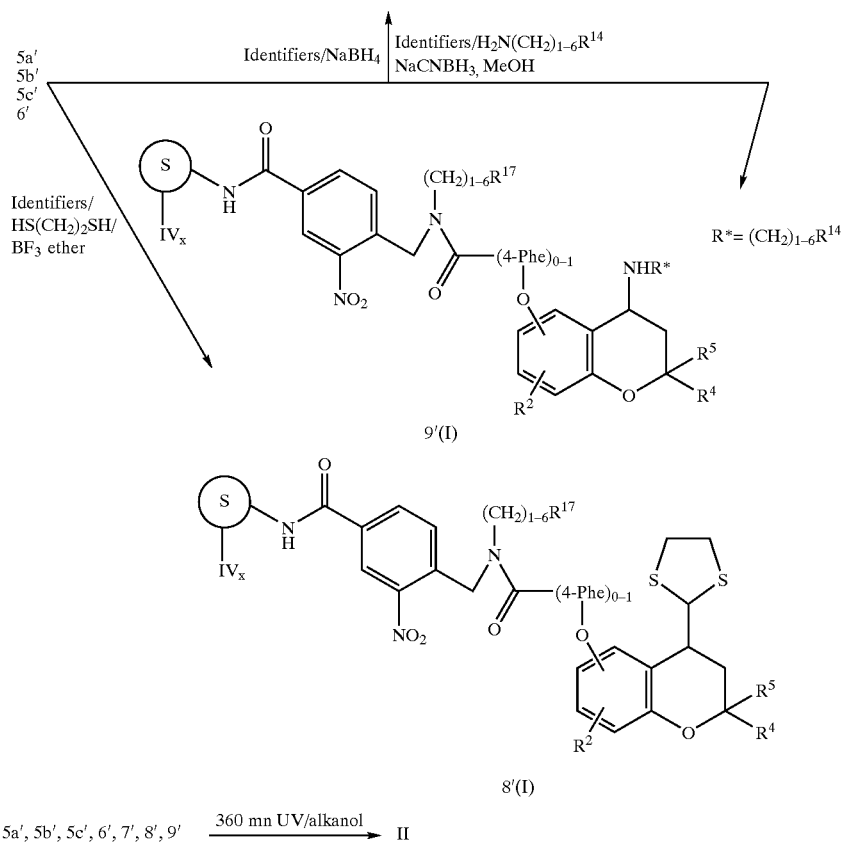
SCHEME 11
ADDITION OF R[15]
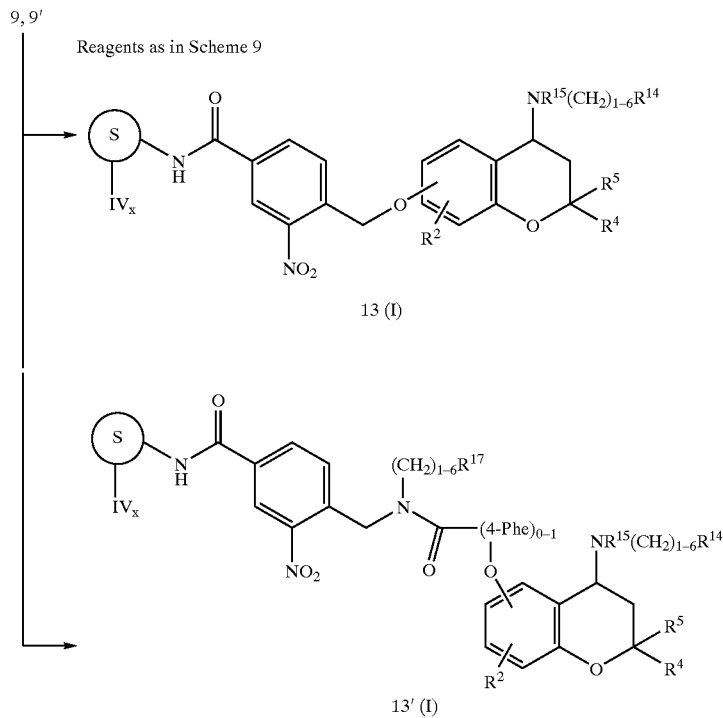

SCHEME 12
COMBINATORIAL SYNTHONS

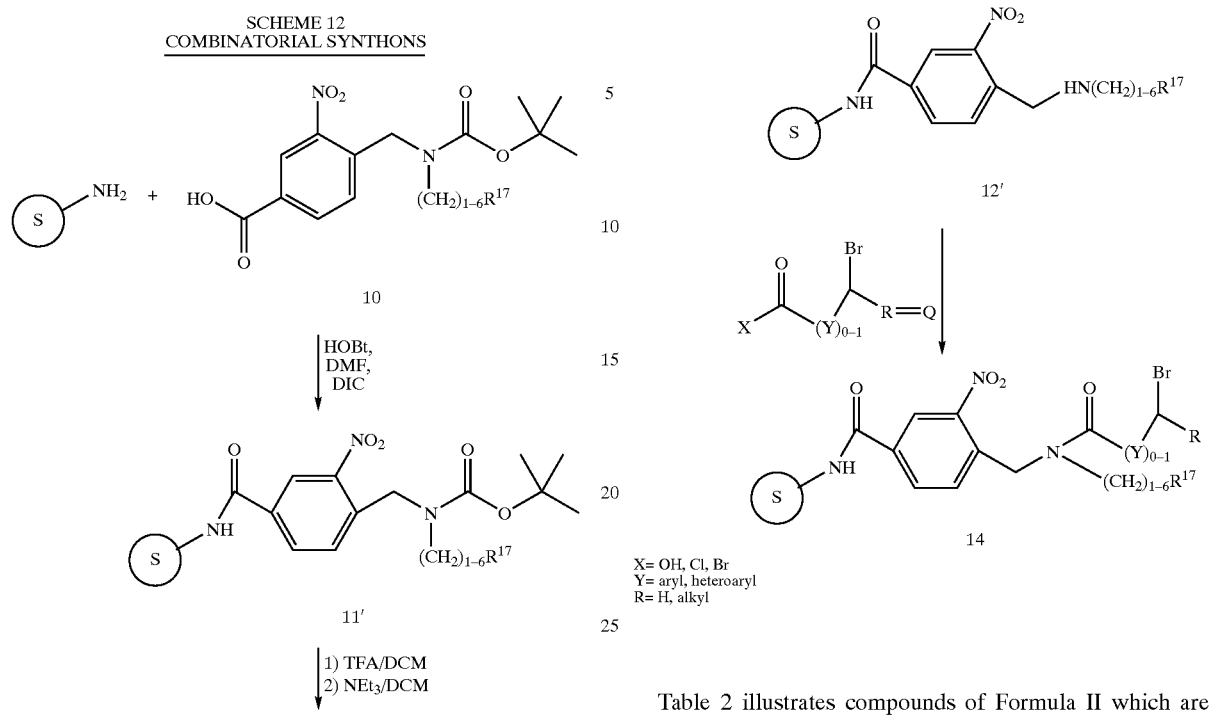

X= OH, Cl, Br
Y= aryl, heteroaryl
R= H, alkyl

Table 2 illustrates compounds of Formula II which are representative of the present invention:

TABLE 2

REPRESENTATIVE COMPOUNDS

| $R^1$ | $R^2$ | $R^4$ | $R^5$ | $R^6$ | $R^7$ |
|---|---|---|---|---|---|
| 6-OH | 8-$CH_3$ | $C_2H_5$ | $C_2H_5$ | OH | H |
| 7-OH | 8-$CH_3$ | $CH_3$ | $CH_3$ | H | OH |
| 5-OH | 7-$C_2H_5$ | H | $CH_2H_5$ | $NH_2$ | H |
| 6-OH—$(CH_2)_2$OH | H | $C_3H_7$ | $CH_3$ | | =O |
| 7-O$CH_2CO_2$H | 7-$CH_2H_5$ | | —$(CH_2)_4$— | H | morpholino |
| 8-O—$(CH_2)_2$OH | H | | —$(CH_2)_5$— | $N(CH_3)_2$ | H |
| 6-$CO_2$H | 8-$CH_3$ | | —$(CH_2)_6$— | | —S$(CH_2)_2$S— |
| 6-CH | H | | —$(CH_2)_2$O$(CH_2)_2$— | | =O |
| 7-OH | 8-$CH_3$ | $CH_3$ | $CH_3$ | | —S$(CH_2)_2$S— |
| 6-OH | H | | —$(CH_2)_5$— | | =O |

Table 3 illustrates additional compounds of Formula II representative of the present invention:

TABLE 3

REPRESENTATIVE COMPOUNDS

| $R^1$ | $R^2$ | $R^4/R^5$ | $R^6$ | $R^7$ | $R^8$ |
|---|---|---|---|---|---|
| 6-OH | H | —$(CH_2)_2NR^8(CH_2)_2$— | OH | H | —CONH-Ph-4-$CF_3$ |
| 7-OH | 8-$CH_3$ | —$CH_2NR^8(CH_2)_3$— | —N⟨morpholino-$SO_2$⟩ | H | —$SO_2$-2-Naph |

TABLE 3-continued

REPRESENTATIVE COMPOUNDS

| $R^1$ | $R^2$ | $R^4/R^5$ | $R^6$ | $R^7$ | $R^8$ |
|---|---|---|---|---|---|
| 5-O(CH$_2$)$_2$OH | 7-C$_2$H$_5$ | —(CH$_2$)$_2$NR$^8$CH$_2$— | ![piperidinyl] | H | —CSNH-Ph |
| 6-OH | H | —(CH$_2$)$_2$NR$^8$(CH$_2$)$_2$— | =O | | —CO-Ph-4-SO$_2$NH$_2$ |
| 7-OH | H | —(CH$_2$)$_2$CH(NR$^8$)(CH$_2$)$_2$— | —S(CH$_2$)$_2$S— | | —CO-Ph-4-SO$_2$NH$_2$ |
| 6-OH | H | —(CH$_2$)$_2$NR$^8$(CH$_2$)$_2$— | =O | | —COCH$_2$Ph |
| 6-OH | H | —(CH$_2$)$_2$NR$^8$CH$_2$— | —S(CH$_2$)$_2$S— | | —CO$_2$-2-Py |
| 7-OH | 8-CH$_3$ | —(CH$_2$)$_2$NR$^8$(CH$_2$)$_2$— | —S(CH$_2$)$_2$S— | | —CO-Ph-4-SO$_2$NH$_2$ |
| 6-OH | H | —(CH$_2$)$_2$NR$^8$CH$_2$— | —S(CH$_2$)$_2$S— | | —CO-Ph-4-SO$_2$NH$_2$ |
| 7-OH | H | —(CH$_2$)$_2$NR$^8$—(CH$_2$)$_2$— | =O | | —CO-Ph-4-SO$_2$NH$_2$ |
| 6-OH | H | —(CH$_2$)$_2$NR$^8$—(CH$_2$)$_2$— | OH | H | CONH-Ph-4-CF$_3$ |
| 7-OH | 8-CH$_3$ | —(CH$_2$)$_2$NR$^8$—CH$_2$— | N(CH$_3$)$_2$ | H | —SO$_2$-2-Naph |
| 5-O(CH$_2$)$_2$OH | 7-C$_2$H$_5$ | —(CH$_2$)$_2$NR$^8$—CH$_2$— | —SCH$_2$CH—(CH$_3$)S— | H | —CSNH-Ph |
| 6-OH | H | —(CH$_2$)$_2$NR$^8$—(CH$_2$)$_2$— | =O | | —CO-Ph-4-SO$_2$NH$_2$ |
| 7-OH | H | —(CH$_2$)$_2$NR$^8$—(CH$_2$)$_2$— | —S(CH$_2$)$_2$S— | | —CO-Ph-4-SO$_2$NH$_2$ |
| 6-OH | H | —(CH$_2$)$_2$NR$^8$—(CH$_2$)$_2$— | =O | | COCH$_2$Ph |
| 6-OH | H | —(CH$_2$)$_2$NR$^8$—CH$_2$— | —S(CH$_2$)$_2$S— | | —CO$_2$-2-Py |
| 7-OH | 8-CH$_3$ | —(CH$_2$)$_2$NR$^8$—(CH$_2$)$_2$— | —S(CH$_2$)$_2$S— | | —CO-Ph-4-SO$_2$NH$_2$ |
| 6-OH | H | —(CH$_2$)$_2$NR$^8$—CH$_2$— | —S(CH$_2$)$_2$S— | | —CO-Ph-4-SO$_2$NH$_2$ |
| 7-OH | H | —(CH$_2$)$_2$NR$^8$—(CH$_2$)$_2$— | =O | | —CO-Ph-4-SO$_2$NH$_2$ |

The invention is further defined by reference to the following examples, which are intended to be illustrative and not limiting.

PREPARATION 1

IDENTIFIERS

Twelve compounds of the general formula:

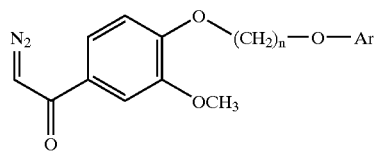

IV wherein:

n=3–12 and Ar is pentachlorophenyl or n=5–6 and Ar is 2,4,6-trichlorophenyl were prepared according to Scheme 13 and the following illustrative example.

a) Methyl vanillate (0.729 g, 4.0 mmol), 1-hydroxy-9-(2,3,4,5,6-pentachlorophenoxy)nonane (1.634 g, 4.0 mmol) and triphenylphosphine (1,258 g, 4.8 mmol) were dissolved in 20 mL dry toluene under argon DEAD (0.76 mL, 0.836 g, 4.8 mmol) was added dropwise and the mixture was stirred at 25° C. for one hr. The solution was concentrated to half volume and purified by flash chromatography eluting with DCM to give 1.0 g (1.7 mmol, 43%) of the product as a white crystalline solid.

b) The methyl ester from Step (a) (1.0 g, 1.7 mmol) was dissolved in 50 mL THF, 2 mL water was added, followed by LiOH (1.2 g, 50 mmol). The mixture was stirred at 25° C. for one hr. then refluxed for 5 hr. After cooling to 25° C., the mixture was poured onto ethyl acetate (200 mL) and the solution was washed with 1 M HCl (3×50 mL) then sat'd aq. NaCl (1×50 mL) and dried over sodium sulfate. The solvent was removed and the crude acid azeotroped once with toluene. The crude material was dissolved in 100 mL toluene, 10 mL (1.63 g, 14 mmol) thionyl chloride was added, and the mixture was refluxed for 90 min. The volume of the solution was reduced to approx. 30 mL by distillation, hen the remaining toluene was removed by evaporation.

c) The crude cid chloride from Step (b) was dissolved in 20 mL dry DCM and cooled to −70° C. under argon and a solution of approx. 10 mmol diazomethane in 50 mL anhydrous ether was added. The mixture was warmed to r.t. and stirred for 90 min. Argon was bubbled through the solution for 10 min., then the solvents were removed by evaporation and the crude material was purified by flash chromatography, eluting with 10–20% ethyl acetate in hexane. The diazoketone (0.85 g, 1.4 mmol, 82% yield over three steps) was obtained as a pale yellow solid.

In alternate Step (c) there is a change to the final diazomethylation step, whereby the acid chloride is reacted with (trimethylsilyl)diazomethane and triethylamine to give the identifier, which can then be used without further purification. With this alternate step, the identifier can be obtained in high yield with no chloromethylketone byproduct. Also, purification by flash chromatography is no longer necessary, which in some cases has resulted in significant acid-catalyzed decomposition of the identifier.

Alternate Step c). To a solution of the acid chloride (3.8 mmol, 1.00 equiv.) and 1.85 mL (13.3 mmol, 3.50 equiv.) of triethylamine in anhydrous THF/acetonitrile (1:1) at 0° C. under argon was added 5.7 mL (11.4 mmol, 3.00 equiv.) of a 2.0 M solution of (trimethylsilyl)diazomethane in hexanes. The resulting orange solution was stirred at 0° C. for 2 hr, then at 25° C. for 17 hr. (If a precipitate formed immediately upon addition of (trimethylsilyl)diatomethane, CH$_2$Cl$_2$ was added until the precipitate redissolved). EtOAc was added (250 mL), and the organic layer washed with saturated aq. NaHCO$_3$ (100 mL) and H$_{2O}$ (100 mL), then dried (anhydrous MgSO$_4$). Removal of the volatiles in vacuo gave the product as yellow crystals in 60–100% yield.

The other 11 identifiers of Formula IV were prepared by analogous synthetic routes, steps (a), (b), and (c).

In the synthesis of Example 1, the 12 identifiers were used to encode the combinatorial library. In Step 1, pentachlorophenyl identifiers where n=11–12 (abbreviated C$_{11}$Cl$_5$ and C$_{12}$C$_5$ were used in the following binary encoding scheme: 01=(n=12) and 10=(n=11). In Step 2, pentachlorophenyl identifiers where n=8–10 (abbreviated C$_8$Cl$_5$, C$_9$Cl$_5$, and C$_{10}$Cl$_5$) were used and encoded as follows: 001=(n=10), 010=(n=9), and 100=(n=8). In Step 3, pentachlorophenyl identifiers where n=3–7 (abbreviated C$_3$Cl$_5$, C$_4$Cl$_5$, C$_5$Cl$_5$, C$_6$Cl$_5$, and C$_7$Cl$_5$,) were used and encoded as follows: 00001=(n=7), 00010=(n=6), 00100=(n=5), 01000=(n=4), and 10000=(n=3). In Step 4, trichlorophenyl identifiers where n=5–6 (abbreviated C$_5$Cl$_3$ and C$_4$Cl$_3$) Were used and encoded as follows: 01=(n=6) and 10=(n=5).

Thus, in Step 1 reagent 3 (Table 1-1) is encoded "11" which represents tagging this choice in the synthesis with the two pentachloro-phenyl identifiers where n=11 and 12.

However, hydrazinolysis using hydrazine hydrate in MeOH at 25° C. produces t-butyl 4-(hydroxymethyl)-3-nitrobenzoate in high yield. Using MeOH as solvent, only the desired final product is obtained in near quantitative yield (93%).

t-butyl 4-(hydroxymethyl)-3-nitrobenzoate: To a solution of 14.1 g (47.7 mmol, 1.00 equiv.) of t-butyl 4-(acetoxymethyl)-3-nitrobenzoate in MeOH (200 mL) was added 27.0 mL (477 mmol, 10.0 equiv.) of hydrazine hydrate (55% hydrazine). The resulting yellow solution was stirred at 25° C. for 4 hr. EtOAc (250 mL) and saturated aq. NaCl (85 mL) were added, and the organic layer collected after shaking.

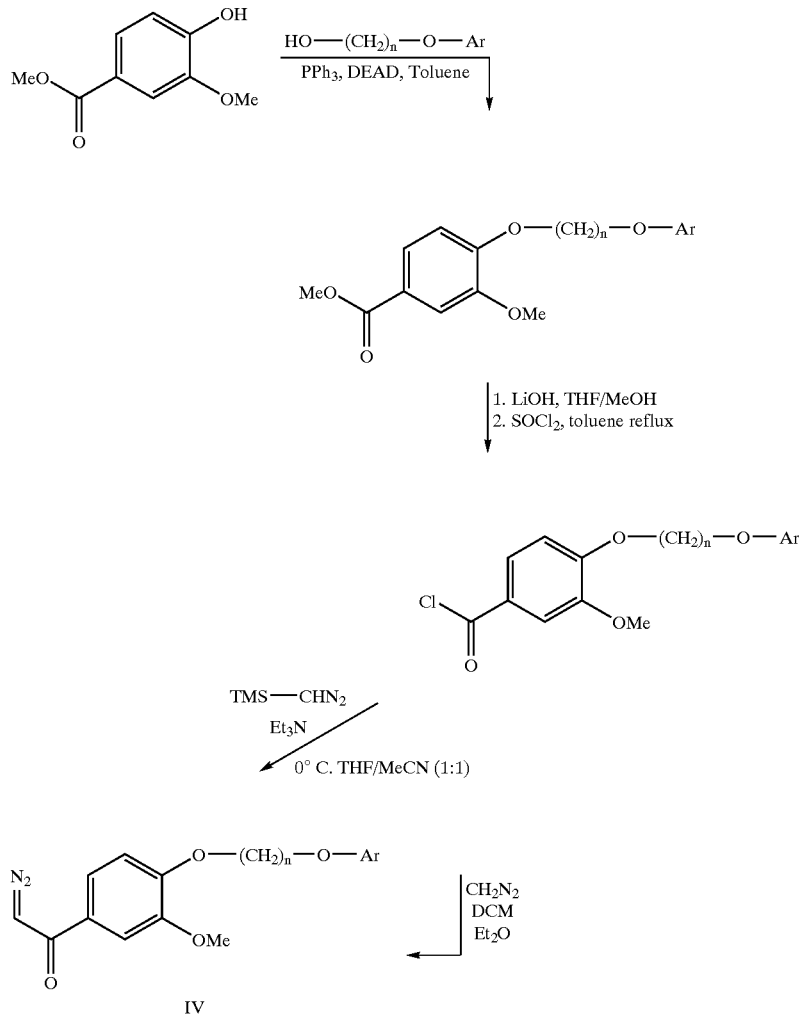

SCHEME 13
IDENTIFIERS

PREPARATION 2

T-BUTYL 4-(HYDROXYMETHYL)-3-NITROBENZOATE t-Butyl 4-(acetoxymethyl)-3-nitrobenzoate was prepared as described by Barany and Albericio, *J. Am. Chem. Soc.* 1985, 107 4936–4942. The reference's final procedure for hydrazinolysis of the acetate using hydrazine hydrate in ChCl$_3$ at 25° C. produces only trace amounts of the desired hydroxymethyl final product, which is the t-butyl ester pre-cursor of the photocleavable linker used herein.

The organic layer was washed further with saturated aq. NaCl (2×85 mL), and then dried (MgSO$_4$). Removal of volatiles in vacuo gave the product in 93% yield as yellow crystals.

PREPARATION 3

ALLYL 4-(HYDROXYMETHYL)-3-NITROBENZOATE

In a 100 mL round bottom flask was placed 4-hydroxymethyl-3-nitrobenzoic acid (1.97 g, 10 mmol).

Allyl alcohol (20 mL) was added, followed by p-toluensesulfonic acid (0.190 g, 1 mmol). The mixture was heated to reflux for 24 hr., at which time all the volatiles were removed in vacuo. The residue was taken up in EtOAc and washed with sat'd $KHCO_3$. The organic layer was dried over $MgSO_4$ and concentrated to afford the title compound as a cream colored solid; 2.4 g (100%).

PREPARATION 4

METHYL 4-(HYDROXYMETHYL)-3-NITROBENZOATE

Following the procedure of Preparation 3, but using methanol instead of allyl alcohol, the title compound was prepared in 57% yield.

PREPARATION 5

BIS-LINKER MODIFIED RESIN

Step 1 Addition of bis-Boc lysine

In a 250 mL synthesis vessel was placed bis-Boc-(L)-lysine (7.71 g, 22.2 mmol) as a solution in DMF (150 mL). HOBt (2.4 g, 21.0 mmol) was added followed by DIC (3.25 mL, 21.0 mmol) and the solution shaken at r.t. for 15 min. before adding TentaGel resin (25.8 g, approximately 7.2 mmol amino sites). The mixture was shaken at r.t. for 17 hr an then washed alternately wit methanol and DCM (5× each) and then with THF (2×) and dried under vacuum.

Step 2 Deprotection

Into each of seven 250 mL sythesis vessel was placed modified TentaGel resin (8.0 g, approx. 4.5 mmol of N-Boc amine sites). DCM (75 mL) was added followed by a 30% TFA solution in DCM (100 mL). The vessel was shaken at room temperature for 15 min before adding neat TFA (15 mL). The vessel was shaken at room temperature for 2.5 hr at which time the resin was washed with DCM (2×). The resin was then treated with a solution of 10% triethylamine in DCM (2×150 mL) shaking for 20 min. each time. The resin was then washed with DCM (4×) and DMF (1×).

PREPARATION 6 t-Boc-PROTECTED AMINO ACID

In a 1 L flask was placed 3-nitro-4-(bromomethyl)benzoic acid (20.03 g, 77.0 mmol). THF (300 mL) was added followed by 4-methoxybenzylamine (10.0 mL, 77.0 mmol) and triethylamine (35 mL). The resulting clear solution was stirred at r.t. for 17.5 hr. Solid ditert-butyl dicarbonate (16.8 g, 77.0 mmol) was added, followed by DMF (100 mL) and the resulting suspension stirred at r.t. for 72 hr. The reaction mixture was concentrated in vacuo and the residue taken up in ethyl acetate, washed with N HCl (×2), dried ($Na_2SO_4$), filtered and concentrated to afford a dark brown oil. Purification via flash chromatography (ethyl acetate:hexane) resulted in a yellow foam which was triturated with acetonitrile to give the expected protected amino acid (Table 2-1, compound 4) as a fine white powder (9.91 g, 31%).

PREPARATION 7 t-Boc-PROTECTED AMINO ACID

Substantially following the procedure of Preparation 6, but substituting the appropriate amine for 4-methoxybenzylamine, the remaining compounds of Table 2-1 are prepared.

EXAMPLE 1

1299 Compound Library

Step 1 a) $R^1/R^2$

To a solution of t-butyl 4-hydroxymethyl-3-nitrobenzoate (2 g, 7.89 mmol, 1 equiv.), 2,4-diydroxyacetophenone (1.20 g, 7.89 mmol, 1 equiv.), and triphenylphosphine (2.69 g, 10.26 mmol, 1.3 equiv.) in toluene (20 mL) was added dropwise DEAD (1.79 g, 10.26 mmol, 1.3 equiv.). After addition was complete the mixture was stirred for 16 hours at room temperature. The solvent was removed in vacuo and the residue was purified by flash chromatography ($SiO_2$, eluted with 10% ethyl acetate in hexanes) affording 1.47 g of the product (48% yield).

The t-butyl ester (500 mg, 1.29 mmol, 1 equiv.) above was dissolved/suspended in DCM (8 mL) and treated with TFA (3 mL). The mixture was stirred at room temperature for 8 hours. The DCM and TFA were removed in vacuo affording a white solid. This was azeotroped once with toluene then dried in vacuo affording 427 mg (look yield) of the carboxylic acid.

The acid (636 mg, 1.92 mmol, 1.5 equiv.) prepared above was dissolved in DMF (40 mL) and added to divinylbenzene-cross-linked, polyethyleneglycol-grafted polystyrene beads (TentaGel® S $NH_2$, Rapp Polymere) (4.0 g, 0.32 mmol/g, 1.28 mmol, 1 equiv.) in a Merrifield reaction vessel. The resin was suspended by agitation, then HOBt (259 mg, 1.92 mmol, 1.5 equiv.) and DIC (0.31 mL, 1.92 mmol, 1.5 equiv.) were added in that order. The resin was agitated at room temperature for 7 hours at which time it gave a negative Kaiser test. The resin was filtered and washed (DMF 3×50 mL, DCM 3×50 mL) then dried in vacuo.

The two other dihydroxyacetophenones were attached to the resin via the photocleavable linker in an analogous manner using the reagents of Table 1-1.

Alternate a)

In an analogous fashion the allyl and methyl esters were prepared from allyl 4-hydroxymethyl-3-nitrobenzoate (Preparation 3) and methyl 4-hydroxymethyl-2-nitrobenzoate (Preparation 4).

In a 10 mL flask was placed the allyl ester (110 mg. 0.3 mmol). Methylene chloride (2 mL) was added followed by tetrakis-triphenylphospine palladium(0) (11.5 mg, 0.01 mmol) and the mixture cooled to 0° C. Pyrrolidine (50 mL, 0.6 mmol) was added and the reaction stirred at 0° C. for 45 min. The mixture was diluted with EtOAc (10 mL) and washed with 3.5N HCl. The organic layer was dried ($MgSO_4$), filtered, and concentrated to afford a yellow solid; 90.6 mg.

In an analogous manner the methyl ester was deprotected by basic hydrolysis using a mixture of dilute NaOH and THF.

b) Encoding of Step 1

Quantities of the three resin batches (2.5 g) from Step 1(a) were placed in a separate synthesis vessels and each was suspended in DCM (20 mL). The three appropriate binary coding mixtures (Table 1-1) for each batch of resin were prepared by dissolving the appropriate choice (37.5 mg) or choices (37.5 mg of each) of $C_{12}Cl_5$ and $C_{11}Cl_5$—linker diazoketone (Preparation 1) in DCM (1 mL for each solution). These solutions were added to the appropriate synthesis vessel and the resin was agitated for 30 mins.

Rhodium trifluoroacetate dimer (1 mL of a 1 mg/mL solution in DCM) was added to each of the vessels and the resin was agitated at room temperature for 4 hours. Each batch of resin was then filtered and washed with DCM (2×20 mL) then each was resuspended in DCM (20 mL) and treated a second time with the appropriate binary encoding mixture as described above. The resin was again agitated for 30 mins before addition of the rhodium triflouroacetate dimer. The same quantities of catalyst and diazoketone compounds were used in the second coupling step as in the first. The resin was agitated for 14 hours. Each resin batch was then washed with DCM (5×20 mL) then the batches were combined and the entire library (three compounds) was washed with DCM (10 ×50 mL).

Step 2 a) Cyclocondensation Reactions

The dried resin from Step 1(b) was divided into four batches of 1.5 g (ca. 0.42 mmol) and three additional batches of 0.2 g (ca. 0.056 mmol). The 1.5 g batches were placed into 25 mL round-bottomed flasks and the 0.2 g batches were placed into 5 mL round-bottomed flasks. The portions of resin were suspended in methanol (15 mL in the four flasks with 1.5 g of resin, 2 mL in the three flasks with 0.2 g of resin) and pyrrolidine (0.6 mL, 7.2 mmol, ca. 15 equiv. in the flasks with 1.5 g of the resin; 0.08 mL, 0.96 mmol, ca. 15 equiv. in the flasks with 0.2 g of resin) was added to each flask. The reaction vessels were then all-owed to stand for 5 mn. to allow mixing of the reagents. The appropriate ketone (>10 equiv.) was then added t the vessels. The four BOC protected aminoketones were added to the flasks containing 1.5 g of resin and the other ketones were added to the flasks containing the 0.2 g of resin. The mixtures were heated at 75° C. for 16 hr. The flasks were then cooled to room temperature and each batch of resin was poured into a separate sintered funnel and washed thoroughly with DMF (3×20 mL) and DCM (3×20 mL).

b) Encoding of Step 2

Each batch of resin from Step 2(a) was placed into a separate synthesis vessel and was suspended in DCM (5 mL for the batches of 1.5 g of resin, 1 mL for the batches containing 0.2 g of resin). The seven appropriate binary coding mixtures (see Table 1-2) for each batch of resin were prepared by dissolving the appropriate choice (22.5 mg if added to a batch of 1.5 g of resin; 3.0 mg if added to a batch of 0.2 g of resin) of $C_{10}Cl_5$, $C_9Cl_5$, and $C_9Cl_5$ linker-diazoketone (Preparation 1) in DCM (1 mL for each solution). These solutions were added to the appropriate synthesis vessel and the resin was agitated for 30 mins.

Rhodium triflouroacetate dimer (1 mL of a 1 mg/mL solution in DCM) was added to each of the vessels and the resin was then filtered and washed with DCM (2×20 mL) then each was resuspended in DCM (5 mL for the hatches of 1.5 g of resin, 1 mL for the batches c 0.2 g of resin) and treated a second time with the appropriate binary encoding mixture as described above. The resin was again agitated for thirty mins before addition of the rhodium trifluoroacetate dimer. (The same quantities of catalyst and diazoketone compounds were used in the second coupling step as in the first.) The resin was then agitated for 16 hr. Each resin batch was then washed with DCM (5×20 mL). The four batches of 1.5 g of resin were combined and washed with DCM (10×50 mL). These combined batches were then reacted further in Step 3.

The three batches of 0.2 g of resin were combined and washed with DCM (10×20 mL). These combined batches were not used in Step 3 but were saved for Step 4.

Step 3 a) Encoding of Step 3

The four batches of 1.5 g of resin which had been combined in Step 2(b) were now divided into thirty lots of 170 mg each in 1 dram shell vials (Fisher Scientific) and each was suspended in DCM (2 mL). The thirty appropriate binary coding mixtures (see Table 1-3) for each batch of resin were prepared by dissolving the appropriate choice (3 mg) or choices of (3 mg of each) of $C_7Cl_5$, $C_6Cl_5$, $C_5Cl_5$, $C_4Cl_5$, and $C_3Cl_5$ linker-diazoketone (Preparation 1) in DCM (1 mL for each solution). These solutions were added to the appropriate synthesis vessel and the resin was agitated for 30 mins.

Rhodium trifluoroacetate dimer (1 mL of a 1 mg/mL solution in DCM) was added to each of the vessels and the resin was agitated at room temperature for 4 hr. The supernatant solution was then decanted away from the resin with a Pasteur pipette. The resin was washed twice with DCM (3 mL) and the washing removed by Pasteur pipette. Each batch of resin was resuspended in DCM (2 mL) and treated a second time with the appropriate binary encoding mixture as described above. The resin was again agitated for thirty minutes before addition fo the rhodium trifluoroacetate dimer. (The same quantities of catalyst and diazoketone compounds were used in the second coupling step as in the first.) The batches of resin were then agitated for 16 hr. Each resin batch was then transferred to a small Merrifield reaction vessel and washed with DCM (3×15 mL), DMF (2×15 mL), and DCM again (2×15 mL).

b) Deprotection

Each batch of resin was treated with a 50% solution of TFA in DCM (6 mL:6 mL). The resin was agitated for 2 hr and then filtered and washed with DCM (3×15 mL). The resin was then treated with a 10% solution of triethylamine in DCM (1 mL:9 mL) and agitated for 10 mins. This treatment was repeated once. The resin was filtered and washed with DCM (4×10 mL).

c) Addition of $R^6$

To each of the first six flasks was added DCM (5 mL) and the resin was agitated for 10 mins. 2,6-Lutidine (0.11 mL, 20 equiv.) was added to each flask followed by a solution of the appropriate chloroformate (Table 1-3) in DCM (5 mL) and the resin was agitated for 4 hr. Except for isopropylchloroformate (Aldrich), the chloroformates were prepared from the appropriate alcohols by treating the alcohols (0.1 g) with a solution of phosgene in toluene (5 mL of a 1.8 solution) for 1 hr, then evaporating to dryness in vacuo, and redissolving in DCM (5 mL).

To flasks 8,9, and 10 was added ethanol (10 mL) and the appropriate isocyanate (Table 1-3) (0.1 mL, ca. 10 equiv.) and the resin was agitated for 4 hr.

To flasks 11, 12, and 13 was added ethanol (10 mL) and the appropriate isothiocyanate (0.1 mL, 0.1 g of the naphthalene-isothiocyanate, ca. 10 equiv.) and the resin was agitated for 4 hr.

To flasks 7 and 14–22 was added DMF (10 mL) and the appropriate carboxylic acid (ca. 10 equiv.) and HOBt (0.103 g, ca. 15 equiv.). The flasks were agitated for 30 mins then DIC (0.12 mL, ca. 15 equiv.) was added to each flask and the resin was agitated for 4 hr.

To flask 23–30 was added to DCM (10 mL) and triethylamine (0.15 mL, ca. 15 equiv.) and the resin was agitated for 15 mins. The appropriate sulfonyl chloride (ca. 10 equiv.) was added to the reaction vessels and the resin agitated for 4 hr.

The flasks were filtered and the resin washed with DCM (3×10 mL). All of the resin was combined in one large synthesis vessel and was washed with DCM (3×50 mL), DMF (3×50 mL), and DCM again (3×50 mL). The resin was dried in vacuo.

Alternative Step 3 a) Encoding of Alternative Step 3

The remaining 900 mg of resin from the four combined batches of 1.5 g from Step 2(b) which had not been used in Step 3 was divided into ten portions of 90 mg, and each portion placed in a separate 1 dram shell vial (Fisher Scientific). The ten appropriate binary coding mixtures (see Table 1-5) for each batch of resin were prepared by dissolving the appropriate choice (1.5 mg) or choices (1.5 mg for each) of $C_7Cl_5$, $C_5Cl_5$, $C_4Cl_5$, and $C_3Cl_5$ linker-diazoketone (Preparation 1) in DCM (1 mL for each solution). These solutions were added to the appropriate synthesis vessels and the resin was agitated for 30 min.

Rhodium trifluoroacetate dimer (1 mL of a 1 mg/mL solution in DCM) was added to each of the vessels and the resin was agitated at room temperature for 4 hr. The supernatant solution was then decanted from the resin. The resin was washed (DCM 2×3 mL) and the washing removed by Pasteur pipette. The resin was then treated a second time with solutions of the appropriate binary coding mixtures and agitated for 30 min. before the addition of the rhodium trifluoroacetate dimer. The same quantities of catalyst and diazoketone compounds were used in the second coupling as in the first. The batches of resin were then agitated for 16 hr. The resin was then transferred into small Merrifield synthesis vessels and washed (DCM 6×15 mL).

b) Deprotection.

Each batch of resin was treated with a solution of TFA in DCM (4 mL:4 mL). The resin was agitated for 1 hr, then filtered and washed with DCM (2×15 mL). The resin was then treated with a solution of piperidine in DCM (4 mL:4 mL) and agitated for 15 min. This treatment was repeated once. Each batch of beads was washed with methanol (2×15 mL) and DCM (4×15 mL). Flasks 1–4 were washed with T1F (3×15 mL).

c) Heteroarylation Reactions

The resin in flasks 1–4 was suspended in THF (6 mL). Flasks 1–3 were then treated with DBU (190 µL, ca. 40 equiv.) followed by the appropriate heteroaryl chloride (ca. 20 equiv.). Flasks 1 and 2 were heated at 55° C. for 16 hr. Flask 3 was heated at reflux for 16 hr. Flask 4 was treated with triethylamine (700 µL) and the appropriate heteroaryl chloride (ca. 20 equiv.). The resin was shaken at r.t. for 16 hr. Each batch of resin was then washed in THF (2×15 mL) and dried in vacuo.

d) Reductive Alkylations

The resin in flasks 5–10 was suspended in DMF (8 mL) and the appropriate aldehyde (ca. 67 equiv.) added. Acetic acid (160 µL) was added to each of the flasks followed by sodium cyanoborohydride (ca. 67 equiv.). Flasks 5, 6, 7, 9, and 10 were shaken at r.t. for 16 hr. Flask 8 was heated to 55° C. for 16 hr. Each batch of resin was filtered and washed with DMF (3×15 mL). Each of the reductive alkylation reactions was repeated under the same conditions. The batches of resin were washed with DMF (2×15 mL), methanol (3×15 mL), and DCM (3×15 mL). The resin was then mixed, washed with DCM (2×20 mL), and dried in vacuo.

This part of the library did not undergo further elaboration.

Step 4 a) Encoding of Step 4

To the combined resin from Step 3(c) was added 45 mg of resin from each of the seven flasks from Step 2(b) and the resin was washed and mixed thoroughly with DCM (3×50 mL). From this mixture was weighed out three portions of 800 mg of resin and these were placed into three separate Merrifield synthesis vessels and suspended in DCM (10 mL). The three appropriate binary coding mixtures (see Table 1-4) for each batch of resin were prepared by dissolving the appropriate choice (24 mg) or choices (24 g of each) of the $C_4Cl_3$ and $C_5Cl_3$ linker-diazoketone compound in DCM (1 mL for each solution). These solutions were added to the appropriate synthesis vessel and the resin was agitated for 30 mins.

Rhodium trifluoroacetate dimer (1 mL of a 1 mg/mL solution in DCM) was added to each of the vessels and the resin was agitated at room temperature for 4 hr. Each batch of resin was then filtered and washed with DCM (2×20 mL) then each was resuspended in DCM (10 mL) and treated a second time with the appropriate binary encoding mixture as described above. The resin was again agitated for 30 mins before addition of the rhodium trifluoroacetate dimer. The same quantities of catalyst and diazoketone compounds were used in the second coupling step as in the first. The resin was agitated for 14 hr. Each resin batch was then washed with DCM (3×20 mL) and then filtered.

b) Carbonyl Reaction (Addition of $R^6$ and $R^7$)

The resin in flask 1 was resuspended in DCM (6 mL) and 1,2-ethanedithiol (1 mL) and boron trifluoride etherate (1 mL) were added. The flask was shaken at room temperature for 6 hr. The resin was then washed with DCM (20 mL) and then resuspended in DCM (6 mL) and treated once more with ethanedithiol (1 mL) and boron trifluoride etherate (1 mL). The resin was agitated at room temperature for 14 hr. The resin was then filtered and washed with DCM (5×20 mL).

The resin in flask 2 was suspended in methanol (5 mL) and solid sodium borohydride (200 mg) was added cautiously. The flask was vented and allowed to shake gently for 1 hr. The resin was filtered and resuspended in methanol and the reduction process repeated a total of 5 times at 1 hr intervals using 200 mg of sodium borohydride each time. After the final cycle the resin was washed with methanol (3×20 mL) and DCM (3×20 mL).

The resin in flask 3 was not reacted further.

The resin from the three flasks was combined and washed with DCM (5×50 mL) and then dried in vacuo. A portion (500 mg) of the resin was suspended in DCM (5 mL) and TFA (5 mL) and shaken for 2 hr. The resin was then treated twice with a 10% solution of triethylamine in DCM (10 mL) and washed with DCM (5×20 mL). The resin was then dried in vacuo.

d) Decoding Procedure

A bead was placed in a 1.13 am diameter pyrex capillary with 2 µL of acetonitrile. Ceric ammonium nitrate solution (2 µL of a 0.1 M aq. solution) and hexane (3 µL) were added and the two-phase mixture centrifuged briefly. The tube was sealed and left at 35° C. for 16 hrs, then opened. The organic layer was removed by syringe and mixed with 1 µL of N,O-bis(trimethylsilyl)acetamide. The silated tag solution (1 µL) was anlayzed by GC with electron capture (EC) detection.

The GC analysis was performed with a Hewlett Packard 5890 plus gas chromatograph. On column injection into a 5 m, 0.32 mm retention gap connected to a 25 m, 0.2 mm crosslinked s5 phenylmethyl silicone column was used. The temperature program was set at 200° C. for 1 min and then increased at a rate of 15° C./min from 200–300° C. The pressure program was set at 20 psi for 1 min, then increased at 2 psi/min to 40 psi with a total run time of 10 min. The EC detector was maintained at 400° C. and the auxiliary gas was set at 35 psi.

TABLE 1-1
$R^1/R^2$ Reagents and Encoding Scheme
1.01 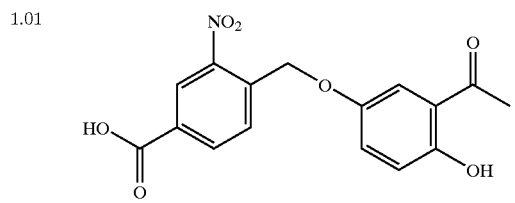
2.10 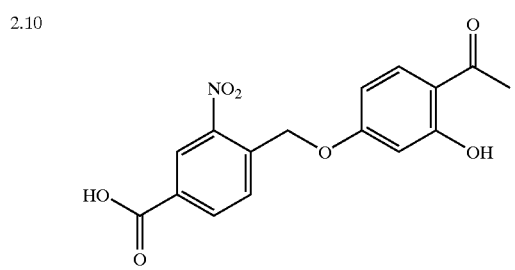
3.11 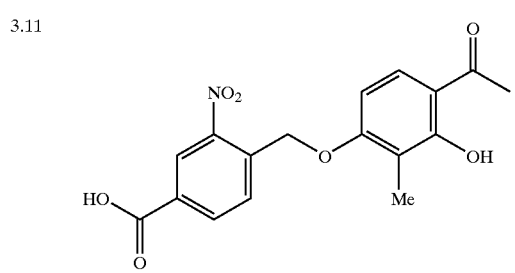
TABLE 1-2
$R^4/R^5$ Reagents and Encoding Scheme
1.001 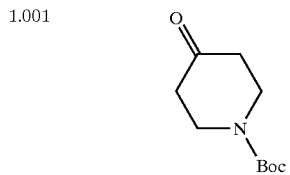
2.010 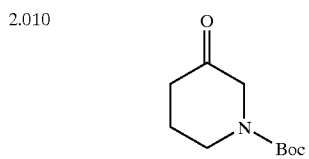
3.011 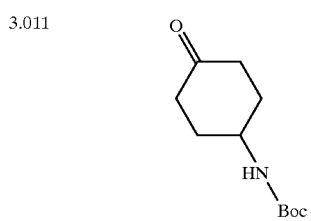
TABLE 1-2-continued
$R^4/R^5$ Reagents and Encoding Scheme
4.100 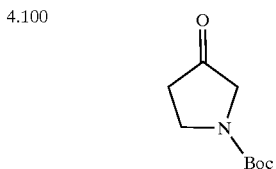
5.101 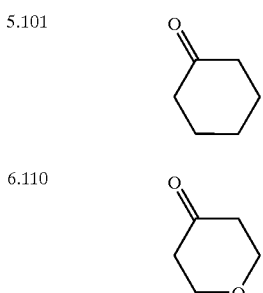
6.110 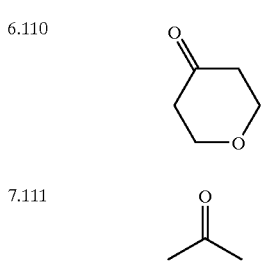
7.111 
TABLE 1-3
$R^8$ Reagents and Encoding Scheme
1.00001 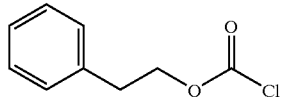
2.00010 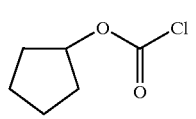
3.00011 CH₂CHCH₂ 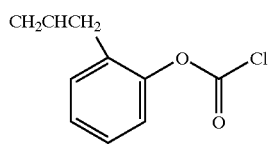
4.00100 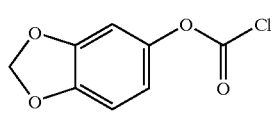
5.00101 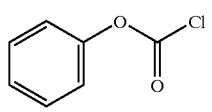
6.00110 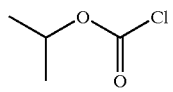
7.00111 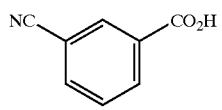

TABLE 1-3-continued

R⁸ Reagents and Encoding Scheme

| # | Structure |
|---|---|
| 8.01000 | phenyl-N=C=O |
| 9.01001 | 4-Cl-phenyl-N=C=O |
| 10.01010 | 4-F₃C-phenyl-N=C=O |
| 11.01011 | benzyl-N=C=S |
| 12.01100 | phenyl-N=C=S |
| 13.01101 | 1-naphthyl-N=C=S |
| 14.01110 | hydantoin-CH₂CO₂H (2,4-dioxoimidazolidin-5-yl acetic acid) |
| 15.01111 | 2,6-dioxohexahydropyrimidin-4-yl-CO₂H |
| 16.10000 | indol-3-yl-CH₂CO₂H |
| 17.10001 | 2-oxothiazolidin-4-yl-CO₂H |
| 18.10010 | imidazol-4-yl-CH₂CO₂H |
| 19.10011 | phenyl-CH₂CO₂H |
| 20.10100 | 2-biphenyl-CO₂H |
| 21.10101 | benzoic acid |
| 22.10110 | 4-(H₂NO₂S)-benzoic acid |
| 23.10111 | 1-naphthyl-SO₂Cl |
| 24.11000 | 2-naphthyl-SO₂Cl |
| 25.11001 | 4-Cl-phenyl-SO₂Cl |
| 26.11010 | 4-Me-phenyl-SO₂Cl |
| 27.11011 | phenyl-SO₂Cl |
| 28.11100 | n-butyl-SO₂Cl |
| 29.11101 | isopropyl-SO₂Cl |
| 30.11110 | 4-t-Bu-phenyl-SO₂Cl |

TABLE 1-4

R⁶/R⁷ Reagents and Encoding Scheme

| | |
|---|---|
| 1.01 | HS(CH₂)₂SH/BF₃·OEt₂ |
| 2.10 | NaBH₄ |
| 3.11 | No reaction |

TABLE 1-5

R¹⁴ and Heteroaryl Encoding Scheme

| Code | Structure |
|---|---|
| 1.0001 | 2-chloropyrimidine |
| 2.0010 | 2-amino-4,6-dichloropyrimidine |
| 3.0011 | 3,6-dichloropyrazine (dichloropyrazine) |
| 4.0100 | 2,3,6,7-tetrachloroquinoxaline |
| 5.0101 | 4-fluorobenzaldehyde |
| 6.0110 | 4-methoxybenzaldehyde |
| 7.1000 | benzaldehyde |
| 8.1100 | 4-pyridinecarboxaldehyde |
| 9.1010 | butyraldehyde (propyl-CHO) |
| 10.1001 | cyclopropanecarboxaldehyde |

EXAMPLE 2

87,906 Compound Library

Step 1 a) Addition of $(CH_2)_{1-6}R^{17}$

In a 250 mL synthesis vessel was placed the deprotected modified TentaGel resin (8.0 g, approx. 4.5 mmol of amine sites) from Preparation 5. HOBt (1.81 g, 13.4 mmol) was added followed by the N-Boc-p-methoxybenzylamino acid (Table 2-1, compound 4) (5.60 g, 13.4 mmol) and DMF (150 mL). The mixture was shaken at r.t. for 16 hr and then washed alternately with methanol and DCM (4× each) and then with EtOAc (2×). Analysis of the resin via the standard Kaiser ninhydrin test indicated that the coupling reaction was complete.

In six separate vessels, analogous couplings were carried out with the six other Boc-protected amino acids listed in Table 2-1. All coupling reactions were repeated until satisfactory Kaiser ninhydrin test results were obtained (in all cases either one or two couplings).

b) Encoding of Step 1

While still in their separate 250 mL synthesis vessels, resin batches number 4, 5, 6, and 7 from Step 1 were suspended in EtOAc (100 mL). Into each of these four vessels was placed the $Cl_5C_7$-linker diazoketone (0.56 g) and the mixtures agitates for 1 hr. To each of the four vessels was then added rhodium trifluoroacetate dimer (6 mL of a 1 mg/mL solution in DCM) and the resin was agitated for 15 hr. The resin was then washed with DCM (4×) and EtOAc (2×).

In turn, the $Cl_5C_8$-linker diazoketone was applied to resin batches numbered 2, 3, 6, and 7. Applications of each tagging molecule was done separately and in analogous fashion to that or the $Cl_5C_7$-linker diazoketone outlined above. The seven batches of encoded resin were all combined in a 2 L Erlenmeyer flask along with THF (1 L) and mixed thoroughly by swirling and stirring gently with a glass rod. The resin was then recovered by filtration and vacuum dried.

Step 2: Addition of $R^2$ a) Deprotection

In a 250 mL synthesis vessel is placed mixed, encoded resin from Step 1 (9 g) along with DCM (just enough to suspend resin). TFA (75 mL of a 30% solution in DCM) is added and the resin agitated for 3.5 hr. The resin is then washed with DCM (2×) followed by treatment with 10% triethylamine in DCM (2×20 min. each) and then washed with DCM (4×).

b) Coupling

The deprotected resin from Step 2(a) (9 g) is suspended in DMF (7 mL). HOBt (2.04 g, 45 mmol) is added followed by the acetophenone acid (Table 2-2, compound 3) (3.36 g, 15 mmol) and the mixture agitated for 15 min. DIC (2.3 mL, 15 mmol) is added and the mixture agitated for 21 hr. The resin is washed alternately with DCM and methanol (5× each) and then with EtOAc (4×).

In five separate vessels, analogous couplings are carried out with the five other acetophenone acids listed in Table 2-2.

c) Encoding of Step 2

The six batches of resin from Step 2 are binarily encoded in a fashion analogous to that described above for encoding of step 1.

The six batches of encoded resin are combined in a 2 L Erlenmeyer flask along with THF (1 L) and mixed thoroughly by swirling and stirring gently with a glass rod. The resin is then recovered by filtration and vacuum dried.

Step 3 Addition of $R^4R^5$ a) Cyclocondensation Reactions

The mixed resin from Step 2 is divided into three batches of 14.4 g (ca. 8.1 mmol) and seven additional batches of 1.5 g (ca. 0.84 mmol). The 144 g batches are placed into 250 mL round bottom flasks and the 1.5 g batches are placed in 25 mL round bottom flasks. The portions of resin are suspended in methanol (150 mL in the three flasks with 14.4 g resin, 15 mL in the seven flasks with 1.5 g resin) and pyrrolidine (10.1 mL, 121 mmol, ca. 15 equiv. in the flasks with 14.4 g resin; 1.0 mL, 12.6 mmol, ca. 15 equiv. in the flasks with 1.5 g resin) is added to each flask. The reaction vessels are then allowed to stand for 15 min. to allow mixing of the reagents. The appropriate ketone (5 to 10 equiv.) is then added to the vessels. The three Boc-protected aminoketones from Table 2-3 are added to the flasks containing 14.4 g of resin and the seven other ketones, from Table 2-4, are added to the flasks containing 1.5 g of resin. The mixtures are heated at 75° C. for 16 hr. The flasks are then cooled to r.t. and each batch of resin is soured into a separate synthesis vessel of appropriate size and washed thoroughly with DCM, DMF, and methanol (alternating: 5× each).

b) Encoding of Step 3

Each of the ten batches of resin from Step 3(a) is binarily encoded in a fashion analogous to that described for encoding Step 1.

c) Mixing and Dividing The seven 1.5 g batches of encoded resin are combined in a 500 mL Erlenmeyer flask along with THF (250 mL) and mixed thoroughly by swirling and stirring gently with a glass rod. The resin is then recovered by filtration and vacuum dried. This combined resin is kept separate from the three 14.4 g batches of resin and is not subjected to the reaction conditions of Step 4, but rather re-divided into three 0.2 g portions and seven 1.4 g portions and saved to be used in Step 5 and alternate Step 5. The three 14.4 g batches of encoded resin are combined in a 2 L Erlenmeyer flask along with THF (1 L) and mixed thoroughly by swirling and stirring gently with a glass rod. The resin is then recovered by filtration, vacuum dried, and used in Step 4.

Step 4 a) Deprotection

Into each of seven 250 mL synthesis vessels is placed mixed, encoded resin from the three combined 14.4 g batches from Step 3 (6 g) along with DCM (just enough to suspend the resin) TFA (75 mL of a 30% solution in DCM) is added and the resin agitated for 3.5 hr. The resin is then washed with DCM (2×) followed by treatment with 10% triethylamine in DCM (2×20 min. each) and then washed with DCM (4×).

b) Nitrogen Elaboration

In the first of the seven 250 mL synthesis vessels containing deprotected resin from Step 4(a) (6 g, ca 3.4 mmol) is placed DCM (150 mL) and triethylamine (15 equiv.). Phenylsulfonyl chloride (ca. 10 equiv.) is added and the resin agitated for 4 hr. The resin is washed with alternating DCM and methanol (5× each) and then with EtOAc (2×).

In the second of the seven 250 mL synthesis vessels containing deprotected resin from Step 4(a) (6 g, ca 3.4 mmol) is placed DCM (150 mL) and triethylamine (15 equiv.). Butryl chloride (ca 10 equiv.) is added and the resin agitated for 4 hr. The resin is washed with alternating DCM and methanol (5× each) and then with EtOAc (2×).

In the third of the seven 250 mL synthesis vessels containing deprotected resin from Step 4(a) (6 g, ca. 3.4 mmol) is placed DMF (150 mL) and HOBt (ca. 15 equiv.). 4-Carboxy-benzenesulfonamide (ca 10 equiv.) is added and the resin agitated for 30 min. DIC (ca. 10 equiv.) is added and the resin agitated for 4 hr. The resin is washed with alternating DCM and methanol (5× each) and then with EtOAc (2×).

In the fourth of the seven 250 mL synthesis vessels containing deprotected resin from Step 4(a) (6 g, ca. 3.4 mmol) is placed DMF (150 mL) and acetic acid (3 mL). Benzaldehyde (ca 50 equiv.) is added and the resin agitated for 30 min. sodium cyanoborohydride (ca 50 equiv.) is added and the resin agitated for 16 hr. The resin is washed with alternating DCM and methanol (5× each) and then with EtOAc (2×).

In the fifth of the seven 250 mL synthesis vessels containing deprotected resin from Step 4(a) (6 g, ca 3.4 mmol) is placed DMF (150 mL) and acetic acid (3 mL). Butyraldehyde (ca 50 equiv.) is added and the resin agitated for 30 min. sodium cyanoborohydride (ca 50 equiv.) is added and the resin agitated for 16 hr. The resin is washed with alternating DCM and methanol (5× each) and then with EtOAc (2×).

The resin from the sixth of the seven 250 mL synthesis vessels containing deprotected resin from Step 4(a) (6 g, ca 3.4 mmol) is transferred to a 250 mL round bottom flask THF (150 mL) is added followed by DBU (ca 40 equiv.). 2-Chloropyrimidine (ca 20 equiv.) is added. The mixture is heated to 55° C. for 16 hr. The resin is transferred back to a 250 mL synthesis vessel, washed with alternating DCM and methanol (5× each), and then with EtOAc (2×).

In the seventh of the seven 250 mL synthesis vessels containing deprotected resin from Step 4(a) (6 g, ca 3.4 mmol) is placed absolute ethanol (150 mL). Methyl isocyanate (ca equiv.) is added and the resin agitated for 12 hr. The resin is washed with alternating DCM and methanol (5× each) and then with EtOAc (2×).

c) Encoding of Step 4

Each of the seven batches of resin from Step 4(b) are binarily encoded in a fashion analogous to that described for the encoding of Step 1.

The seven batches of encoded resin are combined in a 2 L Erlenmeyer flask along with THF (1 L) and mixed thoroughly by swirling and stirring gently with a glass rod. The resin is then recovered by filtration and vacuum dried. This resin is then divided into three batches of 0.7 g each and seven batches of 5.7 g each. The seven 5.7 g. batches are subjected to Seep 5. The three 0.7 g batches are subjected to alternate Step 5.

Step 5 a) Encoding

Each of the seven 5.7 g. batches of resin from Step 4(c) and the seven 1.4 g batches from Step 3(b) are binarily encoded in a fashion analogous to that described for the encoding of Step 1.

b) Reductive Amination

The seven encoded 5.7 g. batches of resin from Step 5(a) are placed in 200 mL round bottom flasks. The seven encoded 1.4 g. batches from Step 3(c) are placed in 50 mL round bottom flasks. To each of the fourteen flasks is added a solution of 1o0 glacial acetic acid in methanol (60 mL in the 200 mL flasks, 15 mL in the SO mL flasks). The appropriate amine for Table 2-6 (ca 40 equiv.) is added followed by sodium cyanoborohydride (ca 40 equiv.). Condensers are attached and the mixtures are heated to 75° C. for 48 hr. The resin is washed with alternating DCM and methanol (5× each) and then with EtOAc (2×).

Alternate Step 5 a) Thicketalization

One of the three 0.7 g. batches of resin from Step 4(c) and one of the 0.2 batches of resin from Step 3(c) are placed in two separate 30 mL synthesis vessels. To each is added DCM (6 mL), followed by 1,2-ethanedithiol (1 mL) and boron trifluoride etherate (1 mL). The resin is agitated at r.t. for 6 hr. The resin is washed with DCM (1×) and then treated once more with ethanedithiol (1 mL) and boron trifluoride etherate (1 mL). The resin is agitated at r.t. for 14 hr. The resin is then filtered and washed with alternating DCM and methanol (5× each) and then with EtOAc (2×).

b) Reduction

One of the three 0.7 g. batches of resin from Step 4(c) and one of the 0.2 g batches of resin from Step 3(c) are placed in two separate 30 mL synthesis vessels. To each is added methanol (6 mL) and (cautiously) solid sodium borohydride (200 mg). The flasks are vented and allowed to gently shake for 1 hr. The resin is filtered and resuspended in methanol (6 mL) and the reduction process repeated a total of 5 times at 1 hr. intervals using 200 mg portions of sodium borohydride each time. After the final cycle, the resin is washed with alternating DCM and methanol (5× each) and then with EtOAc (2×).

c)

One of the three 0.7 g. batches of resin from Step 4(c) and one of the 0.2 g batches of resin from Step 3(c) is left unaltered.

Step 6 a) Mixing

The seven 5.7 g batches of encoded resin from Step 5(b) are combined in a 2 L Erlenmeyer flask along with THF (1 L). The seven 1.4 g batches of encoded resin from Step 5(b) are combined in a 500 mL Erlenmeyer flask. Each batch of resin is mixed thoroughly by swirling and stirring gently with a glass rod. The resin from each flask is recovered by filtration, vacuum dried, and kept separate.

b) Nitrogen Elaboration

The mixed and dried resin from the combined 5.7 g. batches in Step 6(a) (total of ca 32.5 g.) is divided into ten 3.2 g. batches and placed in 100 mL synthesis vessels. The mixed and dried resin from the combined 1.4 g. batches in Step 6(a) (total of ca 9.8 g.) is divided into ten 0.98 g. batches and placed in 30 mL synthesis vessels. These vessels are paired up into ten sets of two where each set has one 100 mL vessel and one 30 mL vessel. Both members of each set are subjected to the same reaction conditions as outlined below.

In the first set of vessels is placed N,N'-bis Boc-(L)-lysine (ca 10 equiv.) as a solution in DMF 960 mL in the larger vessel, 15 mL in the smaller). HOBt (ca 15 equiv.) is added and the resin agitated for 15 min DIC (ca 10 equiv.) is added and the resin agitated for 4 hr. The resin is washed with DCM (2×) and then treated wish TFA (30% solution in DCM) (1.5 hrs.). The resin is then washed with DCM (2×) and treated with 10% triethylamine in DMF (2×, 30 min. each). The resin is washed with alternating DCM and methanol (5× each) and then with EtOAc (2×).

In the second set of vessels is placed N-α-Fmoc-N-ω-Pmc-(L)-arginine (ca 10 equiv.) as a solution in DMF (60 mL in the larger vessel, 15 mL in the smaller). HOBt (ca 15 equiv.) is added and the resin agitated for 15 min. DIC (ca 10 equiv.) is added and the resin agitated for 4 hr. The resin is washed with DCM (2×) and then treated with TFA (50% solution in DCM) (1.5 hrs.). The resin is the washed with DCM (2×) and treated with 50% piperidine in DMF (2×, 30 min. each). The resin is washed with alternating DCM and methanol (5× each) and then with EtOAc (2×).

In the third set of vessels is placed DCM (60 mL in the larger vessel, 15 mL in the smaller). N,N-di-n-propyl-N'-cyano-ethylthioformamidine (ca 15 equiv.) is added, followed by triethylamine (ca 20 equiv.) and the resin agitated for 12 hrs. The resin is washed with alternating DCM and MeOH (5×each) and then with EtOAc (2×).

In the fourth set of vessels is placed absolute ethanol (60 mL in the larger vessel, 15 mL in the smaller). Methyl isocyanate (ca 15 equiv.) is added and the resin agitated for 12 hr. The resin is washed with alternating DCM and methanol (5× each) and then with EtOAc (2×).

In the fifth set of vessels is placed absolute ethanol (60 mL in the larger vessel, 15 mL in the smaller). Methyl isothiocyanate (ca 15 equiv.) is added and the resin agitated for 12 hr. The resin is washed with alternating DCM and methanol (5× each) and then with EtOAc (2×).

In the sixth set of vessels is placed absolute ethanol (60 mL in the larger vessel, 15 mL in the smaller). Phenyl isocyanate (ca. 15 equiv.) is added and the resin agitated for 12 hr. The resin is washed with alternating DCM and methanol (5× each) and then with EtOAc (2×)

In the seventh set of vessels is placed absolute ethanol (60 mL in the larger vessel, 15 mL in the smaller). Phenyl isothiocyanate (ca. 15 equiv.) is added and the resin agitated for 12 hr. The resin is washed with alternating DCM and methanol 95× each) and then with EtOAc (2×)

In the eighth set of vessels is placed DCM (60 mL in the larger vessel, 15 mL in the smaller) and 2,6-lutidine (ca. 20 equiv.). Isopropyl chloroformate (ca 15 equiv.) is added and the resin agitated for 4 hr. The resin is washed with alternating DCM and methanol (5× each) and then with EtOAc (2×)

In the ninth set of vessels is placed DCM (60 mL in the larger vessel, 15 mL in the smaller) and triethylamine (15 equiv.). Isobutryl chloride (ca 10 equiv.) is added and the resin agitated for 4 hr. The resin is wastes with alternating DCM and methanol (5× each) and then with EtOAc (2×)

In the tenth set of vessels is placed DCM (60 mL in the larger vessel, 15 mL in the smaller) and triethylamine (15 equiv.). Methanesulfonyl chloride (ca 10 equiv.) is added and the resin agitated for 4 hr. The resin is washed with alternating DCM and methanol (5× each) and then with EtOAc (2×).

TABLE 2-1

$(CH_2)_{1-6}R^{17}$ Reagents and Encoding Scheme

1.

[Structure: 2-nitro-4-hydroxycarbonyl benzyl group with N(Me)-C(O)-O-tBu]

$Cl_5C_{11}$

2.

[Structure: 2-nitro-4-hydroxycarbonyl benzyl group with N(CH2CH2OMe)-C(O)-O-tBu]

$Cl_5C_8$

3.

[Structure: 2-nitro-4-hydroxycarbonyl benzyl group with N(CH2CH2Ph)-C(O)-O-tBu]

$Cl_5C_8$
$Cl_5C_{11}$

TABLE 2-1-continued
$(CH_2)_{1-6}R^{17}$ Reagents and Encoding Scheme
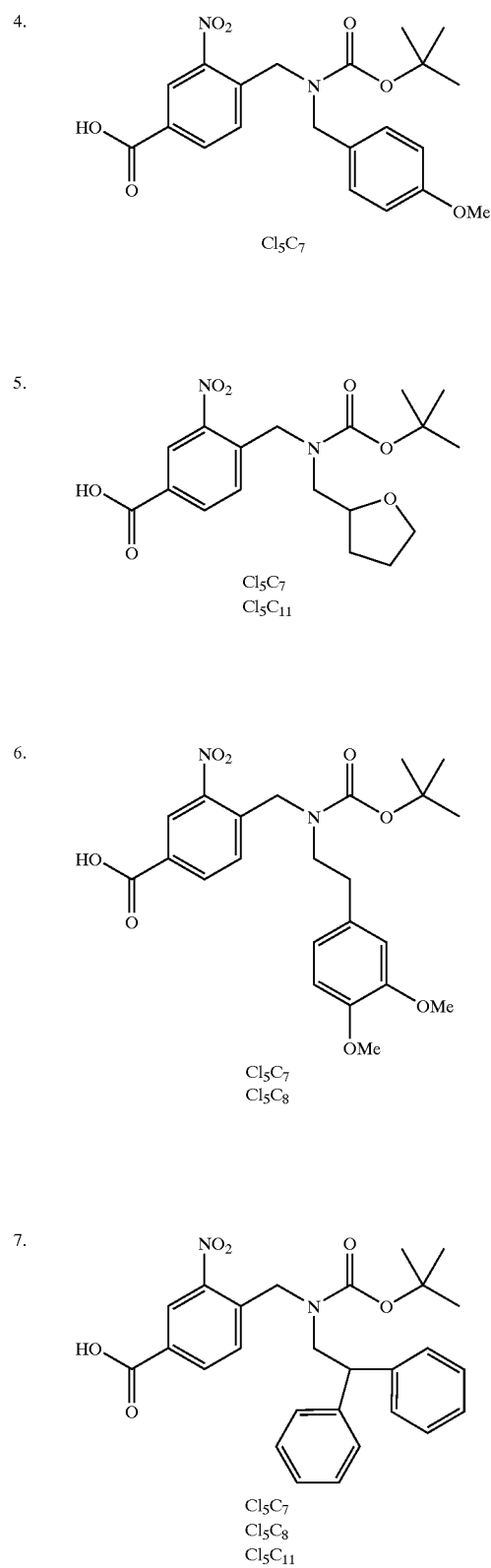
TABLE 2-2
Substituted Hydroxyacetophenone Reagents
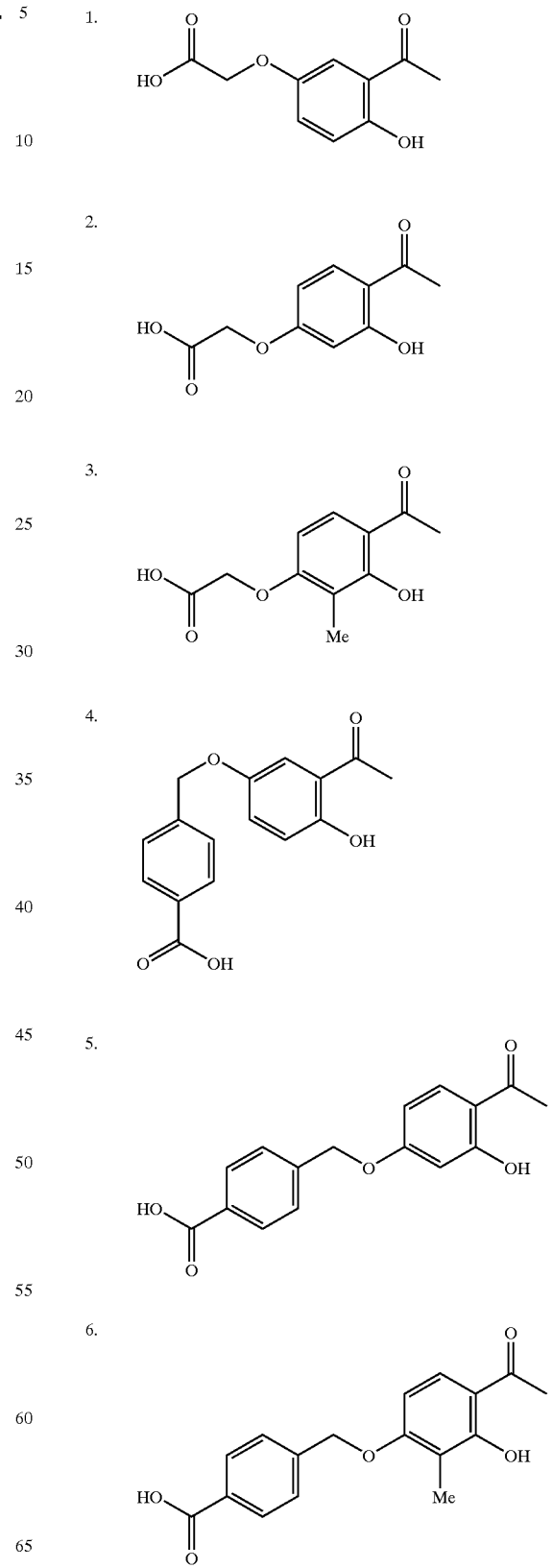

TABLE 2-3
R⁴R⁵ Step 3 Reagents
1. 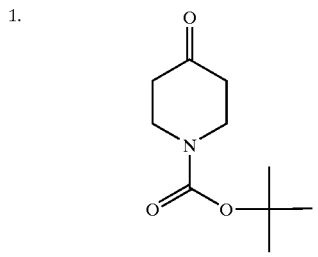
2. 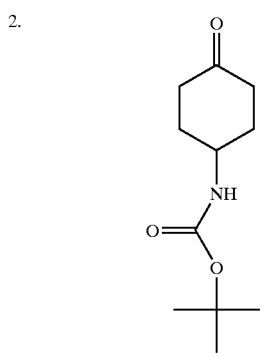
3. 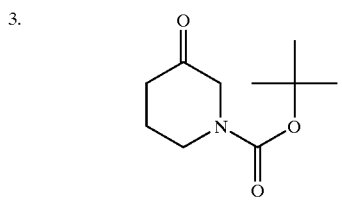
TABLE 2-4
R⁴R⁵ Step 3 Alt. Reagents
1. 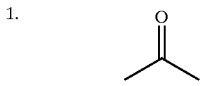
2. 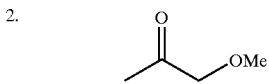
3. 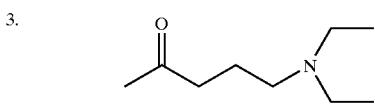
4. 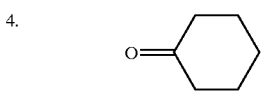
5. 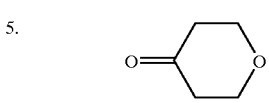
6. 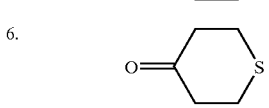
TABLE 2-4-continued
R⁴R⁵ Step 3 Alt. Reagents
7. 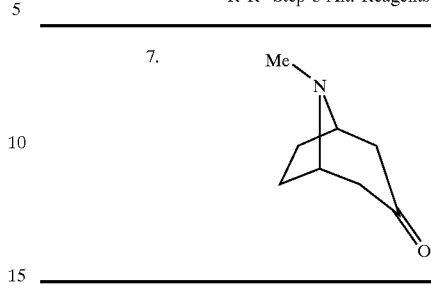
TABLE 2-5
R⁸ Reagents
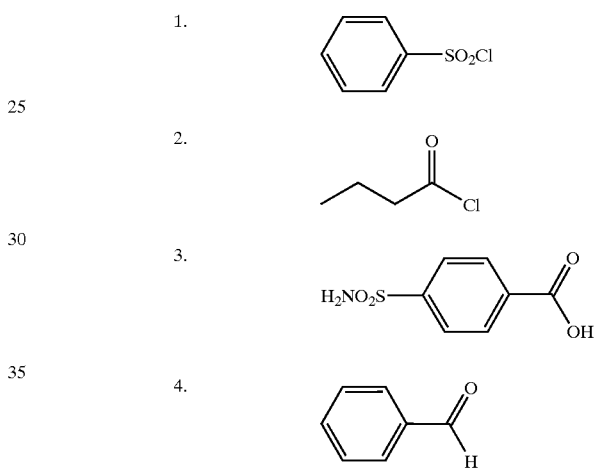
1. Ph-SO₂Cl
2. propanoyl chloride
3. H₂NO₂S-C₆H₄-COOH
4. benzaldehyde
5. butyraldehyde
6. 2-chloropyrimidine
7. Me—N=C=O
TABLE 2-6
(CH₂)₁₋₆R¹⁴ Reagents
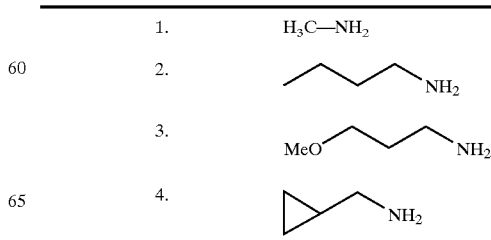
1. H₃C—NH₂
2. CH₃CH₂CH₂CH₂NH₂
3. MeO-propyl-NH₂
4. cyclopropyl-CH₂-NH₂

TABLE 2-6-continued

$(CH_2)_{1-6}R^{14}$ Reagents

5. 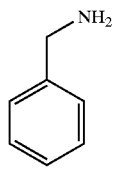

6. 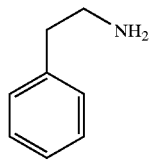

7. 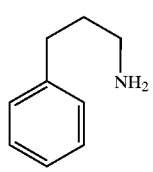

TABLE 2-7

$R^6/R^7$ Reagents

1. 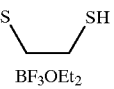
   BF$_3$OEt$_2$
2. NaBH$_4$
3. No reaction

TABLE 2-8

$R^8$ Reagents

1. 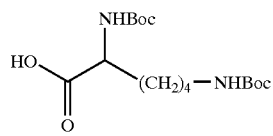

2. 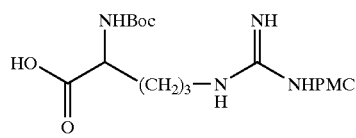

3. 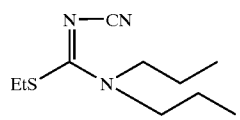

4. Me—N=C=O
5. Me—N=C=S

6. 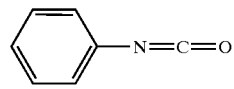

TABLE 2-8-continued

$R^8$ Reagents

7. 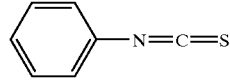

8. 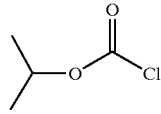

9. 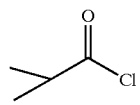

10. Me—SO$_2$Cl

Other preferred compounds of Formula I are those of Formulae Ib' or Ic' wherein —C(O)—L'—II' is:

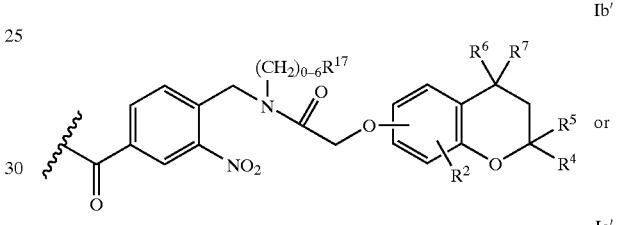

Ib'

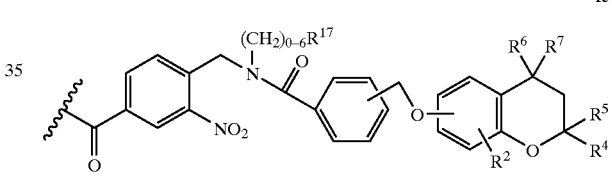

Ic'

$R^1$ may also be

O—Z—C(O)NH—CHR$^{18}$—((CH$_2$)$_{0-5}$R$^{17}$)$_{0-1}$ wherein $R^{18}$ is H or (CH$_2$)$_{0-5}$R$^{17}$.

$R^{17}$ may also be alkyl or substituted heterocycloalkyl. Substituted heterocycloalkyl means heterocycloalkyl substituted with loweralkyl or heteroaryl. Substituted aryl additionally means aryl substituted with loweralkyl substituted with aryl.

Scheme 12 may be modified by starting with analogs of compound 10 where $R^{17}$ is 'sound directly to N to produce analogs 11a', 12a', and 14a where $R^{17}$ is bound directly to N. Compounds of formulae 11a', 12a', 14, 14a, D, and 14' are useful as intermediates in the construction of combinatorial libraries and are especially useful in automated or batch mode syntheses thereof.

Scheme 14

A process alternative to that of Scheme 12 to produce the compounds 14' is shown in Scheme 14.

Functionalized supports such as amino-functionalized or hydroxy-terminating PEG grafted polystyrene beads are placed into a reaction vessel and are reacted with: 3-nitro-4-bromomethylbenzoic acid (Rich and Gurwara, *Tetra.Lett*, 1975, 301), to generate benzoylamide resin B. The resin is then reacted with amine C in THF at r.t. to yield amino resin D. Amine C can be replaced by aniline or a similar primary aromatic amine.

In an appropriately sized synthesis vessel is placed the amino resin D (1 equiv. of amino sites). A solvent such as DCM or DMSO is added, followed by an organic base such as triethylamine, pyridine, Hünig's base (di-isopropylethyl-amine), or 2,6-lutidine (10 equiv.). The resin is agitated for 15 min. before adding the acid halide Q(X=Cl,Br) (5 equiv.), or an equivalent activated acid, as a dilute solution in a solvent such as DCM. The resin is agitated for 4 hrs. and then washed with DCM and MeOH (5× each) to yield 14'.

Photolysis of 14' as by treatment by UV at 365 nm for 2 hours yields acetamide E.

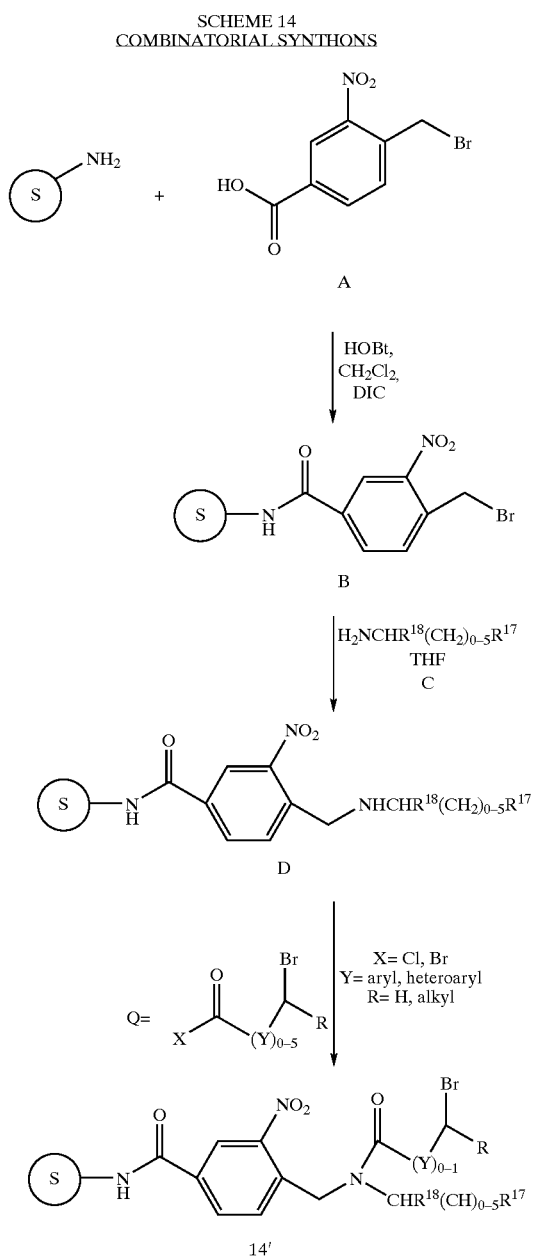

SCHEME 14
COMBINATORIAL SYNTHONS

EXAMPLE 3

Benzyl Acetamide Resin

To a solution of TentaGel® amino resin (2 g, 0.6 mmol), 3-nitro-4-bromomethylbenzoic acid (390 mg, 1.5 mmol), and HOBt (205 mg, 1.5 mmol) in 30 mL $CH_2Cl_2$ was added 1,3-diisopropyl-carbodiimide (250 μL, 1.5 mmol). The reaction mixture was shaken for 6–8 hr. until the Kaiser test indicated the completion of the reaction. The reagents were filtered and the resulting resin was washed (3×$CH_2Cl_2$, 3×$CH_3OH$ and 3×$CH_2Cl_2$) and then dried to give 3-nitro-4-/(bromomethyl)benzoylamide TentaGel resin.

To the above resin in 40 mL THF was added benzyl amine (1.3 mL, 12 mmol). After 8 hours shaking at room temperature, the resin was washed thoroughly (3× THF, 3× $CH_3OH$, and 3× $CH_2Cl_2$) and then dried to afford benzylamino TentaGel resin.

To the above benzylamino TentaGel resin (200 mg, 0.06 mmol) in 8 mL $CH_2Cl_2$ was added diisopropylethylamine (210 μL, 0.6 mmol). The reaction mixture was shaken for 2 hr. The resin was washed (3×$CH_2Cl_2$ and 3×$CH_3OH$).

EXAMPLE 4

N-Benzyl Bromoacetamide Resin

To benzylamino TentaGel resin, produced as in Example 3, (200 mg, 0.06 mmol) in 8 mL $CH_2Cl_2$ was added diisopropylethylamine (210 μL, 1.2 mmol) followed by bromoacetyl bromide (52 μL, 0.6 mmol). The reaction was shaken for 2 hr. The resin was washed (3×$CH_2Cl_2$ and 3×$CH_3OH$).

EXAMPLE 5

Amide Synthons

Following the procedures of Examples 3 and 4 bull substituting the amines of Table 5-1 for benzyl amine, analogous amides and bromoamides are produced.

TABLE 5-1

| AMINES |
| --- |
| 1. isopropylamine —$NH_2$ |
| 2. isobutylamine —$NH_2$ |
| 3. n-butylamine —$NH_2$ |
| 4. $H_3CO$—$NH_2$ |
| 5. $H_3CO$—$NH_2$ |
| 6. allylamine —$NH_2$ |
| 7. cyclopropylamine —$NH_2$ |
| 8. cyclopropylmethylamine —$NH_2$ |
| 9. cyclohexylamine —$NH_2$ |

TABLE 5-1-continued
AMINES
10. 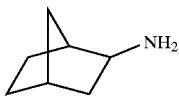
11. 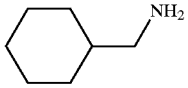
12. 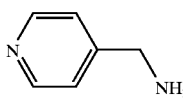
13. 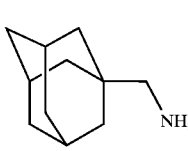
14. 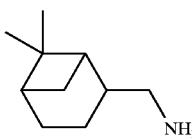
15. 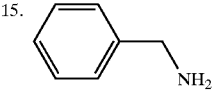
16. 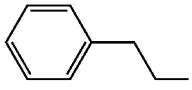
17. 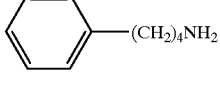
18. 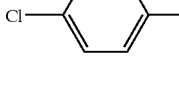
19. 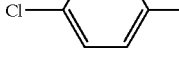
20. 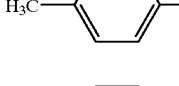
21. 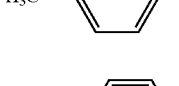
22. 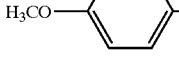
TABLE 5-1-continued
AMINES
23. 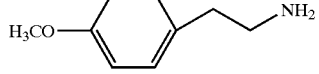
24. 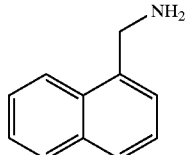
25. 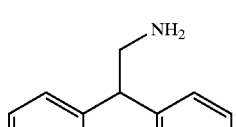
26. 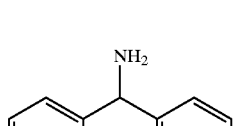
27. 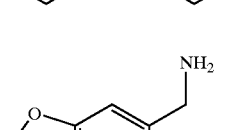
28. 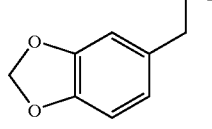
29. 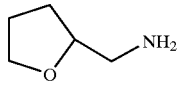
30. 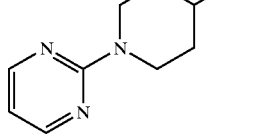
EXAMPLE 6
87,906 Compound Library
Following the procedure of Example 2 but replacing the compounds of Tables 2-3 and 2-8 therein respectively with the compounds of Tables 6-1 and 6-2, an 87,906 compound library is produced.

TABLE 6-1

R⁴/R⁵ Step 3 Reagents

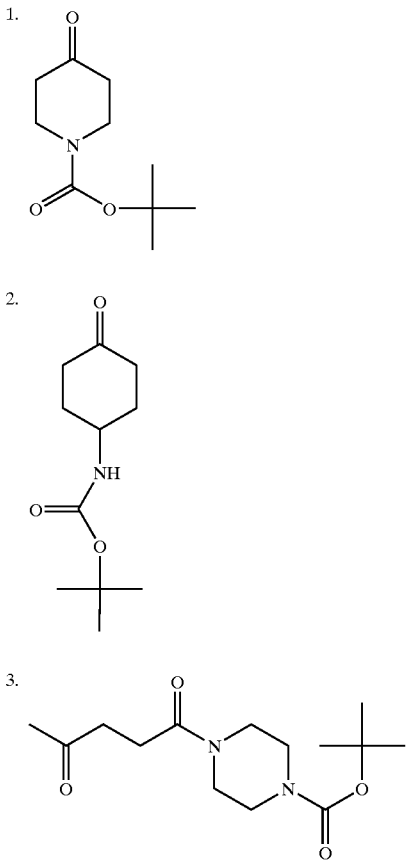

TABLE 6-2

R⁸ Reagents

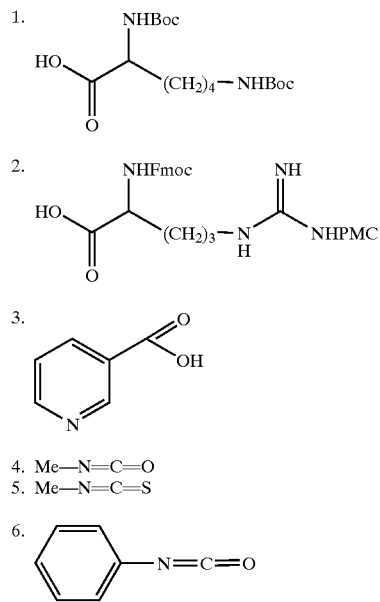

4. Me—N=C=O
5. Me—N=C=S

6. 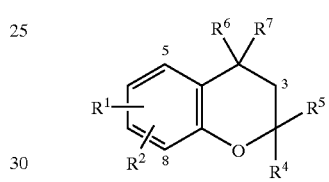

TABLE 6-2-continued

R⁸ Reagents

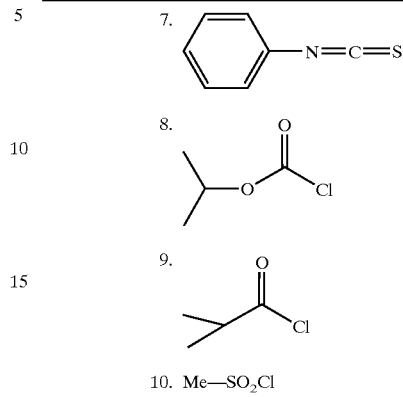

10. Me—SO₂Cl

What is claimed is:

1. A compound of the formula:

II $$\text{structure with } R^1, R^2, R^4, R^5, R^6, R^7 \text{ on chroman ring}$$

wherein:

$R^1$ is OH, O(CH$_2$)$_{1-2}$OH, OCH$_2$CO$_2$H, CO$_2$H, O—Z—C(O)NH(CH$_2$)$_{1-6}$R$^{17}$ or OCH$_2$-4-Phe-C(O)NH(CH$_2$)$_{1-6}$R$^{17}$;

$R^2$ is H or lower alkyl;

$R^3$ is H, alkyl, aryl, or arylalkyl;

$R^4$ and $R^5$ are each independently H, lower alkyl, or substituted lower alkyl where the substituents are 1–3 alkoxy, aryl, substituted aryl, carboxamido; or $R^4$ and $R^5$ taken together are —(CH$_2$)$_n$—, —(CH$_2$)$_2$—O—(CH$_2$)$_2$—, —CH$_2$—O—(CH$_2$)$_3$—, —(CH$_2$)$_2$—NR$^8$—CH$_2$)$_2$—, —CH$_2$—NR$^8$—(CH$_2$)$_m$—, —(CH$_2$)$_2$CH(NHR$^8$)(CH$_2$)$_2$—, —(CH$_2$)$_2$—S(O)$_{0-2}$—(CH$_2$)$_2$—, or —CH$_2$CH(N-loweralkyl)(CH$_2$)$_2$CHCH$_2$—;

one of $R^6$ and $R^7$ is H and the other is OH, or N(CH$_2$)$_{1-6}$R$^{14}$R$^{15}$; or $R^6$ and $R^7$ taken together are $$\text{cyclic structures}$$

$R^8$ is H, COOR$^9$, CONHR$^{10}$, CSNHR$^{11}$, COR$^{12}$, SO$_2$R$^{13}$, lower alkyl, aryl lower alkyl, heteroaryl, or heteroaryl lower alkyl, wherein aryl is optionally substituted with 1–3 substituents selected from lower alkyl, lower alkoxy, halo, CN, NH$_2$, COOH, CONH$_2$, and mono-lower alkylamino and wherein heteroaryl is a mono- or bicyclic heteroaromatic ring system of 5 to 10 members including 1 to 3 heteroatoms selected from O, N, and S and 0–3 substituents selected from halo, amino, cyano, lower alkyl, CONH$_2$, and S-lower alkyl;

R$^9$ is lower alkyl, aryl, aryl lower alkyl, heteroaryl, aryl substituted by 1–3 substituents selected from alkyl, alkenyl, alkoxy, and halo, or a 5- to 6-membered heterocyclic ring containing O or N as a heteroatom, wherein heteroaryl is a heteroaromatic ring of 5 to 6 members including 1 to 2 heteroatoms selected from O, N, and S and 0–2 substituents selected from lower alkyl, dialkylamino, lower alkoxy, and halo;

R$^{10}$ and R$^{11}$ are each independently lower alkyl, aryl, aryl lower alkyl or aryl substituted by 1–3 substituents selected from lower alkyl, halo, alkoxy and haloalkyl;

R$^{12}$ is lower alkyl, aryl, heteroaryl, aryl lower alkyl, heteroaryl lower alkyl, a 5- or 6-membered heterocyclic ring containing 1–2 heteroatoms selected from O, S, and N, a 5- or 6-membered heterocyclic ring containing 1–2 heteroatoms selected from O, S, and N-lower alkyl, or aryl substituted with 1–3 substituents selected from lower alkyl, alkoxy, halo, sulfamoyl, lower alkyl sulfamoyl, cyano, and phenyl;

R$^{13}$ is lower alkyl, aryl, or aryl substituted with 1–3 substituents selected from lower alkyl alkoxy, halo, CN, and haloalkyl;

R$^{14}$ is H; alkyl; alkyl substituted by 1–3 alkoxy, S-lower alkyl, sulfamoyl halo, alkylsulphonamido, or arylsulphonamido; alkenyl; alkynyl; aryl; substituted aryl; heteroaryl; substituted heteroaryl; heterocycloalkyl; —CH$_2$NR$^{16}$C(O)R$^{16}$; —C(O)NR$^{16}$R$^{16}$; —CH$_2$OC(O)R$^{16}$; or —CH$_2$SC(O)R$^{16}$;

R$^{15}$ is H, alkyl, —C(O)X, —C(S)X, or —C(NCN)NR$^3$R$^3$;

R$^{16}$ is lower alkyl, substituted lower alkyl, aryl, or substituted aryl;

R$^{17}$ is H; alkyl; alkyl substituted by 1–3 alkoxy, S-lower alkyl, sulfamoyl, halo, alkylsulphonamido, or arylsulphonamido; alkenyl; alkynyl; aryl; substituted aryl; heteroaryl; substituted heteroaryl; heterocycloalkyl; —CH$_2$NR$^{16}$C(O)R$^{16}$; —C(O)NR$^{16}$R$^{16}$; —CH$_2$OC(O)R$^{16}$; or —CH$_2$SC(O)R$^{16}$;

X is alkyl aryl, arylalkyl, O-loweralkyl, or —NR$^3$R$^3$;

Z is —(CH$_2$)$_{1-6}$—, optionally substituted with 1–3 lower alkyl; —CHR$^2$—; -Phe-CH$_2$—, where Phe is optionally mono-substituted with halogen, lower alkyl, or alkoxy; or heteroarylene —(CH$_2$)—;

m is 2 or 3; and n is 4–9;

or a pharmaceutically acceptable salt thereof.

2. A compound according to claim 1, wherein:

R$^1$ is —OCH$_2$CO$_2$H;

R$^2$ is —H;

R$^4$ and R$^5$ taken together are —(CH$_2$)$_2$—S(O)$_{0-2}$—(CH$_2$)$_2$—; and one of R$^6$ and R$^7$ is —H and the other is —H or —N(CH$_2$)$_{1-6}$R$^{14}$R$^{15}$.

3. A compound of claim 2 wherein:

R$^{14}$ is —H; and

R$^{15}$ is alkyl.

4. A compound of the formula:

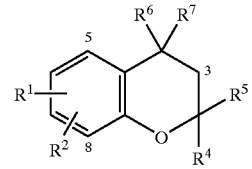

II wherein:

R$^1$ is OCH$_2$CO$_2$H;

R$^2$ is H;

R$^4$ and R$^5$ taken together are —(CH$_2$)$_2$—S—(O)$_2$—(CH$_2$)$_2$—; and one of R$^6$ and R$^7$ is —H and the other is —H or —N(CH$_2$)$_{1-6}$R$^{14}$R$^{15}$, wherein:

R$^{14}$ is H; alkyl; alkyl substituted by 1–3 alkoxy, S-lower alkyl, sulfamoyl, halo, alkylsulphonamido, or arylsulphonamido; alkenyl; alkynyl; aryl; substituted aryl; heteroaryl; substituted heteroaryl; heterocycloalkyl; —CH$_2$NR$^{16}$C(O)R$^{16}$; —C(O)NR$^{16}$R$^{16}$; —CH$_2$OC(O)R$^{16}$; or —CH$_2$SC(O)R$^{16}$;

wherein:

R$^{16}$ is lower alkyl, substituted lower alkyl, aryl, or substituted aryl; and R$^{15}$ is H, alkyl, —C(O)X, —C(S)X, or —C(NCN)NR$^3$R$^3$;

wherein:

X is alkyl, aryl, arylalkyl, O-loweralkyl, or —NR$^3$R$^3$; and

R$^3$ is H, alkyl, aryl, or arylalkyl.

5. A compound of claim 4, wherein:

R$^{14}$ is —H; and

R$^{15}$ is alkyl.

* * * * *

UNITED STATES PATENT AND TRADEMARK OFFICE
CERTIFICATE OF CORRECTION

PATENT NO. : 6,790,965 B1
DATED : September 14, 2004
INVENTOR(S) : Baldwin et al.

It is certified that error appears in the above-identified patent and that said Letters Patent is hereby corrected as shown below:

Column 102,
Lines 55 thru 60, structure delete "$\overset{O}{\|}$," at the beginning of the structure Signed and Sealed this Twenty-fifth Day of January, 2005

JON W. DUDAS
*Director of the United States Patent and Trademark Office*